(12) United States Patent
Smallheer et al.

(10) Patent No.: US 7,417,063 B2
(45) Date of Patent: Aug. 26, 2008

(54) BICYCLIC HETEROCYCLES USEFUL AS SERINE PROTEASE INHIBITORS

(75) Inventors: Joanne M. Smallheer, Yardley, PA (US); James R. Corte, Lawrenceville, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 500 days.

(21) Appl. No.: 11/103,139

(22) Filed: Apr. 11, 2005

(65) Prior Publication Data

US 2005/0228000 A1    Oct. 13, 2005

Related U.S. Application Data

(60) Provisional application No. 60/627,482, filed on Nov. 12, 2004, provisional application No. 60/561,792, filed on Apr. 13, 2004.

(51) Int. Cl.
*A61K 31/40* (2006.01)
*C07D 209/44* (2006.01)

(52) U.S. Cl. ........................... 514/416; 548/470

(58) Field of Classification Search ................ 514/416; 548/470
See application file for complete search history.

(56) References Cited

U.S. PATENT DOCUMENTS

| | | | |
|---|---|---|---|
| 4,581,354 A * | 4/1986 | Bell | 514/210.21 |
| 4,634,776 A * | 1/1987 | Bell | 548/493 |
| 4,885,295 A * | 12/1989 | Bell | 514/235.2 |
| 4,978,664 A * | 12/1990 | Bell | 514/235.2 |
| 5,013,732 A * | 5/1991 | Bell | 514/210.21 |
| 5,312,829 A | 5/1994 | Okada et al. | |
| 5,604,253 A | 2/1997 | Lau et al. | |
| 5,639,780 A | 6/1997 | Lau et al. | |
| 5,684,034 A | 11/1997 | Bach et al. | |
| 5,811,425 A | 9/1998 | Woods et al. | |
| 6,069,156 A | 5/2000 | Oku et al. | |
| 6,100,238 A | 8/2000 | Gyorkos et al. | |
| 6,166,023 A | 12/2000 | Schindler et al. | |
| 6,358,992 B1 | 3/2002 | Pamukcu et al. | |
| 6,653,304 B2 | 11/2003 | Leftheris et al. | |
| 6,858,577 B1 | 2/2005 | Zhang et al. | |
| 2003/0203909 A1 | 10/2003 | Ushio et al. | |
| 2004/0006123 A1 | 1/2004 | Alkan et al. | |
| 2004/0220206 A1 | 11/2004 | Smallheer et al. | |
| 2004/0235847 A1 | 11/2004 | Quan et al. | |

FOREIGN PATENT DOCUMENTS

| | | |
|---|---|---|
| WO | WO 93/02050 | 2/1993 |
| WO | WO 98/08818 | 3/1998 |
| WO | WO 99/12903 | 3/1999 |
| WO | WO 99/12935 | 3/1999 |
| WO | WO 99/43654 | 9/1999 |
| WO | WO 00/35886 | 6/2000 |
| WO | WO 01/27079 | 4/2001 |
| WO | WO01058869 | 8/2001 |
| WO | WO 03/101961 | 12/2003 |
| WO | WO 2004/050637 | 6/2004 |
| WO | WO 2004/062661 | 7/2004 |
| WO | WO 2004/080971 | 9/2004 |
| WO | WO 2004/094372 | 11/2004 |

OTHER PUBLICATIONS

Walsh, P.N., "Platelets and Factor XI Bypass the Contact System of Blood Coagulation", *Thromb. and Haemostasis*, 82(2), pp. 234-242, 1999.
Colman, R. Contact Activation Pathway: Inflammatory, Fibrinolytic, Anticoagulant, Antiadhesive, and Antiangiogenic Activities, *Hemostasis and thrombosis: basic principles and clinical practice*, Lippincott Williams & .Wilkins, 2001, pp. 103-122.
Schmaier, A.H., "Contact Activation", *Thrombosis and Hemorrhage*, Williams & Wilkins, 1998, Chapter 5, pp. 105-128.
Gailani, D., "Activation of Factor IX by Factor XIa", *Trends in Cardiovascular Medicine*, vol. 10, No. 5, 2000, pp. 198-204.
Bouma, B.N. et al., "Thrombin-Activatable Fibrinolysis Inhibitor (TAFI, Plasma Procarboxypeptidase B, Precarboxypeptidase R, Procarboxypeptidase U)", *Thrombosis. Research*, 2001, 101, pp. 329-354.
Gailani, D., "Gene Targeting in Hemostasis. Factor XI", *Frontiers in Bioscience*, 2001, 6, pp. d201-d207.
Gailani, D., et al., "A murine model of factor XI deficiency", *Blood Coagulation and Fibrinolysis*, 1997, vol. 8, pp. 134-144.
Minnema, M.C., et al., "Activation of Clotting Factors XI and IX in Patients with Acute Myocardial Infarction", *Arterioscler. Thromb. Vasc. Biol.*, 2000, 20, pp. 2489-2493.

(Continued)

*Primary Examiner*—Golam M. M. Shameem
*Assistant Examiner*—Susannah Chung
(74) *Attorney, Agent, or Firm*—Jing G. Sun

(57) ABSTRACT

The present invention provides compounds of Formula (I):

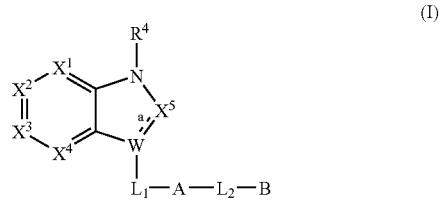

or a stereoisomer or pharmaceutically acceptable salt or solvate form thereof, wherein the variables A, B, $L_1$, $L_2$, $X^1$, $X^2$, $X^3$, $X^4$, $X^5$, $R^4$, and W are as defined herein. The compounds of Formula (I) are useful as selective inhibitors of serine protease enzymes of the coagulation cascade and/or contact activation system; for example thrombin, factor Xa, factor XIa, factor IXa, factor VIIa and/or plasma kallikrein. In particular, it relates to compounds that are selective factor XIa inhibitors. This invention also relates to pharmaceutical compositions comprising these compounds and methods of treating thromboembolic and/or inflammatory disorders using the same.

14 Claims, No Drawings

OTHER PUBLICATIONS

Murakami, T., et al., "Evaluation of Factor XIa-$\alpha_1$ —Antitrypsin in Plasma, a Contact Phase-Activated Coagulation Factor-Inhibitor Complex, in Patients With Coronary Artery Disease", *Arterioscler. Thromb. Vasc. Biol.*, 1995, vol. 15, No. 8, pp. 1107-1113.

Meijers, J.C.M., et al., "High Levels of Coagulation Factor XI as a Risk Factor for Venous Thrombosis", *N. Engl. J. Med.*, 2000, vol. 342, No. 10, pp. 696-701.

Komoriya et al., "Design, synthesis and biological activity of amidinobicyclic compounds (derivatives of DX-9065a) as factor Xa inhibitors: SAR study of S1 and aryl binding sites", *Bioorganic & Medicinal Chemistry*, vol. 12, pp. 2099-2114, 2004.

Zhang et al., "A Versatile Synthesis of 3-Substituted Indolines and Indoles", *J. Org. Chem.*, vol. 61, pp. 2594-2595, 1996.

Woods et al., "Thiazole Analogues of the NSAID Indomethacin as Selective COX-2 Inhibitors", *Bioorganic & Medicinal Chemistry Letters*, vol. 11, pp. 1325-1328, 2001.

Jacobs, R. T. et al., "Substituted 3-(Phenylmethyl)-1*H*-indole-5-carboxamides and 1-(Phenylmethyl)indole-6-carboxamides as Potent, Selective, Orally Active Antagonists of the Peptidoleukotrienes", J. Med. Chem., vol. 36, No. 3, pp. 394-409 (1993).

\* cited by examiner

BICYCLIC HETEROCYCLES USEFUL AS SERINE PROTEASE INHIBITORS

CROSS-REFERENCE TO RELATED APPLICATIONS

The present application claims the priority benefit of U.S. Provisional Application No. 60/561,792, filed Apr. 13, 2004 and the priority benefit of U.S. Provisional Application No. 60/627,482, filed Nov. 12, 2004, all of which are expressly incorporated fully herein by reference.

FIELD OF THE INVENTION

The present invention relates generally to compounds that inhibit serine proteases. In particular it is directed to novel bicyclic heterocycle derivatives of Formula (I):

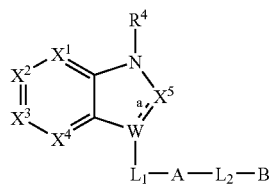

or a stereoisomer or a pharmaceutically acceptable salt, solvate, or prodrug form thereof, which are useful as selective inhibitors of serine protease enzymes of the coagulation cascade and/or contact activation system; for example thrombin, factor XIa, factor Xa, factor IXa and/or factor VIIa, and/or plasma kallikrein. In particular, it relates to compounds that are selective factor XIa inhibitors. This invention also relates to pharmaceutical compositions comprising these compounds and methods of using the same.

BACKGROUND OF THE INVENTION

Factor XIa is a plasma serine protease involved in the regulation of blood coagulation. While blood coagulation is a necessary and important part of the regulation of an organism's homeostasis, abnormal blood coagulation can also have deleterious effects. For instance, thrombosis is the formation or presence of a blood clot inside a blood vessel or cavity of the heart. Such a blood clot can lodge in a blood vessel blocking circulation and inducing a heart attack or stroke. Thromboembolic disorders are the largest cause of mortality and disability in the industrialized world.

Blood coagulation is initiated in vivo by the binding of tissue factor (TF) to Factor VII (FVII) to generate Factor VIIa (FVIIa). The resulting TF:FVIIa complex activates Factor IX (FIX) and Factor X (FX) which leads to the production of Factor Xa (FXa). The FXa that is generated catalyzes the transformation of prothrombin into small amounts of thrombin before this pathway is shut down by tissue factor pathway inhibitor (TFPI). The process of coagulation is then further propagated via the feedback activation of Factors V, VIII and XI by catalytic amounts of thrombin. (Walsh, P. N. *Thromb. Haemostasis.* 1999, 82, 234-242.) Factor XIa plays a key role in propagating this amplification loop and is thus an attractive target for anti-thrombotic therapy.

An alternative way of initiation of coagulation is operative when blood is exposed to artificial surfaces (e.g., during hemodialysis, 'on-pump' cardiovascular surgery, vessel grafts, bacterial sepsis). This process is also termed contact activation. Surface absorption of factor XII leads to a conformational change in the factor XII molecule, thereby facilitating activation to proteolytic active factor XII molecules (factor XIIa and factor XIIf). Factor XIIa (or XIIf) has a number of target proteins, including plasma prekallikrein and factor XI. Active plasma kallikrein further activates factor XII, leading to an amplification of contact activation. Contact activation is a surface mediated process responsible in part for the regulation of thrombosis and inflammation, and is mediated, at least in part, by fibrinolytic-, complement-, kininogen/kinin-, and other humoral and cellular pathways (for review, Coleman, R. *Contact Activation Pathway*, pages 103-122 in *Hemostasis and Thrombosis*, Lippincott Williams & Wilkins 2001; Schmaier A. H. *Contact Activation*, pages 105-128 in *Thrombosis and Hemorrhage*, 1998).

Factor XI is a zymogen of a trypsin-like serine protease and is present in plasma at a relatively low concentration. Proteolytic activation at an internal R369-I370 bond yields a heavy chain (369 amino acids) and a light chain (238 amino acids). The latter contains a typical trypsin-like catalytic triad (H413, D464, and S557). Activation of factor XI by thrombin is believed to occur on negatively charged surfaces, most likely on the surface of activated platelets. Platelets contain high affinity (0.8 nM) specific sites (130-500/platelet) for activated factor XI. After activation, factor XIa remains surface bound and recognizes factor IX as its normal macromolecular substrate. (Galiani, D. *Trends Cardiovasc. Med.* 2000, 10, 198-204.)

In addition to the feedback activation mechanisms described above, thrombin activates thrombin activated fibrinolysis inhibitor (TAFI), a plasma carboxypeptidase that cleaves C-terminal lysine and arginine residues on fibrin, reducing the ability of fibrin to enhance tissue-type plasminogen activator (tPA) dependent plasminogen activation. In the presence of antibodies to FXIa, clot lysis can occur more rapidly independent of plasma TAFI concentration. (Bouma, B. N. et al. *Thromb. Res.* 2001, 101, 329-354.) Thus, inhibitors of factor XIa are expected to be anticoagulant and profibrinolytic.

Genetic evidence indicates that factor XI is not required for normal homeostasis, implying a superior safety profile of the factor XI mechanism compared to competing antithrombotic mechanisms. In contrast to hemophilia A (factor VIII deficiency) or hemophilia B (factor IX deficiency), mutations of the factor XI gene causing factor XI deficiency (hemophilia C) result in only a mild to moderate bleeding diathesis characterized primarily by postoperative or posttraumatic, but rarely spontaneous hemorrhage. Postoperative bleeding occurs mostly in tissue with high concentrations of endogenous fibrinolytic activity (e.g., oral cavity, and urogenital system). The majority of the cases are fortuitously identified by preoperative prolongation of APTT (intrinsic system) without any prior bleeding history.

The increased safety of inhibition of XIa as an anticoagulation therapy is further supported by the fact that Factor XI knock-out mice, which have no detectable factor XI protein, undergo normal development, and have a normal life span. No evidence for spontaneous bleeding has been noted. The APTT (intrinsic system) is prolonged in a gene dose-dependent fashion. Interestingly, even after severe stimulation of the coagulation system (tail transaction), the bleeding time is not significantly prolonged compared to wild-type and heterozygous litter mates. (Gailani, D. *Frontiers in Bioscience* 2001, 6, 201-207; Gailani, D. et al. *Blood Coagulation and Fibrinolysis* 1997, 8, 134-144.) Taken together, these observations suggest that high levels of inhibition of factor XIa should be well tolerated. This is in contrast to gene targeting experiments with other coagulation factors.

In vivo activation of factor XI can be determined by complex formation with either C1 inhibitor or alpha 1 antitrypsin. In a study of 50 patients with acute myocardial infarction (AMI), approximately 25% of the patients had values above the upper normal range of the complex ELISA. This study can be viewed as evidence that at least in a subpopulation of patients with AMI, factor XI activation contributes to thrombin formation (Minnema, M. C. et al. *Arterioscler. Thromb. Vasc. Biol.* 2000, 20, 2489-2493). A second study establishes a positive correlation between the extent of coronary arteriosclerosis and factor XIa in complex with alpha 1 antitrypsin (Murakami, T. et al. *Arterioscler Thromb Vasc Biol* 1995, 15, 1107-1113.). In another study, Factor XI levels above the 90th percentile in patients were associated with a 2.2-fold increased risk for venous thrombosis (Meijers, J. C. M. et al. *N. Engl. J. Med.* 2000, 342, 696-701.).

Plasma kallikrein is a zymogen of a trypsin-like serine protease and is present in plasma at 35 to 50 μg/mL. The gene structure is similar to that of factor XI, overall, the amino acid sequence of plasma kallikrein has 58% homology to factor XI. Proteolytic activation by factor XIIa at an internal I 389-R390 bond yields a heavy chain (371 amino acids) and a light chain (248 amino acids). The active site of kallikrein is contained in the light chain. The light chain of plasma kallikrein reacts with protease inhibitors, including alpha 2 macroglobulin and C1-inhibitor. Interestingly, heparin significantly accelerates the inhibition of plasma kallikrein by antithrombin III in the presence of high molecular weight kininogen (HMWK). In blood, the majority of plasma kallikrein circulates in complex with HMWK. Kallikrein cleaves HMWK to liberate bradykinin. Bradykinin release results in increase of vascular permeability and vasodilation (for review, Coleman, R. *Contact Activation Pathway*, pages 103-122 in *Hemostasis and Thrombosis*, Lippincott Williams & Wilkins 2001; Schmaier A. H. *Contact Activation*, pages 105-128 in *Thrombosis and Hemorrhage*, 1998).

Proteins or peptides that reportedly inhibit Factor XIa are disclosed in WO 01/27079. There are advantages in using small organic compounds, however, in preparing pharmaceuticals, e.g., small compounds generally have better oral bioavailability and compatibility in making formulations to aid in delivery of the drug as compared with large proteins or peptides. Small molecule inhibitors of Factor XIa are disclosed in WO 2004/080971 and WO 2004/094372.

The present invention discloses novel bicyclic heterocycle derivatives that are selective, non-peptide inhibitors of coagulation Factor XIa and/or plasma kallikrein and as such are useful in the treatment of thromboembolic and/or inflammatory disorders.

In addition, it is also desirable to find new compounds with improved pharmacological characteristics compared with known serine protease inhibitors. For example, it is preferred to find new compounds with improved factor XIa inhibitory activity and selectivity for factor XIa versus other serine proteases. Also, it is preferred to find new compounds with improved plasma kallikrein inhibitory activity and selectivity for plasma kallikrein versus other serine proteases. It is also desirable and preferable to find compounds with advantageous and improved characteristics in one or more of the following categories, but are not limited to: (a) pharmaceutical properties; (b) dosage requirements; (c) factors which decrease blood concentration peak-to-trough characteristics; (d) factors that increase the concentration of active drug at the receptor; (e) factors that decrease the liability for clinical drug-drug interactions; (f) factors that decrease the potential for adverse side-effects; and (g) factors that improve manufacturing costs or feasibility.

SUMMARY OF THE INVENTION

Accordingly, the present invention provides novel bicyclic heterocycle derivatives, and analogues thereof, which are useful as selective inhibitors of serine protease enzymes, especially factor XIa and/or plasma kallikrein, or stereoisomers or pharmaceutically acceptable salts, solvates, or prodrugs thereof.

The present invention also provides processes and intermediates for making the compounds of the present invention, or stereoisomers or pharmaceutically acceptable salts, solvates, or prodrugs thereof.

The present invention also provides pharmaceutical compositions comprising a pharmaceutically acceptable carrier and a therapeutically effective amount of at least one of the compounds of the present invention, or a stereoisomer or a pharmaceutically acceptable salt, solvate, or prodrug thereof.

The present invention also provides a method for modulation of the coagulation cascade and/or the contact activation system comprising administering to a host in need of such treatment a therapeutically effective amount of at least one of the compounds of the present invention, or a stereoisomer or a pharmaceutically acceptable salt, solvate, or prodrug thereof.

The present invention also provides a method for treating thromboembolic disorders comprising administering to a host in need of such treatment a therapeutically effective amount of at least one of the compounds of the present invention, or a stereoisomer or a pharmaceutically acceptable salt, solvate, or prodrug thereof.

The present invention also provides a method for treating inflammatory diseases disorders comprising administering to a host in need of such treatment a therapeutically effective amount of at least one of the compounds of the present invention, or a stereoisomer or a pharmaceutically acceptable salt, solvate, or prodrug thereof.

The present invention also provides novel bicyclic heterocycle derivatives, and analogues thereof, for use in therapy.

The present invention also provides the use of bicyclic heterocycle derivatives, and analogues thereof, for the manufacture of a medicament for the treatment of a thromboembolic disorder.

The present invention also provides the use of bicyclic heterocycle derivatives, and analogues thereof, for the manufacture of a medicament for the treatment of an inflammatory disorder.

These and other embodiments, which will become apparent during the following detailed description, have been achieved by the inventors' discovery that the presently claimed novel compounds of the present invention, or stereoisomers or pharmaceutically acceptable salts, solvates, or prodrugs thereof, are effective factor XIa inhibitors and/or plasma kallikrein inhibitors.

DETAILED DESCRIPTION OF THE INVENTION

In a first aspect, the present invention provides, inter alia, compounds of Formula (I):

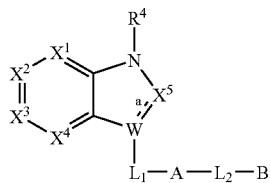

(I)

or stereoisomers or pharmaceutically acceptable salts, solvates, or prodrugs thereof, wherein:

a is a single or double bond;

$L_1$ is —$(CR^6R^{6a})_{1-2}$—, —$NR^7$—, —$C(O)$—, —$S(O)_p$—, —$(CR^6R^{6a})C(O)$—, —$C(O)(CR^6R^{6a})$—, —$(CR^6R^{6a})O$—, —$O(CR^6R^{6a})$—, —$(CR^6R^{6a})NR^7$—, —$NR^7(CR^6R^{6a})$—, —$(CR^6R^{6a})S(O)_p$—, —$S(O)_p(CR^6R^{6a})$—, —$C(O)NR^8$—, —$NR^8C(O)$—, —$S(O)NR^8$—, —$S(O)_2NR^8$—, —$NR^8S(O)$—, or —$NR^8S(O)_2$—;

$L_2$ is a bond, —$(CR^6R^{6a})_{1-2}$—, —$O$—, —$NR^7$—, —$C(O)$—, —$S(O)_p$—, —$(CR^6R^{6a})C(O)$—, —$C(O)(CR^6R^{6a})$—, —$(CR^6R^{6a})O$—, —$O(CR^6R^{6a})$—, —$(CR^6R^{6a})NR^7$—, —$NR^7(CR^6R^{6a})$—, —$(CR^6R^{6a})S(O)_p$—, —$S(O)_p(CR^6R^{6a})$—, —$C(O)O$—, —$OC(O)$—, —$C(O)NR^{10}$—, —$NR^{10}C(O)$—, —$S(O)NR^{10}$—, —$S(O)_2NR^{10}$—, —$NR^{10}S(O)$—, or —$NR^{10}S(O)_2$—;

A is phenylene substituted with 0-3 $R^{11}$ and 0-1 $R^{12}$, or a 5-6 membered heteroaryl other than thiazolyl, comprising: carbon atoms and 1-4 heteroatoms selected from N, O, and S, and substituted 0-3 $R^{11}$ and 0-1 $R^{12}$; provided that the groups $L_1$ and $L_2$ are attached to said phenylene or heteroaryl in a 1,2- or 1,3-orientation;

B is $C_{3-10}$ carbocycle substituted with 0-3 $R^{11}$ and 0-1 $R^{12}$, or a 5-12 membered heterocycle comprising: carbon atoms and 1-4 heteroatoms selected from N, O, and $S(O)_p$, and substituted with 0-3 $R^{11}$ and 0-1 $R^{12}$;

W is C or $CR^5$;

$X^1$, $X^2$, $X^3$ and $X^4$ independently represent $CR^1$, $CR^2$, $CR^3$ or N;

$X^5$ is $CR^5$, $CHR^5$, or N;

$R^1$ is H, —$NH_2$, —$NH(C_{1-3}$ alkyl), —$N(C_{1-3}$ alkyl)$_2$, —$C(=NH)NH_2$, —$C(=NOH)NH_2$, —$CONH_2$, —$CH_2NH_2$, —$CH_2NH(C_{1-3}$ alkyl), —$CH_2N(C_{1-3}$ alkyl)$_2$, —$CH_2CH_2NH_2$, —$CH_2CH_2NH(C_{1-3}$ alkyl), —$CH_2CH_2N(C_{1-3}$ alkyl)$_2$, —$C(=NR^{8a})NR^7R^9$, —$C(=NR^{8a})NR^{8a}R^9$, —$NHC(=NR^{8a})NR^7R^9$, —$NR^8CH(=NR^{8a})$, —$NR^7R^8$, —$CONR^{7a}R^8$, —$S(O)_pNR^8R^9$, F, Cl, Br, I, $OCF_3$, $CF_3$, $OR^a$, $SR^a$, CN or $C_{1-6}$ alkyl substituted with 1 $R^{1a}$;

$R^{1a}$ is H, —$C(=NR^{8a})NR^7R^9$, —$NHC(=NR^{8a})NR^7R^9$, —$ONHC(=NR^{8a})NR^7R^9$, —$NR^8CH(=NR^{8a})$, —$NR^7R^8$, —$CONR^{7a}R^8$, F, Cl, Br, I, $OCF_3$, $CF_3$, $OR^a$, $SR^a$, or CN;

$R^2$ is H, F, Cl, Br, I, $OCF_3$, $CF_3$, $OR^a$, $SR^a$, CN, $NO_2$, —$NR^7R^8$, —$CONR^{7a}R^8$, —$NR^{10}C(O)R^b$, —$S(O)_pNR^8R^9$, —$S(O)R^c$, —$S(O)_2R^c$, $C_{1-6}$ alkyl substituted with 0-2 $R^{2a}$, $C_{2-6}$ alkenyl substituted with 0-2 $R^{2a}$, $C_{2-6}$ alkynyl substituted with 0-2 $R^{2a}$, —$(CH_2)_r$—$C_{3-10}$ carbocycle substituted with 0-3 $R^{2b}$, or —$(CH_2)_r$-5-10 membered heterocycle comprising: carbon atoms and 1-4 heteroatoms selected from N, O, and $S(O)_p$, and substituted with 0-3 $R^{2b}$;

$R^{2a}$ is, independently at each occurrence, H, F, $OCF_3$, $CF_3$, $OR^a$, $SR^a$, CN, —$NR^7R^8$, —$CONR^{7a}R^8$, —$NR^{10}C(O)R^b$, —$S(O)_pNR^8R^9$, —$S(O)R^c$, or —$S(O)_2R^c$;

$R^{2b}$ is, independently at each occurrence, H, F, Cl, Br, I, =O, $OR^a$, $SR^a$, CN, $NO_2$, $CF_3$, —$SO_2R^c$, —$NR^7R^8$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy-, $C_{1-4}$ alkyloxy-, $C_{1-4}$ alkylthio-, $C_{1-4}$ alkyl-CO—, or $C_{1-4}$ alkyl-CONH—;

alternately, when $R^1$ and $R^2$ are substituted on adjacent ring atoms, they can be taken together with the ring atoms to which they are attached to form a 5-7 membered carbocycle or heterocycle substituted with 0-2 $R^{2b}$;

$R^3$ is H, F, Cl, Br, I, $OCF_3$, $CF_3$, $OR^a$, $SR^a$, CN, $NO_2$, —$NR^7R^8$, —$CONR^{7a}R^8$, —$NR^{10}C(O)R^b$, —$S(O)_pNR^8R^9$, —$S(O)R^c$, —$S(O)_2R^c$, $C_{1-6}$ alkyl substituted with 0-2 $R^{3a}$, $C_{2-6}$ alkenyl substituted with 0-2 $R^{3a}$, $C_{2-6}$ alkynyl substituted with 0-2 $R^{3a}$, —$(CH_2)_r$—$C_{3-10}$ carbocycle substituted with 0-3 $R^{3b}$, or —$(CH_2)_r$-5-10 membered heterocycle comprising: carbon atoms and 1-4 heteroatoms selected from N, O, and $S(O)_p$, and substituted with 0-3 $R^{3b}$;

$R^{3a}$ is, independently at each occurrence, H, F, $OCF_3$, $CF_3$, $OR^a$, $SR^a$, CN, —$NR^7R^8$, —$CONR^{7a}R^8$, —$NR^{10}C(O)R^b$, —$S(O)_pNR^8R^9$, —$S(O)R^c$, or —$S(O)_2R^c$;

$R^{3b}$ is, independently at each occurrence, H, F, Cl, Br, I, $OR^a$, $SR^a$, CN, $NO_2$, $CF_3$, —$SO_2R^c$, —$NR^7R^8$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy-, $C_{1-4}$ alkyloxy-, $C_{1-4}$ alkylthio-, $C_{1-4}$ alkyl-CO—, or $C_{1-4}$ alkyl-CONH—;

$R^4$ is H, $C_{1-6}$ alkyl substituted with 0-2 $R^{4a}$, $C_{2-6}$ alkenyl substituted with 0-2 $R^{4a}$, $C_{2-6}$ alkynyl substituted with 0-2 $R^{4a}$, —$(CH_2)_r$—$COR^{7a}$, —$(CH_2)_r$—$CONR^{7a}R^8$, benzyl-S(O)$_2$—, $(C_{1-6}$ alkyl)-S(O)$_2$—, phenyl-S(O)$_2$—, —$(CH_2)_r$—$C_{3-10}$ carbocycle substituted with 0-3 $R^{4b}$, or —$(CH_2)_r$-5-10 membered heteroaryl comprising: carbon atoms and 1-4 heteroatoms selected from N, O, and $S(O)_p$, and substituted with 0-3 $R^{4b}$;

$R^{4a}$ is, independently at each occurrence, H, $C_{1-4}$ alkyl, $OR^a$, F, =O, $CF_3$, CN, $NO_2$, —$C(O)R^a$, —$C(O)OR^a$, —$C(O)NR^1OR^8$, —$NR^{10}COR^a$, —$NR^{10}C(O)OR^c$, —$NR^{10}SO_2R^c$, or —$S(O)_pR^c$;

$R^{4b}$ is, independently at each occurrence, H, =O, $OR^a$, F, Cl, Br, I, CN, $NO_2$, —$NR^7R^8$, —$C(O)R^a$, —$CO_2R^a$, —$NR^8C(O)R^a$, —$CONR^{7a}R^8$, —$SO_2NR^8R^9$, —$NR^8SO_2NR^8R^9$, —$NR_8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl substituted with 0-2 $R^e$, $C_{2-6}$ alkenyl substituted with 0-2 $R^e$, or $C_{2-6}$ alkynyl substituted with 0-2 $R^e$;

$R^5$ is H, F, $OCF_3$, $CF_3$, $OR^a$, $SR^a$, CN, $NO_2$, —$NR^7R^8$, —$CONR^{7a}R^8$, —$NR^{10}C(O)R^b$, —$S(O)_pNR^8R^9$, —$S(O)R^c$, —$S(O)_2R^c$, $C_{1-6}$ alkyl substituted with 0-2 $R^{5a}$, $C_{2-6}$ alkenyl substituted with 0-2 $R^{5a}$, $C_{2-6}$ alkynyl substituted with 0-2 $R^{5a}$, —$(CH_2)_r$—$C_{3-10}$ carbocycle substituted with 0-3 $R^{5b}$, or —$(CH_2)_r$-5-10 membered heterocycle comprising: carbon atoms and 1-4 heteroatoms selected from N, O, and $S(O)_p$, and substituted with 0-3 $R^{5b}$;

$R^{5a}$ is, independently at each occurrence, H, F, $OCF_3$, $CF_3$, $OR^a$, $SR^a$, CN, —$NR^7R^8$, —$CONR^8R^{10}$, —$NR^{10}C(O)R^b$, —$S(O)_pNR^8R^{10}$, —$NR^{10}S(O)_pR^c$, —$S(O)R^c$, or —$S(O)_2R^c$;

$R^{5b}$ is, independently at each occurrence, H, F, Cl, Br, I, $OR^a$, $SR^a$, CN, $NO_2$, $CF_3$, —$SO_2R^c$, —$NR^7R^8$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy-, $C_{1-4}$ alkyloxy-, $C_{1-4}$ alkylthio-, $C_{1-4}$ alkyl-CO—, or $C_{1-4}$ alkyl-CONH—;

$R^6$ is, independently at each occurrence, H, $C_{1-4}$ alkyl, —$(CH_2)_r$—$CO_2R^a$, —$(CH_2)_rS(O)_2NR^{7a}R^8$, or —$(CH_2)_r$—$OR^a$;

$R^{6a}$ is, independently at each occurrence, H or $C_{1-4}$ alkyl;

$R^7$ is, independently at each occurrence, H, $C_{1-6}$ alkyl, —$(CH_2)_n$-phenyl, $(C_{1-6}$ alkyl)-CO—, $(C_{3-6}$ cycloalkyl)-$C_{0-4}$ alkyl-CO—, $(C_{6-10}$ aryl)-$C_{0-4}$ alkyl-CO—, (5-10 membered heteroaryl)-$C_{0-4}$ alkyl-CO—, $(C_{1-4}$ alkyl)OC(O)—, $(C_{6-10}$ aryl)-$(C_{1-4}$ alkyl)-OC(O)—, (5-10 membered heteroaryl)-

CH₂—OC(O)—, (C₁₋₄ alkyl)-C(O)O—(C₁₋₄ alkyl)-OC(O)—, (C₆₋₁₀ aryl)-C(O)O—(C₁₋₄ alkyl)-OC(O)—, (C₁₋₆ alkyl)-NHC(O)—, (C₁₋₆ alkyl)₂—NHC(O)—, (C₆₋₁₀ aryl)-C₀₋₄ alkyl-NHC(O)—, (5-10 membered heteroaryl)-C₀₋₄ alkyl-NHC(O)—, (C₁₋₆ alkyl)-S(O)₂—, (C₆₋₁₀ aryl)-C₀₋₄ alkyl-S(O)₂—, or (5-10 membered heteroaryl)-C₀₋₄ alkyl-S(O)₂—; wherein said phenyl, aryl and heteroaryl are substituted with 0-2 $R^f$;

$R^{7a}$ is, independently at each occurrence, H, $C_{1-4}$ alkyl substituted with 0-2 $R^{7b}$ and/or 0-2 $R^{7c}$, —(CH₂)$_r$—$C_{3-10}$ carbocycle substituted with 0-3 $R^f$, or a —(CH₂)$_r$-5-12 membered heterocycle comprising: carbon atoms and 1-4 heteroatoms selected from N, O, and S(O)$_p$, and substituted 0-3 $R^f$;

$R^{7b}$ is, independently at each occurrence, =O, OR$^g$, F, CN, NO₂, —NR⁷R⁸, —C(O)R$^g$, —CO₂R$^g$, —NR⁸C(O)R$^g$, —CONR⁸R⁹, —NR⁸C(O)NR⁸R⁹, I—SO₂NR⁸R⁹, —NR⁸SO₂NR⁸R⁹, —NR⁸SO₂—$C_{1-4}$ alkyl, —NR⁸SO₂CF₃, —NR⁸SO₂-phenyl, —S(O)₂CF₃, —S(O)$_p$—$C_{1-4}$ alkyl, —S(O)$_p$-phenyl, or —(CF₂)$_r$CF₃;

$R^{7c}$ is, independently at each occurrence, $C_{3-10}$ carbocycle substituted with 0-3 $R^f$; or a 5-12 membered heterocycle comprising: carbon atoms and 1-4 heteroatoms selected from N, O, and S(O)$_p$, and substituted 0-3 $R^f$;

$R^8$ is, independently at each occurrence, H, $C_{1-6}$ alkyl, or —(CH₂)$_n$-phenyl;

$R^{8a}$ is, independently at each occurrence, H, OH, $C_{1-6}$ alkyl, $C_{1-4}$ alkoxy, ($C_{6-10}$ aryl)-$C_{1-4}$ alkoxy, —(CH₂)$_n$-phenyl, ($C_{1-6}$ alkyl)-CO—, ($C_{6-10}$ aryl)-$C_{0-4}$ alkyl-CO—, ($C_{3-6}$ cycloalkyl)-$C_{0-4}$ alkyl-CO—, (5-10 membered heteroaryl)-$C_{0-4}$ alkyl-CO—, ($C_{1-6}$ alkyl)OC(O)—, ($C_{6-10}$ aryl)-$C_{1-4}$ alkyl-OC(O)—, ($C_{1-4}$ alkyl)-C(O)O—(C 4 alkyl)-OC(O)—, ($C_{6-10}$ aryl)-C(O)O—($C_{1-4}$ alkyl)-OC(O)—, ($C_{1-6}$ alkyl)C(O)O—, ($C_{6-10}$ aryl)-($C_{0-4}$ alkyl)-C(O)O—, or (5-10 membered heteroaryl)-$C_{0-4}$ alkyl-OC(O)—; wherein said phenyl, aryl and heteroaryl are substituted with 0-2 $R^f$;

alternatively, $R^7$ and $R^8$, or $R^{7a}$ and $R^8$, when attached to the same nitrogen, combine to form a 5-10 membered heterocyclic ring comprising: carbon atoms and 0-2 additional heteroatoms selected from N, O, and S(O)$_p$, and optionally substituted with 0-2 $R^d$;

$R^9$ is, independently at each occurrence, H, $C_{1-6}$ alkyl, or —(CH₂)$_n$-phenyl;

$R^{10}$ is, independently at each occurrence, H, $C_{1-6}$ alkyl substituted with 0-2 $R^{10a}$, $C_{2-6}$ alkenyl substituted with 0-2 $R^{10a}$, $C_{2-6}$ alkynyl substituted with 0-2 $R^{10a}$ (CH₂)$_r$—$C_{3-10}$ carbocycle substituted with 0-3 $R^{10b}$, or —(CH₂)$_r$-5-10 membered heterocycle comprising carbon atoms and 1-4 heteroatoms selected from N, O, and S(O)$_p$, and substituted with 0-3 $R^{10b}$;

$R^{10a}$ is, independently at each occurrence, H, $C_{1-4}$ alkyl, OR$^a$, F, =O, CF₃, CN, NO₂, —C(O)R$^a$, —CO₂R$^a$, —CONR$^{7a}$R⁸, or —S(O)$_p$R$^c$;

$R^{10b}$ is, independently at each occurrence, H, =O, OR$^a$, F, Cl, Br, I, CN, NO₂, —NR⁷R⁸, —C(O)R$^a$, —CO₂R$^a$, —NR⁸C(O)R$^a$, —CONR$^{7a}$R⁸, —SO₂NR⁸R⁹, —NR⁸SO₂NR⁸R⁹, —NR⁸SO₂—$C_{1-4}$ alkyl, —NR⁸SO₂CF₃, —NR⁸SO₂-phenyl, —S(O)₂CF₃, —S(O)$_p$—$C_{1-4}$ alkyl, —S(O)$_p$-phenyl, —(CF₂)$_r$CF₃, $C_{1-6}$ alkyl substituted with 0-2 $R^e$, $C_{2-6}$ alkenyl substituted with 0-2 $R^e$, or $C_{2-6}$ alkynyl substituted with 0-2 $R^e$;

$R^{11}$ is, independently at each occurrence, H, =O, —(CH₂)$_r$—OR$^a$, F, Cl, Br, I, CF₃, CN, NO₂, —(CH₂)$_r$—NR⁷R⁸, —(CH₂)$_r$—C(=NR⁸)NR⁷R⁹, —C(O)R$^a$, —CO₂R$^a$, —(CH₂)$_r$—NR⁸C(O)R$^a$, —NR⁸C(O)OR$^c$, —NR⁸CO(CH₂)$_r$CO₂R$^a$, —CONR$^{7a}$R⁸, —NR⁸C(O)NR⁸R¹⁰, —SO₂NR⁸R¹⁰, —NR⁸SO₂NR⁸R¹⁰, —NR⁸SO₂—$C_{1-4}$ alkyl, —NR⁸SO₂CF₃, —NR⁸SO₂-phenyl, —S(O)₂CF₃, —S(O)$_p$—$C_{1-4}$ alkyl, —S(O)$_p$-phenyl, —(CF₂)$_r$CF₃, $C_{1-6}$ alkyl substituted with 0-2 $R^{11a}$, $C_{2-6}$ alkenyl substituted with 0-2 $R^{11a}$, $C_{2-6}$ alkynyl substituted with 0-2 $R^{11a}$, $C_{1-6}$ alkyl substituted with 0-2 $R^{11b}$, $C_{2-6}$ alkenyl substituted with 0-2 $R^{11b}$, $C_{2-6}$ alkynyl substituted with 0-2 $R^{11b}$, phenyl substituted with 0-3 $R^c$ and/or 0-3 $R^d$, or a 5-7 membered heterocycle comprising: carbon atoms and 1-4 heteroatoms selected from N, O, and S(O)$_p$, and substituted with 0-3 $R^c$ and/or 0-3 $R^d$;

$R^{11a}$ is, independently at each occurrence, =O, OR$^a$, F, Cl, Br, I, CN, NO₂, —NR⁷R⁸, —C(O)R$^a$, —CO₂R$^a$, —NR⁸C(O)R$^c$, —CONR$^{7a}$R⁸, —NR⁸C(O)NR⁸R¹⁰, —SO₂NR⁸R¹⁰, —NR⁸SO₂NR⁸R¹⁰, —NR¹⁰SO₂—$C_{1-4}$ alkyl, —NR¹⁰SO₂CF₃, —NR¹⁰SO₂-phenyl, —S(O)₂CF₃, —S(O)$_p$—$C_{1-4}$ alkyl, —S(O)$_p$-phenyl, or —(CF₂)$_r$CF₃;

$R^{11b}$ is, independently at each occurrence, $C_{3-10}$ carbocycle substituted with 0-3 $R^d$, or a 5-12 membered heterocycle comprising: carbon atoms and 1-4 heteroatoms selected from N, O, and S(O)$_p$, and substituted 0-3 $R^d$;

$R^{12}$ is, independently at each occurrence, OR$^{12a}$, —CH₂OR$^{12a}$, —C(O)NR$^{7a}$R⁸, —(CH₂)$_r$CO₂R$^{12a}$, —(CH₂)$_r$SO₃H, —OSO₃H, —(CH₂)$_r$PO₃H, —OPO₃H₂, —PO₃H₂, —NHCOCF₃, —NHSO₂CF₃, —CONHNHSO₂CF₃, —C(CF₃)₂OH, —SO₂NHR$^{12a}$, —CONHSO₂NHR$^{12a}$, —SO₂NHCOR$^{12b}$, —SO₂NHCO₂R$^{12b}$, —CONHSO₂R$^{12b}$, —NHSO₂R$^{12b}$, —CONHOR$^{12a}$,

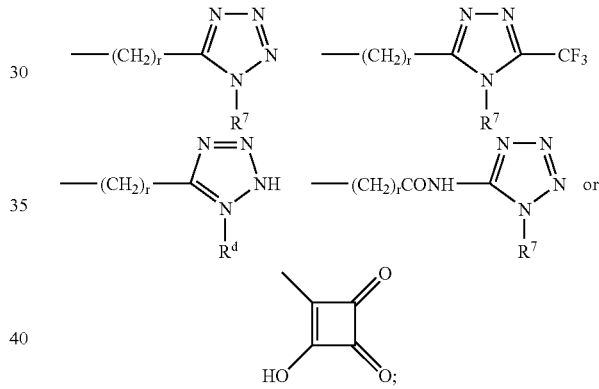

$R^{12a}$ is, independently at each occurrence, H, $C_{1-6}$ alkyl, —(CH₂)$_r$—$C_{3-10}$ carbocycle substituted with 0-3 $R^d$, or —(CH₂)$_r$-5-10 membered heterocycle comprising: carbon atoms and 1-4 heteroatoms selected from N, O, and S(O)$_p$, and substituted with 0-3 $R^d$;

$R^{12b}$ is, independently at each occurrence, $C_{1-6}$ alkyl substituted with 0-2 $R^{12c}$, $C_{2-6}$ alkenyl substituted with 0-2 $R^{12c}$, $C_{2-6}$ alkynyl substituted with 0-2 $R^{12c}$, —(CH₂)$_r$—$C_{3-10}$ carbocycle substituted with 0-3 $R^{12c}$, or —(CH₂)$_r$-5-10 membered heterocycle comprising: carbon atoms and 1-4 heteroatoms selected from N, O, and S(O)$_p$, and substituted with 0-3 $R^{12c}$;

$R^{12c}$ is, independently at each occurrence, H, F, Cl, Br, I, CF₃, OCF₃, CN, NO₂, OR$^a$, —CO₂R$^a$, —NR⁷R⁸, —SO₂R$^c$, $C_{1-6}$ alkyl, $C_{2-6}$ alkenyl, $C_{2-6}$ alkynyl, —(CH₂)$_r$—$C_{3-10}$ carbocycle substituted with 0-3 $R^d$, or —(CH₂)$_r$-5-10 membered heterocycle comprising: carbon atoms and 1-4 heteroatoms selected from N, O, and S(O)$_p$, and substituted with 0-3 $R^d$;

$R^a$ is, independently at each occurrence, H, $C_{1-4}$ alkyl, —(CH₂)$_r$—$C_{3-7}$ cycloalkyl, —(CH₂)$_r$—$C_{6-10}$ aryl, or —(CH₂)$_r$-5-10 membered heteroaryl, wherein said aryl or heteroaryl groups are optionally substituted with 0-2 $R^f$;

$R^b$ is, independently at each occurrence, CF₃, OH, $C_{1-4}$ alkoxy, $C_{1-6}$ alkyl, —(CH₂)$_r$—$C_3 I_0$ carbocycle substituted with 0-2 $R^d$, or —$(CH_2)_r$-5-10 membered heterocycle comprising: carbon atoms and 1-4 heteroatoms selected from N, O, and $S(O)_p$ and substituted with 0-2 $R^d$;

$R^c$ is, independently at each occurrence, CA4 alkyl, $C_{6-10}$ aryl, a 5- to 10-membered heteroaryl, $(C_6 I_0$ aryl)-$C_{1-4}$ alkyl, or (5-10 membered heteroaryl)-$C_{1-4}$ alkyl, wherein said aryl and heteroaryl groups are substituted with 0-2 $R^d$;

$R^d$ is, independently at each occurrence, H, =O, $OR^a$, F, Cl, Br, I, CN, $NO_2$, —$NR^7R^8$, —$C(O)R^a$, —$CO_2R^a$, —$NR^8C(O)R^a$, —$CONR^{7a}R^8$, —$SO_2NR^8R^{10}$, —$NR^8SO_2NR^8R^{10}$, —$NR_{10}SO_2$—$C_{1-4}$ alkyl, —$NR^{10}SO_2CF_3$, —$NR^{10}SO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl substituted with 0-2 $R^e$, $C_{2-6}$ alkenyl substituted with 0-2 $R^e$, or $C_{2-6}$ alkynyl substituted with 0-2 $R^e$;

$R^e$ is, independently at each occurrence, =O, $OR^a$, F, Cl, Br, I, CN, $NO_2$, —$NR^8R^9$, —$C(O)R^a$, —$CO_2R^a$, —$NR^8C(O)R^a$, —$CONR^{7a}R^8$, —$SO_2NR^8R^9$, —$NR^8SO_2NR^8R^9$, —$NR_8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, or —$(CF_2)_rCF_3$;

$R^f$ is, independently at each occurrence, H, =O, —$(CH_2)_r$ $OR^9$, F, Cl, Br, I, CN, $NO_2$, —$NR^8R^9$, —$C(O)R^g$, —$CO_2R^g$, —$NR^8C(O)R^g$, —$CONR^8R^9$, —$SO_2NR^8R^9$, —$NR^8SO_2NR^8R^9$, —$NR^8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl, $C_{2-6}$ alkenyl, or $C_{2-6}$ alkynyl;

$R^g$ is, independently at each occurrence, H, $C_{1-6}$ alkyl, or —$(CH_2)_n$-phenyl;

n, at each occurrence, is selected from 0, 1, 2, 3, and 4;

p, at each occurrence, is selected from 0, 1, and 2; and r, at each occurrence, is selected from 0, 1, 2, 3, and 4.

In a second aspect, the present invention includes compounds of Formula (Ia):

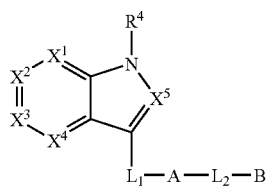

(Ia)

or stereoisomers or pharmaceutically acceptable salts, solvates, or prodrugs thereof, wherein:

$L_1$ is —$CH_2$—, —$CH_2CH_2$—, —$NR^7$—, —$C(O)$—, —$S(O)_p$—, —$(CH_2)$ $C(O)$—, —$C(O)(CH_2)$—, —$(CH_2)$ $O$—, —$O(CH_2)$—, —$(CH_2)NR^7$—, —$NR^7(CH_2)$—, —$(CH_2)S(O)_p$—, —$S(O)_p(CH_2)$—, —$C(O)NR^8$—, —$NR^8C(O)$—, —$S(O)NR^8$—, —$S(O)_2NR^8$—, —$NR^8S(O)$—, or —$NR^8S(O)_2$—;

$L_2$ is a bond, —$CH_2$—, —$CH_2CH_2$—, —$O$—, —$NR^7$—, —$C(O)$—, —$S(O)_p$—, —$(CH_2)C(O)$—, —$C(O)(CH_2)$—, —$(CH_2)O$—, —$O(CH_2)$—, —$(CH_2)NR^7$—, —$NR^7(CH_2)$—, —$(CH_2)S(O)_p$—, —$S(O)_p(CH_2)$—, —$C(O)O$—, —$OC(O)$—, —$C(O)NR^{10}$—, —$NR^{10}C(O)$—, —$S(O)NR^{10}$—, —$S(O)_2NR^{10}$—, —$NR^{10}S(O)$—, or —$NR^{10}S(O)_2$—;

A is phenylene substituted with 0-2 $R^{11}$ and 0-1 $R^{12}$, or a 5-6 membered heteroaryl other than thiazolyl, comprising: carbon atoms and 1-4 heteroatoms selected from N, O, and S, and substituted 0-2 $R^{11}$ and 0-1 $R^{12}$, provided that the groups $L_1$ and $L_2$ are attached to said phenylene or heteroaryl in a 1,2- or 1,3-orientation;

B is phenyl substituted with 0-2 $R^{11}$ and 0-1 $R^{12}$, or a 5-12 membered heterocycle comprising: carbon atoms and 1-4 heteroatoms selected from N, O, and $S(O)_p$, and substituted with 0-2 $R^{11}$ and 0-1 $R^{12}$;

$X^1$, $X^2$, $X^3$ and $X^4$ independently represent $CR^1$, $CR^2$ or N; $X^5$ is CH or N;

$R^1$ is H, —$NH_2$, —$NH(C_{1-3}$ alkyl), —$N(C_{1-3}$ alkyl)$_2$, —$C(=NH)NH_2$, —$C(=NOH)NH_2$, —$CONH_2$, —$CH_2NH_2$, —$CH_2NH(C_{1-3}$ alkyl), —$CH_2N(C_{1-3}$ alkyl)$_2$, —$CH_2CH_2NH_2$, —$CH_2CH_2NH(C_{1-3}$ alkyl), —$CH_2CH_2N(C_{1-3}$ alkyl)$_2$, —$C(=NR^{8a})NR^7R^9$, —$C(=NR^{8a})NR^{8a}R^9$, —$NHC(=NR^{8a})NR^7R^9$, —$NR^8CH(=NR^{8a})$, —$NR^7R^8$, —$CONR^{7a}R^8$, —$S(O)_pNR^8R^9$, F, Cl, Br, I, $OCF_3$, $CF_3$, $OR^a$, $SR^a$, CN or $C_{1-6}$ alkyl substituted with 1 $R^{1a}$;

$R^{1a}$ is H, —$C(=NR^{8a})NR^7R^9$, —$NHC(=NR^{8a})NR^7R^9$, —$ONHC(=NR^{8a})NR^7R^9$, —$NR^8CH(=NR^{8a})$, —$NR^7R^8$, —$CONR^{7a}R^8$, F, Cl, Br, I, $OCF_3$, $CF_3$, $OR^a$, $SR^a$, or CN;

$R^2$ is H, F, Cl, $OR^a$, CN, —$NR^7R^8$, —$CONR^{7a}R^8$, —$NR^{10}C(O)R^b$, —$S(O)_pNR^8R^9$, —$S(O)R^c$, —$S(O)_2R^c$, $C_{1-6}$ alkyl substituted with 0-2 $R^{2a}$, —$(CH_2)_r$—$C_3$-$C_7$ carbocycle substituted with 0-2 $R^{2b}$, or —$(CH_2)_r$-5-7 membered heterocycle comprising: carbon atoms and 1-4 heteroatoms selected from N, O, and $S(O)_p$, and substituted with 0-2 $R^{2b}$;

$R^{2a}$ is, independently at each occurrence, H, F, $OCF_3$, $CF_3$, $OR^a$, $SR^a$, CN, —$NR^7R^8$, —$CONR^{7a}R^8$, —$NR^{10}C(O)R^b$, —$S(O)_pNR^8R^9$, —$S(O)R^c$, or —$S(O)_2R^c$;

$R^{2b}$ is, independently at each occurrence, H, F, $OR^a$, $SR^a$, CN, $NO_2$, $CF_3$, —$SO_2R^c$, —$NR^7R^8$, $C_{1-6}$ alkyl, $C_{2-6}$ alkenyl, $C_{2-6}$ alkynyl, $C_{3-6}$ cycloalkyl, $C_{1-4}$ haloalkyl, $C_{1-4}$ haloalkyloxy-, $C_{1-4}$ alkyloxy-, $C_{1-4}$ alkylthio-, $C_{1-4}$ alkyl-CO—, or $C_{1-4}$ alkyl-CONH—;

alternately, when $R^1$ and $R^2$ are substituted on adjacent carbon ring atoms, they can be taken together with the carbon ring atoms to which they are attached to form a 5-7 membered carbocycle or heterocycle substituted with 0-2 $R^{2b}$;

$R^4$ is H, $C_{1-6}$ alkyl substituted with 0-1 $R^{4a}$, $C_{2-6}$ alkenyl substituted with 0-1 $R^{4a}$, $C_{2-6}$ alkynyl substituted with 0-1 $R^{4a}$, —$(CH_2)_r$—$CONR^{7a}R^8$, ($C_{1-6}$ alkyl)-CO—, ($C_{3-6}$ cycloalkyl)$C_{1-3}$ alkyl-CO—, ($C_{3-6}$ cycloalkyl)-CO—, phenyl-CO—, benzyl-CO—, benzyl-$S(O)_2$—, —$(CH_2)_r$—$C_{3-7}$ carbocycle substituted with 0-3 $R^{4b}$, or —$(CH_2)_r$-5-6 membered heteroaryl comprising: carbon atoms and 1-4 heteroatoms selected from N, O, and $S(O)_p$, and substituted with 0-3 $R^{4b}$;

$R^{4a}$ is, independently at each occurrence, H, $C_{1-4}$ alkyl, $OR^a$, F, =O, $CF_3$, CN, $NO_2$, —$C(O)R^a$, —$CO_2R^a$, —$CONR^1OR^8$, —$NR^{10}COR^a$, —$NR^{10}C(O)OR^c$, —$NR^{10}SO_2R^c$, or —$S(O)_pR^c$;

$R^{4b}$ is, independently at each occurrence, H, =O, $OR^a$, F, Cl, Br, I, CN, $NO_2$, —$NR^7R^8$, —$C(O)R^a$, —$CO_2R^a$, —$NR^8C(O)R^a$, —$CONR^{7a}R^8$, —$SO_2NR^8R^9$, —$NR^8SO_2NR^8R^9$, —$NR_8SO_2$—$C_{1-4}$ alkyl, —$NR^8SO_2CF_3$, —$NR^8SO_2$-phenyl, —$S(O)_2CF_3$, —$S(O)_p$—$C_{1-4}$ alkyl, —$S(O)_p$-phenyl, —$(CF_2)_rCF_3$, $C_{1-6}$ alkyl substituted with 0-2 $R^e$, $C_{2-6}$ alkenyl substituted with 0-2 $R^e$, or $C_{2-6}$ alkynyl substituted with 0-2 $R^e$;

$R^7$ is, independently at each occurrence, H, $C_{1-6}$ alkyl, —$(CH_2)_n$-phenyl, ($C_{1-6}$ alkyl)-CO—, ($C_{6-10}$ aryl)-($C_{0-4}$ alkyl)-CO—, (5-10 membered heteroaryl)-$C_{0-4}$ alkyl-CO—, ($C_{1-4}$ alkyl)OC(O)—, ($C_{6-10}$ aryl)-$CH_2$—OC(O)—, ($C_{1-4}$ alkyl)-C(O)O—($C_{1-4}$ alkyl)-OC(O)—, ($C_{6-10}$ aryl)-C(O)O—($C_{1-4}$ alkyl)-OC(O)—, (5-10 membered heteroaryl)-$CH_2$—OC(O)—, ($C_{1-6}$ alkyl)-NHC(O)—, ($C_{6-10}$ aryl)-NHC(O)—, (5-10 membered heteroaryl)-NHC(O)—, ($C_{1-6}$ alkyl)-S (O)$_2$—, (C$_{6-10}$ aryl)-(C$_{0-4}$ alkyl)-S(O)$_2$—, or (5-10 membered heteroaryl)-S(O)$_2$—; wherein said phenyl, aryl and heteroaryl are substituted with 0-2 R$^f$;

R$^{7a}$ is, independently at each occurrence, H, C$_{1-4}$ alkyl substituted with 0-2 R$^{7b}$ and/or 0-2 R$^{7c}$, —(CH$_2$)$_r$—C$_{3-10}$ carbocycle substituted with 0-3 R$^f$, or a —(CH$_2$)$_r$-5-12 membered heterocycle comprising: carbon atoms and 1-4 heteroatoms selected from N, O, and S(O)$_p$, and substituted 0-3 R$^f$;

R$^{7b}$ is, independently at each occurrence, =O, OR$^g$, F, CN, NO$_2$, —NR$^7$R$^8$, —C(O)R$^g$, —CO$_2$R$^g$, —NR$^8$C(O)R$^g$, —CONR$^8$R$^9$, —NR$^8$C(O)NR$^8$R$^9$, —SO$_2$NR$^8$R$^9$, —NR$^8$SO$_2$NR$^8$R$^9$, —NR$^8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

R$^{7c}$ is, independently at each occurrence, C$_{3-10}$ carbocycle substituted with 0-3 R$^f$; or a 5-12 membered heterocycle comprising: carbon atoms and 1-4 heteroatoms selected from N, O, and S(O)$_p$, and substituted 0-3 R$^f$;

R$^8$ is, independently at each occurrence, H, C$_{1-6}$ alkyl, or —(CH$_2$)$_n$-phenyl;

R$^{8a}$ is, independently at each occurrence, H, OH, C$_{1-6}$ alkyl, C$_{1-4}$ alkoxy, (C$_{6-10}$ aryl)-C$_{1-4}$ alkoxy, —(CH$_2$)$_n$-phenyl, (C$_{1-6}$ alkyl)-CO—, (C$_{6-10}$ aryl)-C$_{1-4}$ alkyl-CO—, (C$_{3-6}$ cycloalkyl)-C$_{0-4}$ alkyl-CO—, (5-10 membered heteroaryl)-C$_{0-4}$ alkyl-CO—, (C$_{1-6}$ alkyl)OC(O)—, (C$_{6-10}$ aryl)-C$_{1-4}$ alkyl-OC(O)—, (C$_{1-4}$ alkyl)-C(O)O—(C$_{1-4}$ alkyl)-OC(O)—, (C$_{1-6}$ alkyl)C(O)O—, or (C$_{6-10}$ aryl)-(C$_{0-4}$ alkyl)-C(O)O—; wherein said phenyl, aryl and heteroaryl are substituted with 0-2 R$^f$;

alternatively, R$^7$ and R$^8$, or R$^{7a}$ and R$^8$, when attached to the same nitrogen, combine to form a 5-10 membered heterocyclic ring comprising: carbon atoms and 0-2 additional heteroatoms selected from N, O, and S(O)$_p$, and optionally substituted with 0-2 R$^d$;

R$^9$ is, independently at each occurrence, H, C$_{1-6}$ alkyl, or —(CH$_2$)$_n$-phenyl;

R$^{10}$ is, independently at each occurrence, H, C$_{1-6}$ alkyl substituted with 0-2 R$^{10a}$, C$_{2-6}$ alkenyl substituted with 0-2 R$^{10a}$, C$_{2-6}$ alkynyl substituted with 0-2 R$^{10a}$, —(CH$_2$)$_r$—C$_{3-10}$ carbocycle substituted with 0-3 R$^{10b}$, or —(CH$_2$)$_r$-5-10 membered heterocycle comprising: carbon atoms and 1-4 heteroatoms selected from N, O, and S(O)$_p$, and substituted with 0-3 R$^{10b}$;

R$^{10a}$ is, independently at each occurrence, H, C$_{1-4}$ alkyl, OR$^a$, F, =O, CF$_3$, CN, NO$_2$, —C(O)R$^a$, —CO$_2$R$^a$, —CONR$^{7a}$R$^8$, or —S(O)$_p$R$^c$;

R$^{10b}$ is, independently at each occurrence, H, =O, OR$^a$, F, Cl, Br, I, CN, NO$_2$, —NR$^7$R$^8$, —C(O)R$^a$, —CO$_2$R$^a$, —NR$^8$C(O)R$^a$, —CONR$^{7a}$R$^8$, —SO$_2$NR$^8$R$^9$, —NR$^8$SO$_2$NR$^8$R$^9$, —NR$_8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-4}$ alkyl substituted with 0-2 R$^e$, C$_{2-4}$ alkenyl substituted with 0-2 R$^e$, or C$_{2-4}$ alkynyl substituted with 0-2 R$^e$;

R$^{11}$ is, independently at each occurrence, H, =O, —(CH$_2$)$_r$—OR$^a$, F, Cl, Br, CF$_3$, CN, NO$_2$, —(CH$_2$)$_r$—NR$^7$R$^8$, —(CH$_2$)$_r$—C(=NR$^8$)NR$^7$R$^9$, —C(O)R$^a$, —CO$_2$R$^a$, —(CH$_2$)$_r$—NR$^8$C(O)R$^a$, —NR$^8$C(O)OR$^c$, —CONR$^{7a}$R$^8$, —NR$^8$C(O)NR$^8$R$^{10}$, —SO$_2$NR$^8$R$^{10}$, —NR$^8$SO$_2$NR$^8$R$^{10}$, —NR$_8$SO$_2$—C$_{1-4}$ alkyl, —NR$^8$SO$_2$CF$_3$, —NR$^8$SO$_2$-phenyl, —S(O)$_2$CF$_3$, —S(O)$_p$—C$_{1-4}$ alkyl, —S(O)$_p$-phenyl, —(CF$_2$)$_r$CF$_3$, C$_{1-6}$ alkyl substituted with 0-2 R$^{11a}$, C$_{2-6}$ alkenyl substituted with 0-2 R$^{11a}$, C$_{2-6}$ alkynyl substituted with 0-2 R$^{11a}$, C$_{1-6}$ alkyl substituted with 0-2 R$^{11b}$, C$_{2-6}$ alkenyl substituted with 0-2 R$^{11b}$, C$_{2-6}$ alkynyl substituted with 0-2 R$^{11b}$, phenyl substituted with 0-3 R$^c$ and/or 0-3 R$^d$, or a 5-7 membered heterocycle comprising: carbon atoms and 1-4 heteroatoms selected from N, O, and S(O)$_p$, and substituted with 0-3 R$^c$ and/or 0-3 R$^d$;

R$^{11a}$ is, independently at each occurrence, =O, OR$^a$, F, Cl, Br, I, CN, NO$_2$, —NR$^7$R$^8$, —C(O)R$^a$, —CO$_2$R$^a$, —NR$^8$C(O)R$^c$, —CONR$^{7a}$R$^8$, —NR$^8$C(O)NR$^8$R$^{10}$, —SO$_2$NR$^8$R$^{10}$, —NR$^8$SO$_2$NR$^8$R$^{10}$, —NR$^{10}$SO$_2$—C$_{1-4}$ alkyl, —NR$^{10}$SO$_2$CF$_3$, —NR$^{10}$SO$_2$-phenyl, —S(O)$_2$CF$_3$, —S(O)$_p$—C$_{1-4}$ alkyl, —S(O)$_p$-phenyl, or —(CF$_2$)$_r$CF$_3$;

R$^{11b}$ is, independently at each occurrence, C$_{3-10}$ carbocycle substituted with 0-3 R$^d$, or a 5-12 membered heterocycle comprising: carbon atoms and 1-4 heteroatoms selected from N, O, and S(O)$_p$, and substituted 0-3 R$^d$;

R$^{12}$ is, independently at each occurrence, OR$^{12a}$, —CH$_2$OR$^{12a}$, —C(O)NR$^{7a}$R$^8$, —(CH$_2$)$_r$CO$_2$R$^{12a}$, —(CH$_2$)$_r$SO$_3$H, —OSO$_3$H, —(CH$_2$)$_r$PO$_3$H, —OPO$_3$H$_2$, —PO$_3$H$_2$, —NHCOCF$_3$, —NHSO$_2$CF$_3$, —CONHNHSO$_2$CF$_3$, —C(CF$_3$)$_2$OH, —SO$_2$NHR$^{12a}$, —CONHSO$_2$NHR$^{12a}$, —SO$_2$NHCOR$^{12a}$, —SO$_2$NHCO$_2$R$^{12a}$, —CONHSO$_2$R$^{12b}$, —NHSO$_2$R$^{12b}$, —CONHOR$^{12b}$,

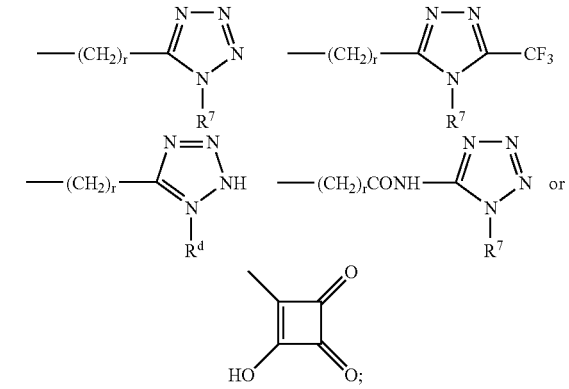

R$^{12a}$ is, independently at each occurrence, H, C$_{1-6}$ alkyl, —(CH$_2$)$_r$—C$_{3-10}$ carbocycle substituted with 0-3 R$^d$, or —(CH$_2$)$_r$-5-10 membered heterocycle comprising: carbon atoms and 1-4 heteroatoms selected from N, O, and S(O)$_p$, and substituted with 0-3 R$^d$;

R$^{12b}$ is, independently at each occurrence, C$_1$-C$_6$ alkyl substituted with 0-2 R$^{12c}$ C$_2$-C$_6$ alkenyl substituted with 0-2 R$^{2c}$ C$_2$-C$_6$ alkynyl substituted with 0-2 R$^{12c}$, —(CH$_2$)$_r$—C$_3$-C$_{10}$ carbocycle substituted with 0-3 R$^{12c}$, or —(CH$_2$)$_r$-5-10 membered heterocycle comprising: carbon atoms and 1-4 heteroatoms selected from N, O, and S(O)$_p$, and substituted with 0-3 R$^{12c}$;

R$^{12c}$ is, independently at each occurrence, H, F, Cl, Br, I, CF$_3$, OCF$_3$, CN, NO$_2$, OR$^a$, —CO$_2$R$^a$, —NR$^7$R$^8$, —SO$_2$R$^c$, C$_1$-C$_6$ alkyl, C$_2$-C$_6$ alkenyl, C$_2$-C$_6$ alkynyl, —(CH$_2$)$_r$—C$_{3-10}$ carbocycle substituted with 0-3 R$^d$, or —(CH$_2$)$_r$-5-10 membered heterocycle comprising: carbon atoms and 1-4 heteroatoms selected from N, O, and S(O)$_p$, and substituted with 0-3 R$^d$;

R$^a$ is, independently at each occurrence, H, C$_{1-4}$ alkyl, —(CH$_2$)$_r$—C$_{3-7}$ cycloalkyl, —(CH$_2$)$_r$—C$_{6-10}$ aryl, or —(CH$_2$)$_r$-5-10 membered heteroaryl, wherein said aryl or heteroaryl groups are optionally substituted with 0-2 R$^f$;

R$^b$ is, independently at each occurrence, CF$_3$, OH, C$_{1-4}$ alkoxy, C$_{1-6}$ alkyl, —(CH$_2$)$_r$—C$_{3-10}$ carbocycle substituted with 0-2 R$^d$, or —(CH$_2$)$_r$-5-10 membered heterocycle comprising: carbon atoms and 1-4 heteroatoms selected from N, O, and S(O)$_p$ and substituted with 0-2 R$^d$;

$R^c$ is, independently at each occurrence, $C_{1-4}$ alkyl, $C_{6-10}$ aryl, 5-10 membered heteroaryl, ($C_{6-10}$ aryl)-$C_{1-4}$ alkyl, or (5-10 membered heteroaryl)-$C_{1-4}$ alkyl, wherein said aryl and heteroaryl groups are substituted with 0-2 $R^d$;

$R^d$ is, independently at each occurrence, H, =O, $OR^a$, F, Cl, Br, I, CN, $NO_2$, $-NR^7R^8$, $-C(O)R^a$, $-CO_2R^a$, $-NR^8C(O)R^a$, $-CONR^{7a}R^8$, $-SO_2NR^8R^{11}$, $-NR^8SO_2NR^8R^{10}$, $-NR^{10}SO_2-C_{1-4}$ alkyl, $-NR^{10}SO_2CF_3$, $-NR^{10}SO_2$-phenyl, $-S(O)_2CF_3$, $-S(O)_p-C_{1-4}$ alkyl, $-S(O)_p$-phenyl, $-(CF_2)_rCF_3$, $C_{1-6}$ alkyl substituted with 0-2 $R^e$, $C_{2-6}$ alkenyl substituted with 0-2 $R^e$, or $C_{2-6}$ alkynyl substituted with 0-2 $R^e$;

$R^e$ is, independently at each occurrence, =O, $OR^a$, F, Cl, Br, I, CN, $NO_2$, $-NR^8R^9$, $-C(O)R^a$, $-CO_2R^a$, $-NR^8C(O)R^a$, $-CONR^{7a}R^8$, $-SO_2NR^8R^9$, $-NR^8SO_2NR^8R^9$, $-NR^8SO_2-C_{1-4}$ alkyl, $-NR^8SO_2CF_3$, $-NR^8SO_2$-phenyl, $-S(O)_2CF_3$, $-S(O)_p-C_{1-4}$ alkyl, $-S(O)_p$-phenyl, or $-(CF_2)_rCF_3$;

$R^f$ is, independently at each occurrence, H, =O, $-(CH)_rOR^9$, F, Cl, Br, I, CN, $NO_2$, $-NR^8R^9$, $-C(O)R^g$, $-CO_2R^g$, $-NR^8C(O)R^g$, $-CONR^8R^9$, $-SO_2NR^8R^9$, $-NR^8SO_2NR^8R^9$, $-NR^8SO_2-C_{1-4}$ alkyl, $-NR^8SO_2CF_3$, $-NR^8SO_2$-phenyl, $-S(O)_2CF_3$, $-S(O)_p-C_{1-4}$ alkyl, $-S(O)_p$-phenyl, $-(CF_2)_rCF_3$, $C_{1-6}$ alkyl, $C_{2-6}$ alkenyl, or $C_{2-6}$ alkynyl;

$R^g$ is, independently at each occurrence, H, $C_{1-6}$ alkyl, or $-(CH_2)_n$-phenyl;

n, at each occurrence, is selected from 0, 1, 2, 3, and 4;

p, at each occurrence, is selected from 0, 1, and 2; and r, at each occurrence, is selected from 0, 1, 2, 3, and 4.

In a third aspect, the present invention includes compounds of Formula (Ib):

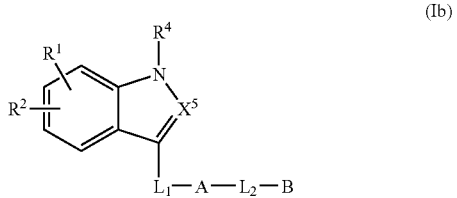

(Ib)

or stereoisomers or pharmaceutically acceptable salts, solvates, or prodrugs thereof, wherein: A, B, $L_1$, $L_2$, $X^5$, $R^1$, $R^2$ and $R^4$ are as defined in the second aspect.

In a fourth aspect, the present invention includes compounds of Formula (Ic):

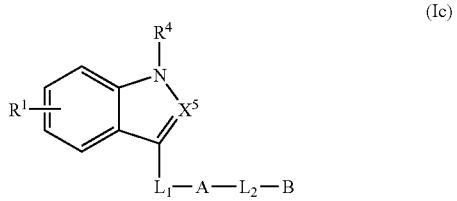

(Ic)

or stereoisomers or pharmaceutically acceptable salts, solvates, or prodrugs thereof, wherein:

$L_1$ is $-CH_2-$, $-CH_2CH_2-$, $-NH-$, $-(CH_2)O-$, $-O(CH_2)-$, $-(CH_2)NH-$, $-NH(CH_2)-$, $-CONH-$, or $-NHCO-$;

$L_2$ is a bond, $-CH_2-$, $-CH_2CH_2-$, $-O-$, $-NH-$, $-(CH_2)O-$, $-O(CH_2)-$, $-(CH_2)NH-$, $-NH(CH_2)-$, $-CONH-$, or $-NHCO-$;

A is phenylene substituted with 0-2 $R^{11}$, or pyridylene substituted with 0-2 $R^{11}$; provided that the groups $L_1$ and $L_2$ are attached to said phenylene or heteroaryl in a ortho- or meta-orientation;

B is phenyl substituted with 0-2 $R^{11}$ and 0-1 $R^{12}$, a 5- to 6-membered heterocycle substituted with 0-2 $R^{11}$ and 0-1 $R^{12}$ and selected from: pyrrolidinyl, pyrrolyl, pyrrolinyl, pyrazolyl, oxazolyl, imidazolyl, imidazolinyl, pyrazolyl, pyrazolinyl, isoxazolyl, isothiazolyl, triazolyl, tetrazolyl, pyranyl, piperidyl, piperazinyl, pyridyl, pyrimidinyl, pyrazinyl, and triazinyl;

$X^5$ is CH or N;

$R^1$ is $-C(=NH)NH_2$, $-C(=NOH)NH_2$, $-CONH_2$, $-CH_2NH_2$, or $-C(O)NR^{7a}R^8$;

$R^4$ is H, $-(CH_2)_r-CONR^{7a}R^8$, $C_{1-4}$ alkyl, $-(CH_2)_r-C_{3-7}$ cycloalkyl, $-(CH_2)_r$-phenyl, or $-(CH_2)_r$-5- to 6-membered heteroaryl selected from: pyrrolyl, pyrazolyl, oxazolyl, thiazolyl, imidazolyl, isoxazolyl, isothiazolyl, triazolyl, tetrazolyl, pyridazinyl, pyridyl, pyrimidinyl, pyrazinyl, and triazinyl;

$R^7$ is, independently at each occurrence, H, $C_{1-6}$ alkyl, or benzyl;

$R^{7a}$ is, independently at each occurrence, H, $C_{1-4}$ alkyl substituted with 0-1 $R^{7b}$ or 0-1 $R^{7c}$, $C_{3-7}$ cycloalkyl substituted with 0-2 $R^f$, phenyl substituted with 0-3 $R^f$, or a 5-6 membered heterocycle comprising: carbon atoms and 1-4 heteroatoms selected from N, O, and $S(O)_p$, and substituted 0-3 $R^f$;

$R^{7b}$ is =O, $OR^g$, F, Cl, Br, I, CN, $NO_2$, $-NR^7R^8$, $-C(O)R^g$, $-CO_2R^g$, $-NR^8C(O)R^g$, $-CONR^8R^9$, $-NR^8C(O)NR^8R^9$, $-SO_2NR^8R^9$, $-NR^8SO_2NR^8R^9$, $-NR^8SO_2-C_{1-4}$ alkyl, $-NR^8SO_2CF_3$, $-NR^8SO_2$-phenyl, $-S(O)_2CF_3$, $-S(O)_p-C_{1-4}$ alkyl, $-S(O)_p$-phenyl, or $-(CF_2)_rCF_3$;

$R^{7c}$ is $C_{3-0}$ carbocycle substituted with 0-3 $R^f$; or a 5-12 membered heterocycle comprising: carbon atoms and 1-4 heteroatoms selected from N, O, and $S(O)_p$, and substituted 0-3 $R^f$;

$R^8$ is, independently at each occurrence, H, $C_{1-6}$ alkyl, or benzyl;

$R^9$ is, independently at each occurrence, H, $C_{1-6}$ alkyl, or benzyl;

$R^{10}$ is, independently at each occurrence, H, $C_{1-6}$ alkyl substituted with 0-2 $R^{10a}$, $C_{2-6}$ alkenyl substituted with 0-2 $R^{10a}$, $C_{2-6}$ alkynyl substituted with 0-2 $R^{10a}$, $-(CH_2)_r-C_{3-10}$ carbocycle substituted with 0-3 $R^{10b}$, or $-(CH_2)_r$-5-10 membered heterocycle comprising: carbon atoms and 1-4 heteroatoms selected from N, O, and $S(O)_p$, and substituted with 0-3 $R^{10b}$;

$R^{10a}$ is, independently at each occurrence, H, $C_{1-4}$ alkyl, $OR^a$, F, =O, $CF_3$, CN, $NO_2$, $-C(O)R^a$, $-CO_2R^a$, $-CONR^{7a}R^8$, or $-S(O)_pR^c$;

$R^{10b}$ is, independently at each occurrence, H, =O, $OR^a$, F, Cl, Br, I, CN, $NO_2$, $-NR^7R^8$, $-C(O)R^a$, $-CO_2R^a$, $-NR^8C(O)R^a$, $-CONR^{7a}R^8$, $-SO_2NR^8R^9$, $-NR^8SO_2NR^8R^9$, $-NR^8SO_2-C_{1-4}$ alkyl, $-NR^8SO_2CF_3$, $-NR^8SO_2$-phenyl, $-S(O)_2CF_3$, $-S(O)_p-C_{1-4}$ alkyl, $-S(O)_p$-phenyl, $-(CF_2)_rCF_3$, $C_{1-4}$ alkyl substituted with 0-2 $R^e$, $C_{2-4}$ alkenyl substituted with 0-2 $R^e$, or $C_{2-4}$ alkynyl substituted with 0-2 $R^e$;

$R^{11}$ is, independently at each occurrence, H, F, Cl, $CF_3$, $C_{1-6}$ alkyl, $-(CH_2)_r-OR^a$, CN, $-(CH_2)_r-NR^7R^8$, $-(CH_2)_r-C(=NR^8)NR^7R^9$, $-C(O)R^a$, $-CO_2R^a$, —(CH₂)ᵣ—NR⁸C(O)Rᵃ, —NR⁸C(O)ORᶜ, —CONR⁷ᵃR⁸, —NR⁸C(O)NR⁸R¹⁰, —SO₂NR⁸R¹⁰, —NR⁸SO₂NR⁸R¹⁰, or —NR₈SO₂—C₁₋₄ alkyl;

R¹² is —CONR⁷ᵃR⁸, —(CH₂)ᵣCO₂R¹²ᵃ, —CH₂OR¹²ᵃ, —SO₂NHR¹²ᵃ, —SO₂NHCOR¹²ᵃ, —SO₂NHCO₂R¹²ᵃ, —CONHSO₂R¹²ᵇ, —NHSO₂R¹²ᵇ, or —(CH₂)ᵣ-5-tetrazolyl;

R¹²ᵃ is, independently at each occurrence, H or C₁₋₆ alkyl;

R¹²ᵇ is, independently at each occurrence, C₁-C₄ alkyl substituted with 0-1 R¹²ᶜ, C₂-C₄ alkenyl substituted with 0-1 R¹²ᶜ, C₂-C₄ alkynyl substituted with 0-1 R¹²ᶜ, —(CH₂)ᵣ—C₃-C₇ carbocycle substituted with 0-2 R¹²ᶜ, or —(CH₂)ᵣ-5-6 membered heterocycle comprising: carbon atoms and 1-4 heteroatoms selected from N, O, and S(O)ₚ, and substituted with 0-2 R¹²ᶜ;

R¹²ᶜ is, independently at each occurrence, H, F, Cl, Br, I, CF₃, OCF₃, CN, NO₂, ORᵃ, —CO₂Rᵃ, —NR⁷R⁸, —SO₂Rᶜ, C₁-C₆ alkyl, C₂-C₆ alkenyl, C₂-C₆ alkynyl, —(CH₂)ᵣ—C₃₋₁₀ carbocycle substituted with 0-3 Rᵈ; or —(CH₂)ᵣ-5-10 membered heterocycle comprising: carbon atoms and 1-4 heteroatoms selected from N, O, and S(O)ₚ, and substituted with 0-3 Rᵈ;

Rᵃ is, independently at each occurrence, H, C₁₋₄ alkyl, —(CH₂)ᵣ—C₃₋₇ cycloalkyl, —(CH₂)ᵣ—C₆₋₁₀ aryl, or —(CH₂)ᵣ-5-10 membered heteroaryl, wherein said aryl or heteroaryl groups are optionally substituted with 0-2 Rᶠ;

Rᶜ is, independently at each occurrence, C₁₋₄ alkyl, phenyl or benzyl;

Rᵈ is, independently at each occurrence, H, =O, ORᵃ, F, Cl, Br, I, CN, NO₂, —NR⁷R⁸, —C(O)Rᵃ, —CO₂Rᵃ, —NR⁸C(O)Rᵃ, —CONR⁷ᵃR⁸, —SO₂NR⁸R¹⁰, —NR⁸SO₂NR⁸R¹⁰, —NR₁₀SO₂—C₁₋₄ alkyl, —NR¹⁰SO₂CF₃, —NR¹⁰SO₂-phenyl, —S(O)₂CF₃, —S(O)ₚ—C₁₋₄ alkyl, —S(O)ₚ-phenyl, —(CF₂)ᵣCF₃, C₁₋₆ alkyl substituted with 0-2 Rᵉ, C₂₋₆ alkenyl substituted with 0-2 Rᵉ, or C₂₋₆ alkynyl substituted with 0-2 Rᵉ;

Rᵉ is, independently at each occurrence, =O, ORᵃ, F, Cl, Br, I, CN, NO₂, —NR⁸R⁹, —C(O)Rᵃ, —CO₂Rᵃ, —NR⁸C(O)Rᵃ, —CONR⁷ᵃR⁸, —SO₂NR⁸R⁹, —NR⁸SO₂NR⁸R⁹, —NR₈SO₂—C₁₋₄ alkyl, —NR⁸SO₂CF₃, —NR⁸SO₂-phenyl, —S(O)₂CF₃, —S(O)ₚ—C₁₋₄ alkyl, —S(O)ₚ-phenyl, or —(CF₂)ᵣCF₃;

Rᶠ is, independently at each occurrence, H, =O, —(CH₂)ᵣ—OR⁹, F, Cl, Br, CF₃, CN, NO₂, —NR⁸R⁹, —C(O)Rᵍ, —C(O)ORᵍ, —NR⁸C(O)Rᵍ, —C(O)NR⁸R⁹, —SO₂NR⁸R⁹, —NR₈SO₂—C₁₋₄ alkyl, —NR⁸SO₂CF₃, —S(O)₂CF₃, —S(O)ₚ—C₁₋₄ alkyl, C₁-C₆ alkyl, C₂-C₆ alkenyl, or C₂-C₆ alkynyl;

Rᵍ is, independently at each occurrence, H or C₁₋₄ alkyl;

p, at each occurrence, is selected from 0, 1, and 2; and r, at each occurrence, is selected from 0, 1, 2, 3, and 4.

In a fifth aspect, the present invention includes compounds of Formula (Ic), within the scope of the fourth aspect wherein:

L₁ is —CH₂—, —CONH—, —CH₂O—, or —CH₂NH—;

L₂ is a bond, —O—, —OCH₂—, —CH₂O—, —CONH—, or —NHCO—;

B is phenyl substituted with 0-2 R¹¹ and 0-1 R¹², pyridyl substituted with 0-2 R¹¹ and 0-1 R¹², pyrrolidinyl substituted with 0-2 R¹¹ and 0-1 R¹², pyrazolyl substituted with 0-2 R¹¹ and 0-1 R¹², or piperidyl substituted with 0-2 R and 0-1 R¹²;

R¹ is —C(=NH)NH₂, —C(=NOH)NH₂, —CONH₂, —CH₂NH₂, H, F, Cl or OMe;

R¹¹ is, independently at each occurrence, H, F, Cl, OH, OMe, CN, Me, Et, Pr, Bu, i-Pr, i-Bu, t-Bu, —NH₂, —CH₂OH, —CO₂H, —CO₂Me, —CO₂Et, —CONH₂, —NHCOMe, —NHCOEt, —NHCOPr, —NHCO(i-Pr), —NHCO(i-Bu), —CONHMe, —CONHEt, —CONHPr, —CONH(i-Bu), —CONHCH₂CONH₂, —CONHCH₂CONHMe, —CONHCH₂CONHEt, —CONH(—CH₂-cyclopropyl), —CONH(—CH₂-cyclohexyl), —CONHBn, —CONH(—CH₂-2-oxazolyl), —CONH(—CH₂-1,2,4-triazolyl), —CONH(—CH₂-2-pyridyl), —CONH(—(CH₂)₂-2-pyridyl), —CONH(—CH₂-3-pyridyl), —CONH(—CH₂-4-pyridyl), —CONH(—CH₂-2-pyrimidinyl), —CONH(—CH₂-3,4,5,6-tetrahydro-2-pyrimidinyl), —CONH(—CH₂-(5-Me-2-pyrazinyl)), —SO₂NH₂, or —CONHSO₂Me; and R¹² is —OH, —OMe, —CH₂OH, —CO₂H, —CH₂(CO₂H), —CO₂Me, —CO₂Et, —SO₂NH₂, or —CONH₂.

In a sixth aspect, the present invention includes compounds of Formula (Id):

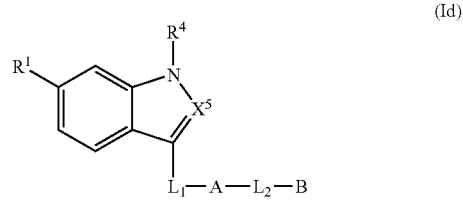

(Id)

or stereoisomers or pharmaceutically acceptable salts, solvates, or prodrugs thereof, wherein:

L₁ is —CH₂—, —CONH—, —CH₂O—, or —CH₂NH—;

L₂ is a bond, —O—, —CH₂O— or —CONH—;

A is 1,2-phenylene, 5-CO₂H-1,2-phenylene, 5-CONHMe-1,2-phenylene, 5-CONHEt-1,2-phenylene, 5-CONHPr-1,2-phenylene, 5-CONHBn-1,2-phenylene, 5-CONHCH₂CONH₂-1,2-phenylene, 5-CONHCH₂CONHMe-1,2-phenylene, 5-CONHCH₂CONHEt-1,2-phenylene, 5-CONH(—CH₂-cyclopropyl)-1,2-phenylene, 5-CONH—(—CH₂-cyclohexyl)-1,2-phenylene, 5-CONH—(—CH₂-(4-COMe-Ph))-1,2-phenylene, 5-CONH(—CH₂-2-oxazolyl)-1,2-phenylene, 5-CONH(—CH₂-1,2,4-triazolyl)-1,2-phenylene, 5-CONH(—CH₂-2-pyridyl)-1,2-phenylene, 5-CONH(—CH₂-3-pyridyl)-1,2-phenylene, 5-CONH(—CH₂-4-pyridyl)-1,2-phenylene, 5-CONH(—CH₂-2-pyrimidinyl)-1,2-phenylene, 5-CONH(—CH₂-3,4,5,6-tetrahydro-2-pyrimidinyl)-1,2-phenylene, 5-CONH(—CH₂-(5-Me-2-pyrazinyl)-1,2-phenylene, 5-CONH(—CH₂-2-thiazolyl)-1,2-phenylene, 5-CONH(—CH₂-4-thiazolyl)-1,2-phenylene, 5-CONH(—CH₂-5-thiazolyl)-1,2-phenylene, 5-CONH(—CH₂-2-imidazolyl)-1,2-phenylene, 5-CONH(—CH₂-4-imidazolyl)-1,2-phenylene, 5-NHCOMe-1,2-phenylene, 5-NHCO(i-Bu)-1,2-phenylene, 1,3-phenylene, 5-NHCOMe-1,3-phenylene, 5-NHCOEt-1,3-phenylene, or 5-NHCOPr-1,3-phenylene, wherein the attachment to L₂ is at carbon 1 of said phenylene groups;

B is 2-CO₂H-phenyl, 2-CO₂Et-phenyl, 2-CONH₂-phenyl, 2-CONHSO₂Me-phenyl, 2-SO₂NH₂-phenyl, 2-CH₂OH-4-OMe-phenyl, 2-CO₂H-3-Me-phenyl, 2-CO₂H-4-Me-phenyl, 2-CO₂H-5-Me-phenyl, 2-CO₂Et-4-Me-phenyl, 2-CO₂H-4-Cl-phenyl, 2-CO₂Et-4-Cl-phenyl, 2-CO₂H-4-OMe-phenyl, 2-CO₂Et-4-OMe-phenyl, 2-CO₂H-4-CONH₂-phenyl, 2-CO₂H-4,5-methylenedioxyphenyl, 3-CO₂H-6-Me-2-pyridyl, 3-CO₂H-5-Cl-2-pyridyl, 2-CO₂H-1-pyrrolidinyl, 2-CO₂Et-1-pyrrolidinyl, 1-Me-3-CO₂H-4-pyrazolyl, 1-Me-5-CO₂H-4-pyrazolyl, or 2-CO₂H-1-piperidyl;

R¹ is —C(=NH)NH₂ or —C(=NOH)NH₂; and

R⁴ is H, Me, Et, Pr, i-Bu, Bn, —CONH₂, —(CH₂)₂CONH₂, —(CH₂)₃CONH₂, —SO₂Me, —CH₂-cyclopropyl, or —CH₂-3-pyridyl.

In a seventh aspect, the present invention includes compounds of Formula (Id), within the scope of the sixth aspect wherein:

$L_1$ is —$CH_2$—; and
$L_2$ is a bond or —O—.

In an eighth aspect, the present invention includes compounds of Formula (Id), within the scope of the seventh aspect wherein:

A is 1,2-phenylene, 5-$CO_2$H-1,2-phenylene, 5-CONHMe-1,2-phenylene, 5-CONHEt-1,2-phenylene, 5-CONHPr-1,2-phenylene, 5-CONHBn-1,2-phenylene, 5-CONHCH$_2$CONH$_2$-1,2-phenylene, 5-CONHCH$_2$CONHMe-1,2-phenylene, 5-CONHCH$_2$CONHEt-1,2-phenylene, 5-CONH(—$CH_2$-cyclopropyl)-1,2-phenylene, 5-CONH—(—$CH_2$-cyclohexyl)-1,2-phenylene, 5-CONH—(—$CH_2$-(4-COMe-Ph))-1,2-phenylene, 5-CONH(—$CH_2$-2-oxazolyl)-1,2-phenylene, 5-CONH(—$CH_2$-1,2,4-triazolyl)-1,2-phenylene, 5-CONH(—$CH_2$-2-pyridyl)-1,2-phenylene, 5-CONH(—$CH_2$-3-pyridyl)-1,2-phenylene, 5-CONH(—$CH_2$-4-pyridyl)-1,2-phenylene, 5-CONH(—$CH_2$-2-pyrimidinyl)-1,2-phenylene, 5-CONH(—$CH_2$-3,4,5,6-tetrahydro-2-pyrimidinyl)-1,2-phenylene, 5-CONH(—$CH_2$-(5-Me-2-pyrazinyl))-1,2-phenylene, 5-CONH(—$CH_2$-2-thiazolyl)-1,2-phenylene, 5-CONH(—$CH_2$-4-thiazolyl)-1,2-phenylene, 5-CONH(—$CH_2$-5-thiazolyl)-1,2-phenylene, 5-CONH(—$CH_2$-2-imidazolyl)-1,2-phenylene, 5-CONH(—$CH_2$-4-imidazolyl)-1,2-phenylene, or 1,3-phenylene, wherein the attachment to $L_2$ is at carbon 1 of said phenylene groups;

B is 2-$CO_2$H-phenyl, 2-$CO_2$Et-phenyl, 2-CONH$_2$-phenyl, 2-CONHSO$_2$Me-phenyl, 2-SO$_2$NH$_2$-phenyl, 2-$CH_2$OH-4-OMe-phenyl, 2-$CO_2$H-3-Me-phenyl, 2-$CO_2$H-4-Me-phenyl, 2-$CO_2$H-5-Me-phenyl, 2-$CO_2$Et-4-Me-phenyl, 2-$CO_2$H-4-Cl-phenyl, 2-$CO_2$Et-4-Cl-phenyl, 2-$CO_2$H-4-OMe-phenyl, 2-$CO_2$Et-4-OMe-phenyl, 2-$CO_2$H-4-CONH$_2$-phenyl, 2-$CO_2$H-4,5-methylenedioxyphenyl, 3-$CO_2$H-6-Me-2-pyridyl, 3-$CO_2$H-5-Cl-2-pyridyl, 2-$CO_2$H-1-pyrrolidinyl, 2-$CO_2$Et-1-pyrrolidinyl, 1-Me-3-$CO_2$H-4-pyrazolyl, 1-Me-5-$CO_2$H-4-pyrazolyl, or 2-$CO_2$H-1-piperidyl;

$X^5$ is CH; and
$R^4$ is H, Me, Et, Pr, i-Bu, Bn, —CONH$_2$, —(CH$_2$)$_2$CONH$_2$, 10-(CH$_2$)$_3$CONH$_2$, —$CH_2$-cyclopropyl, or —$CH_2$-3-pyridyl.

In a ninth aspect, the present invention includes compounds of Formula (Id) or a stereoisomer or pharmaceutically acceptable salts, solvates, or prodrugs thereof, within the scope of the eighth aspect wherein:

B is 2-$CO_2$H-phenyl, 2-$CO_2$Et-phenyl, 2-$CH_2$OH-4-OMe-phenyl, 2-$CO_2$H-3-Me-phenyl, 2-$CO_2$H-4-Me-phenyl, 2-$CO_2$H-5-Me-phenyl, 2-$CO_2$H-4-Cl-phenyl, 2-$CO_2$H-4-OMe-phenyl, 2-$CO_2$H-4-CONH$_2$-phenyl, 2-$CO_2$H-3,4-methylenedioxyphenyl, 3-$CO_2$H-6-Me-2-pyridyl, 3-$CO_2$H-5-Cl-2-pyridyl, 2-$CO_2$H-1-pyrrolidinyl, 1-Me-3-$CO_2$H-4-pyrazolyl, or 1-Me-5-$CO_2$H-4-pyrazolyl.

In a tenth aspect, the present invention includes compounds of Formula (Id), within the scope of the eighth aspect wherein:

$L_1$ is —$CH_2$—;
$L_2$ is a bond;
A is 1,2-phenylene, 5-CONH(—$CH_2$-3-pyridyl)-1,2-phenylene, 5-CONH(—$CH_2$-(5-Me-2-pyrazinyl))-1,2-phenylene, or 5-CONH(—$CH_2$-2-pyrimidinyl)-1,2-phenylene;
B is 2-$CO_2$H-4-Me-phenyl, 2-$CO_2$H-4-Cl-phenyl, 2-$CO_2$H-4-OMe-phenyl, or 2-$CO_2$Et-4-OMe-phenyl;
$X^5$ is N; and
$R^4$ is Et.

In an eleventh aspect, the present invention provides a compound selected from the exemplified examples of the present invention or stereoisomers or pharmaceutically acceptable salts, solvates, or prodrugs thereof.

In another embodiment, the present invention provides a novel pharmaceutical composition, comprising: a pharmaceutically acceptable carrier and a therapeutically effective amount of a compound of the present invention or a stereoisomer or a pharmaceutically acceptable salt, solvate or prodrug form thereof.

In another embodiment, the present invention provides a pharmaceutical composition further comprising additional therapeutic agent(s) selected from potassium channel openers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, anti-obesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, or a combination thereof.

In another embodiment, the present invention provides a pharmaceutical composition further comprising additional therapeutic agent(s) selected from an anti-arrhythmic agent, an anti-hypertensive agent, an anti-coagulant agent, an anti-platelet agent, a thrombin inhibiting agent, a thrombolytic agent, a fibrinolytic agent, a calcium channel blocker, a cholesterol/lipid lowering agent, or a combination thereof.

In another embodiment, the present invention provides a pharmaceutical composition further comprising additional therapeutic agent(s) selected from warfarin, unfractionated heparin, low molecular weight heparin, synthetic pentasaccharide, hirudin, argatroban, aspirin, ibuprofen, naproxen, sulindac, indomethacin, mefenamate, dipyridamol, droxicam, diclofenac, sulfinpyrazone, piroxicam, ticlopidine, clopidogrel, tirofiban, eptifibatide, abciximab, melagatran, ximelagatran, disulfatohirudin, tissue plasminogen activator, modified tissue plasminogen activator, anistreplase, urokinase, and streptokinase, or a combination thereof.

In a preferred embodiment, the present invention provides a pharmaceutical composition wherein the additional therapeutic agent is an antihypertensive agent selected from ACE inhibitors, AT-1 receptor antagonists, ET receptor antagonists, dual ET/AII receptor antagonists, and vasopepsidase inhibitors, an antiarrythmic agent selected from IKur inhibitors, or an antithrombotic agent selected from anticoagulants selected from thrombin inhibitors, other factor XIa inhibitors, other kallikrein inhibitors, factor VIIa inhibitors and factor Xa inhibitors, and antiplatelet agents selected from GPIIb/IIIa blockers, $P2Y_1$ and $P2Y_{12}$ antagonists, thromboxane receptor antagonists, and aspirin, or a combination thereof.

In a preferred embodiment, the present invention provides pharmaceutical composition, wherein the additional therapeutic agent(s) are an anti-platelet agent or a combination thereof.

In a preferred embodiment, the present invention provides a pharmaceutical composition, wherein the additional therapeutic agent is the anti-platelet agent clopidogrel.

In another embodiment the present invention provides a method for modulation of the coagulation cascade and/or contact activation system comprising administering to a patient in need of such treatment a therapeutically effective amount of at least one of the compounds of the present invention or a pharmaceutically acceptable salt, solvate or prodrug form thereof.

In another embodiment, the present invention provides a novel method for treating thromboembolic disorders comprising: administering to a patient in need of such treatment a therapeutically effective amount of at least one of the compounds of the present invention or a pharmaceutically acceptable salt, solvate or prodrug form thereof.

In another embodiment, the present invention provides a novel method, wherein the thromboembolic disorder is selected from the group consisting of arterial cardiovascular thromboembolic disorders, venous cardiovascular thromboembolic disorders, arterial cerebrovascular thromboembolic disorders, and venous cerebrovascular thromboembolic disorders.

In another embodiment, the present invention provides a novel method, wherein the thromboembolic disorder is selected unstable angina, first myocardial infarction, recurrent myocardial infarction, ischemic sudden death, transient ischemic attack, stroke, atherosclerosis, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, and (f) other procedures in which blood is exposed to an artificial surface that promotes thrombosis.

In another embodiment, the present invention provides a method for treating inflammatory disorders comprising: administering to a patient in need of such treatment a therapeutically effective amount of at least one of the compounds of the present invention or a pharmaceutically acceptable salt or prodrug form thereof.

In another embodiment, the present invention provides a method, wherein the inflammatory disorder is selected from the group consisting of sepsis, acute respiratory dystress syndrome, and systemic inflammatory response syndrome.

In another embodiment, the present invention provides a novel method of treating a patient in need of thromboembolic disorder treatment, comprising: administering a compound of the present invention or a pharmaceutically acceptable salt, solvate, or prodrug form thereof in an amount effective to treat a thromboembolic disorder.

In another embodiment, the present invention provides a method of treating a patient in need of inflammatory disorder treatment, comprising: administering a compound of the present invention or a pharmaceutically acceptable salt form thereof in an amount effective to treat an inflammatory disorder.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt, solvate, or prodrug form thereof; and
(c) a package insert stating that the pharmaceutical composition can be used for the treatment of a thromboembolic and/or inflammatory disorder.

In another preferred embodiment, the present invention provides a novel article of manufacture, further comprising:
(d) a second container; wherein components (a) and (b) are located within the second container and component (c) is located within or outside of the second container.

In another embodiment, the present invention provides a novel article of manufacture, comprising:
(a) a first container;
(b) a pharmaceutical composition located within the first container, wherein the composition, comprises: a first therapeutic agent, comprising: a compound of the present invention or a pharmaceutically acceptable salt, solvate, or prodrug form thereof; and
(c) a package insert stating that the pharmaceutical composition can be used in combination with a second therapeutic agent to treat a thromboembolic and/or inflammatory disorder.

In another preferred embodiment, the present invention provides a novel article of manufacture, further comprising:
(d) a second container; wherein components (a) and (b) are located within the second container and component (c) is located within or outside of the second container.

In another embodiment, the present invention provides a novel method, comprising: administering a compound of the present invention or a pharmaceutically acceptable salt, solvate, or prodrug form thereof in an amount effective to treat a thromboembolic and/or inflammatory disorder.

In another embodiment, the present invention provides a compound of the present invention or a pharmaceutically acceptable salt, solvate, or prodrug form thereof, for use in therapy.

In another embodiment, the present invention also provides the use of a compound of the present invention or a pharmaceutically acceptable salt, solvate, or prodrug form thereof, for the manufacture of a medicament for the treatment of a thromboembolic and/or inflammatory disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is its own independent preferred embodiment. Furthermore, any element of an embodiment is meant to be combined with any and all other elements from any embodiment to describe an additional embodiment.

Definitions

Compounds of this invention may have one or more asymmetric centers. Unless otherwise indicated, all chiral (enantiomeric and diastereomeric) and racemic forms of compounds of the present invention are included in the present invention. Many geometric isomers of olefins, C=N double bonds, and the like can also be present in the compounds, and all such stable isomers are contemplated in the present invention. Accordingly, the present compounds can be isolated in optically active or racemic forms. It is well known in the art how to prepare optically active forms, such as by resolution of racemic forms or by synthesis from optically active starting materials. All chiral, (enantiomeric and diastereomeric) and racemic forms and all geometric isomeric forms of a structure are intended, unless the specific stereochemistry or isomer form is specifically indicated. All tautomers of shown or described compounds are also considered to be part of the present invention.

Preferably, the molecular weight of compounds of the present invention is less than about 500, 550, 600, 650, 700, 750, or 800 grams per mole. Preferably, the molecular weight is less than about 800 grams per mole. More preferably, the molecular weight is less than about 750 grams per mole. Even more preferably, the molecular weight is less than about 700 grams per mole.

As used herein, the term "alkyl" or "alkylene" is intended to include both branched and straight-chain saturated aliphatic hydrocarbon groups having the specified number of carbon atoms. For example, "$C_1$-$C_{10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$-$C_6$ alkyl" denotes alkyl having 1 to 6 carbon atoms. Alkyl groups can be unsubstituted or substituted so that one or more of its hydrogens are replaced by another chemical group. Example alkyl groups include, but are not limited to, methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like.

"Alkenyl" or "alkenylene" is intended to include hydrocarbon chains of either straight or branched configuration and having one or more double carbon-carbon bonds that may occur in any stable point along the chain. For example, "$C_2$-$C_6$ alkenyl" (or alkenylene), is intended to include $C_2$, $C_3$, $C_4$, $C_5$, and $C_6$ alkenyl groups. Examples of alkenyl include, but are not limited to, ethenyl, 1-propenyl, 2-propenyl, 2-butenyl, 3-butenyl, 2-pentenyl, 3, pentenyl, 4-pentenyl, 2-hexenyl, 3-hexenyl, 4-hexenyl, 5-hexenyl, 2-methyl-2-propenyl, 4-methyl-3-pentenyl, and the like.

"Alkynyl" or "alkynylene" is intended to include hydrocarbon chains of either straight or branched configuration and having one or more triple carbon-carbon bonds that may occur in any stable point along the chain. For example, "$C_2$-$C_6$ alkynyl" (or alkynylene), is intended to include $C_2$, $C_3$, $C_4$, $C_5$, and $C_6$ alkynyl groups; such as ethynyl, propynyl, butynyl, pentynyl, hexynyl and the like.

"Halo" or "halogen" includes fluoro, chloro, bromo, and iodo. "Haloalkyl" refers to branched and straight-chained, having one or more halogen substituents. Example haloalkyl groups include, but are not limited to, $CF_3$, $C_2F_5$, $CHF_2$, $CCl_3$, $CHCl_2$, $C_2Cl_5$, and the like.

The term "alkoxy" or "alkyloxy" refers to an 40-alkyl group. "$C_1$-$C_6$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy, and the like. Similarly, "alkylthio" or "thioalkoxy" represents an alkyl group as defined above with the indicated number of carbon atoms attached through a sulphur bridge; for example methyl-S—, ethyl-S—, and the like.

"Haloalkoxy" or "haloalkyloxy" represents a haloalkyl group as defined above with the indicated number of carbon atoms attached through an oxygen bridge. For example, "$C_1$-$C_6$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, pentafluorothoxy, and the like. Similarly, "haloalkylthio" or "thiohaloalkoxy" represents a haloalkyl group as defined above with the indicated number of carbon atoms attached through a sulphur bridge; for example trifluoromethyl-S—, pentafluoroethyl-S—, and the like.

The term "cycloalkyl" refers to cyclized alkyl groups, including mono-, bi- or poly-cyclic ring systems. $C_{3-7}$ cycloalkyl is intended to include $C_3$, $C_4$, $C_5$, $C_6$, and $C_7$ cycloalkyl groups. Example cycloalkyl groups include, but are not limited to, cyclopropyl, cyclobutyl, cyclopentyl, cyclohexyl, norbornyl, and the like.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic ring, any of which may be saturated, partially unsaturated, unsaturated or aromatic. Examples of such carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocycle (e.g., [2.2.2]bicyclooctane). Preferred carbocycles, unless otherwise specified, are cyclopropyl, cyclobutyl, cyclopentyl, cyclohexyl, phenyl, and indanyl. When the term "carbocycle" is used, it is intended to include "aryl".

A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge.

"Aryl" groups refer to monocyclic or polycyclic aromatic hydrocarbons, including, for example, phenyl, naphthyl, phenanthranyl, and the like. Aryl moieties are well known and described, for example, in *Hawley's Condensed Chemical Dictionary* (13 ed.), R. J. Lewis, ed., J. Wiley & Sons, Inc., New York (1997). Aryl groups can be substituted or unsubstituted.

As used herein, the term "heterocycle" or "heterocyclic group" is intended to mean a stable 5, 6, or 7-membered monocyclic or bicyclic or 7, 8, 9, 10, 11, 12, 13, or 14-membered bicyclic heterocyclic ring which is saturated, partially unsaturated or fully unsaturated, and which consists of carbon atoms and 1, 2, 3 or 4 heteroatoms independently selected from N, O and S; and including any bicyclic group in which any of the above-defined heterocyclic rings is fused to a benzene ring. The nitrogen and sulfur heteroatoms may optionally be oxidized (i.e., N→O and $S(O)_p$). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. When the term "heterocycle" is used, it is intended to include heteroaryl.

Examples of heterocycles include, but are not limited to, acridinyl, azocinyl, benzimidazolyl, benzofuranyl, benzothiofuranyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

Preferred 5 to 10 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, triazolyl, benzimidazolyl, 1H-indazolyl, benzofuranyl, benzothiofuranyl, benztetrazolyl, benzotriazolyl, benzisoxazolyl, benzoxazolyl, oxindolyl, benzoxazolinyl, benzthiazolyl, benzisothiazolyl, isatinoyl, isoquinolinyl, octahydroisoquinolinyl, tetrahydroisoquinolinyl, tetrahydroquinolinyl, isoxazolopyridinyl, quinazolinyl, quinolinyl, isothiazolopyridinyl, thiazolopyridinyl, oxazolopyridinyl, imidazolopyridinyl, and pyrazolopyridinyl.

Preferred 5 to 6 membered heterocycles include, but are not limited to, pyridinyl, furanyl, thienyl, pyrrolyl, pyrazolyl, pyrazinyl, piperazinyl, piperidinyl, imidazolyl, imidazolidinyl, indolyl, tetrazolyl, isoxazolyl, morpholinyl, oxazolyl, oxazolidinyl, tetrahydrofuranyl, thiadiazinyl, thiadiazolyl, thiazolyl, triazinyl, and triazolyl. Also included are fused ring and spiro compounds containing, for example, the above heterocycles.

As used herein, the term "aromatic heterocyclic group" or "heteroaryl" is intended to mean a stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, benzodioxane, and the like. Heteroaryl groups can be substituted or unsubstituted. The nitrogen atom may be substituted or unsubstituted (i.e., N or NR wherein R is H or another substituent, if defined). The nitrogen and sulfur heteroatoms may optionally be oxidized (i.e., $N \rightarrow O$ and $S(O)_p$). It is to be noted that total number of S and O atoms in the aromatic heterocycle is not more than 1. Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a tricyclic ring. When a ring is bridged, the substituents recited for the ring may also be present on the bridge.

The term "counterion" is used to represent a small, negatively charged species such as chloride, bromide, hydroxide, acetate, and sulfate.

As referred to herein, the term "substituted" means that one or more hydrogen atoms is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring.

When any variable (e.g., $R^{2a}$, $R^{2b}$, etc.) occurs more than one time in any constituent or formula for a compound, its definition at each occurrence is independent of its definition at every other occurrence. Thus, for example, if a group is shown to be substituted with 0-3 $R^{2b}$, then said group may optionally be substituted with up to three $R^{2b}$ groups and $R^{2b}$ at each occurrence is selected independently from the definition of $R^{2b}$. Also, combinations of substituents and/or variables are permissible only if such combinations, result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable salt" refers to acid or base salts of the compounds described herein. Examples of pharmaceutically acceptable salts include, but are not limited to, mineral or organic acid salts of basic residues such as amines; alkali or organic salts of acidic residues such as carboxylic acids; and the like. Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference in its entirety. Examples of pharmaceutically acceptable salts include, but are not limited to, mineral or organic acid salts of basic residues such as amines; alkali or organic salts of acidic residues such as carboxylic acids; and the like. Pharmaceutically acceptable salts include the conventional non-toxic salts or the quaternary ammonium salts of the parent compound formed, for example, from non-toxic inorganic or organic acids. Such conventional non-toxic salts include those derived from inorganic acids such as hydrochloric, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

"Prodrugs" refer to inactive compounds that can be converted upon absorption by a mammalian subject to an active compound of the present invention. Prodrugs of the compounds of the present invention can be prepared by modifying functional groups present in the compounds of the present invention in such a way that the modifications are cleaved in vivo to produce the parent compounds. Examples of prodrugs include, but are not limited to, acetate, formate and benzoate derivatives of alcohol and amine functional groups in the compounds of the present invention. Preparation of prodrugs is well known in the art and described in, for example, *Medicinal Chemistry: Principles and Practice*, ed. F. D. King, The Royal Society of Chemistry, Cambridge, UK, 1994, which is incorporated herein by reference in its entirety.

Radiolabelled compounds of the present invention, i.e., wherein one or more of the atoms described are replaced by a radioactive isotope of that atom (e.g., C replaced by $^{13}$C or by $^{14}$C; and isotopes of hydrogen include tritium and deuterium), are also provided herein. Such compounds have a variety of potential uses, e.g., as standards and reagents in determining the ability of a potential pharmaceutical to bind to target proteins or receptors, or for imaging compounds of this invention bound to biological receptors in vivo or in vitro.

Compounds of the present invention are, subsequent to their preparation, preferably isolated and purified to obtain a composition containing an amount by weight equal to or greater than 99% compound of the present invention ("substantially pure"), which is then used or formulated as described herein. Such "substantially pure" compounds are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. It is preferred that compounds of the present invention do not contain a N-halo, $S(O)_2H$, or $S(O)H$ group.

It should further be understood that solvates (e.g., hydrates) of the compounds of the present invention are also with the scope of the present invention. Methods of solvation are generally known in the art.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor XIa and/or plasma kallikrein. "Therapeutically effective amount" is also intended to include an amount of the combination of compounds claimed that is effective to inhibit factor XIa and/or plasma kallikrein. The combination of compounds is preferably a synergistic combination. Synergy, as described, for example, by Chou and Talalay, *Adv. Enzyme Regul.* 1984, 22:27-55, occurs when the effect (in this case, inhibition of factor XIa and/or plasma kallikrein) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic and/or anti-inflammatory effect, or some other beneficial effect of the combination compared with the individual components.

The present invention further includes compositions comprising one or more compounds of the present invention and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and nonaqueous liquid media, as well as a variety of solid and semisolid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences*, 17th ed., Mack Publishing Company, Easton, Pa., 1985, which is incorporated herein by reference in its entirety.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below. The reactions are performed in a solvent appropriate to the reagents and materials employed and suitable for the transformations being effected. It will be understood by those skilled in the art of organic synthesis that the functionality present on the molecule should be consistent with the transformations proposed. This will sometimes require a judgment to modify the order of the synthetic steps or to select one particular process scheme over another in order to obtain a desired compound of the invention. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Wiley-Interscience, 3$^{rd}$ Edition, 1999).

All references cited herein are hereby incorporated in their entirety herein by reference.

Representative indole compounds of this invention can be prepared as shown in Scheme 1. An appropriately functionalized indole, such as 6-cyanoindole 1a, is condensed with a suitably substituted benzaldehyde 1b in the presence of a base such as sodium hydroxide in a solvent such as methanol. Subsequent reduction with triethylsilane in a mixture of methylene chloride and trifluoroacetic acid provides the benzylindole intermediate 1c. An Suzuki coupling between 1c and an appropriately substituted phenylboronic acid or ester in the presence of a base such as aq. sodium carbonate or anhydrous potassium phosphate in a solvent such as toluene, dioxane or a mixture of toluene and ethanol using a catalyst such as tetrakis(triphenylphosphine)-palladium provides the biaryl compound 1d. Treatment of 1d with a base such as sodium hydride or potassium t-butoxide in DMF followed by addition of a suitable bromide or chloride, such as for example benzyl or ethyl bromide provides the corresponding N-alkylated compound. Further manipulation of the functional groups on both the indole ring and the pendant groups and deprotection as necessary, using methods known to one skilled in the art of organic synthesis, will give compounds of the invention. For compounds of the invention wherein $R^1$ is an amidino group, conversion of the nitrile to the corresponding amidine can be carried out by a number of methods known in the literature, for example by Pinner reaction followed by ammonolysis or alternately by conversion to an intermediate amidoxime, which after treatment with acetic anhydride, is reduced, either by catalyic hydrogenation in the presence of a suitable catalyst, such as 5% palladium on carbon or Raney nickel, or with zinc dust, to give the amidine 1e. Compounds where $R^1$ is carbamoyl or aminomethyl can similarly be prepared from the nitrile intermediate by treatment with basic hydrogen peroxide in the case of the amide or by catalytic hydrogenation of the nitrile to the corresponding amine.

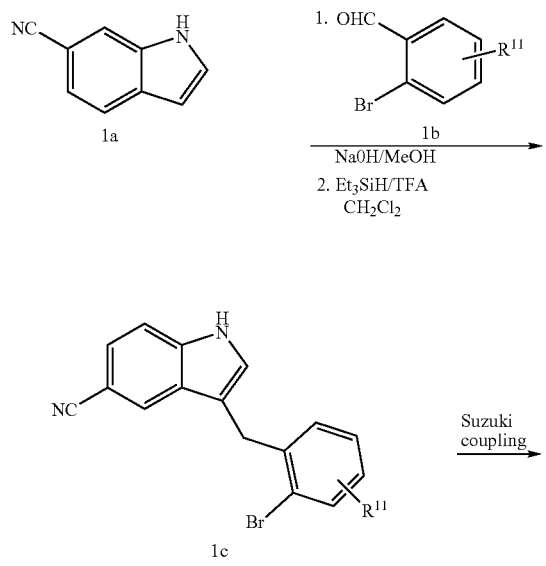

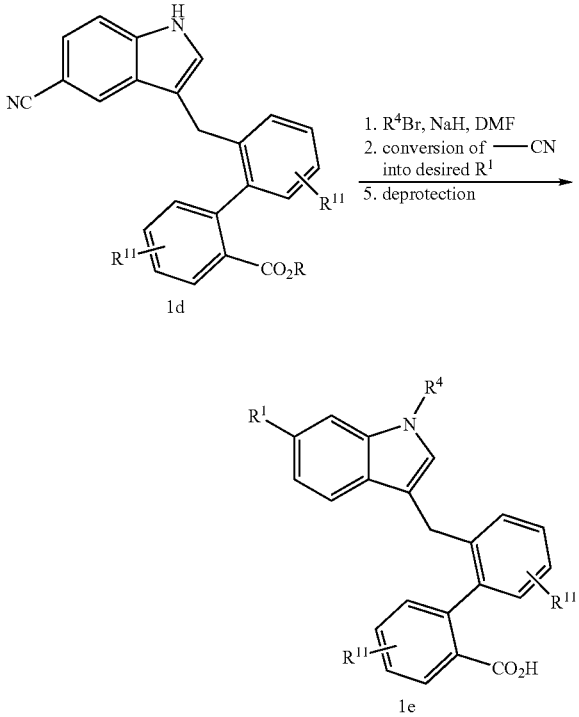

Alternately, the N-substituted indoles 1e shown in Scheme 1 can be prepared by alkylation of intermediate 1c prior to introduction of the second aromatic ring.

Compounds of the invention wherein $L_1$ is a two atom linker, i.e., —CH$_2$NH—, —CH$_2$O—, or —CONH—, can be prepared from a common intermediate such as aldehyde 2b as outlined in Scheme 2. Starting aldehydes 2b are readily available via a Vilsmeier reaction to introduce a formyl group onto an appropriately substituted indole compound 2a, followed by alkylation of the indole nitrogen as described above. Reduction amination of 2b with an suitably functionalized aniline in the presence of a reducing agent such as sodium triacetoxyborohydride or sodium cyanoborohydride provides compounds of formula 2h. Alternately, aldehydes 2b can be reduced to the corresponding alcohols 2c which can then be reacted with suitably functionalized phenols under Mitsunobu conditions to provide compounds of formula 2f. As an alternative to the Mitsunobu reaction, compounds 2f can be prepared by alkylation of a suitably functionalized phenol in using bromides derived from alcohols 2c in the presence of a base such as potassium carbonate or cesium carbonate. The conversion of alcohols 2c into the corresponding bromides can be readily achieved using any of a number of methods known in the art, for example, by treatment of the alcohol with either phosphorous tribromide or a mixture of carbon tetrabromide and triphenylphosphine. Compounds where L1 is an amide linkage can also be prepared from common intermediate 2b by oxidation of the aldehyde to the corresponding acid. This oxidation can be conveniently achieved using sodium chlorite or by a number of other methods known in the art. Coupling of the resulting acid 2d with suitably substituted anilines provides amides 2 g.

Scheme 2

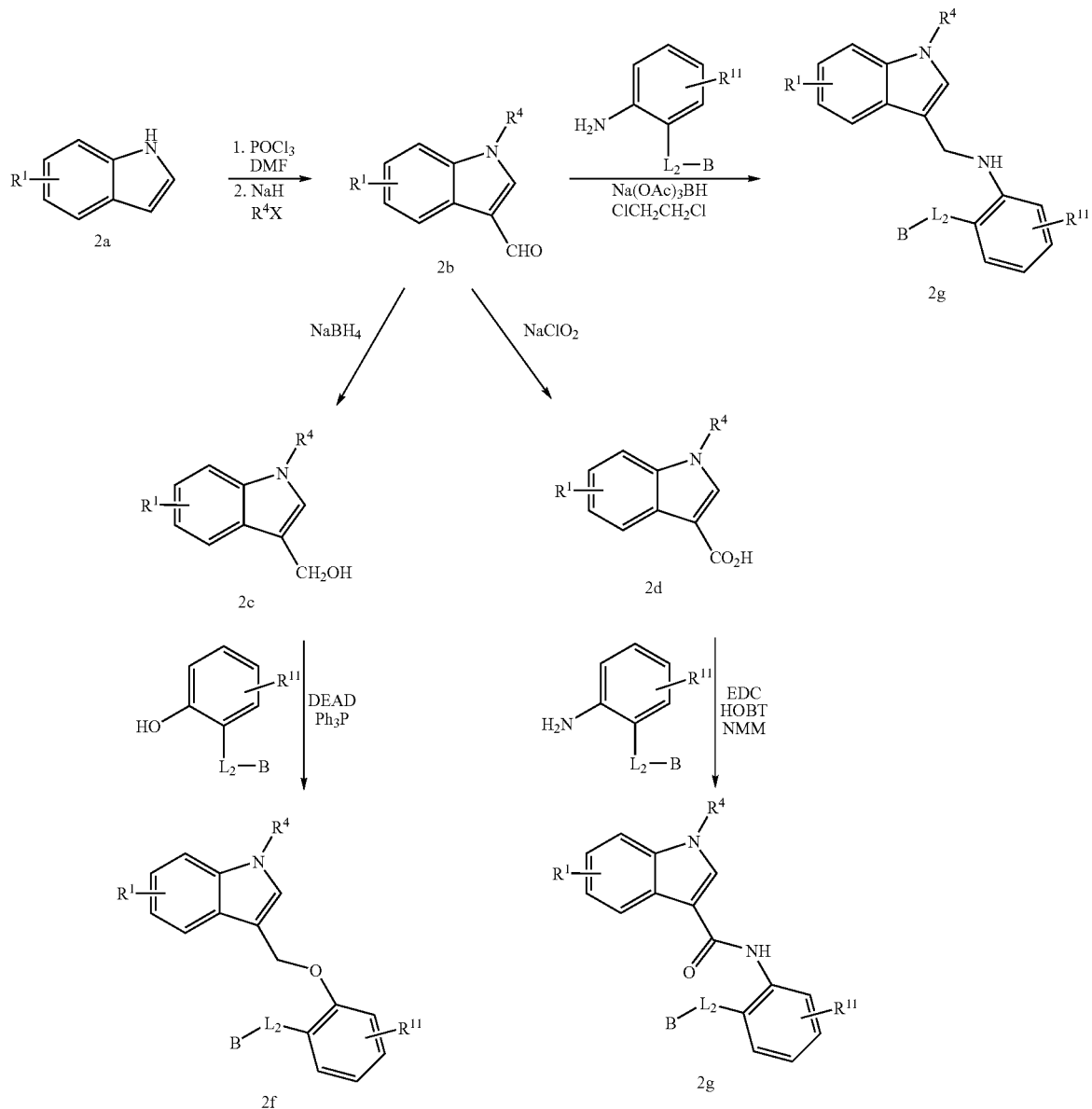

Methods for synthesis of a large variety of substituted indoles useful as starting materials for the preparation of indole compounds of the present invention are well known in the art and have been extensively reviewed. (For examples of methods useful for the preparation of indole starting materials see: Hegedus, L. S., *Angew. Chem.* 1988, 100, 1147; Pindur, U. & Reinhard, A., *J. Heterocyclic Chem.* 1988, 25, 1; Clard, R. D. & Repke, D. B., *Heterocycles,* 1984, 22, 195; Ambekar, S. Y. *Curr. Sci.* 1983, 52, 578 and Zhu, X. & Ganesan, A. *J. Org. Chem.,* 2002, 67, 2705). Methods for the synthesis of various substituted azaindoles which can be substituted for indoles 1a and 2a in Schemes 1 & 2 above to allow preparation of additional compounds of the present invention, wherein one or more of $X^1$, $X^2$, $X^3$, or $X^4$ are N, are also known in the art and include but are not limited to the following: Rodriquez, A. L. et al. *Angew. Chemie Intl. Ed.* 2000, 39, 2488; Siu, J. et al. *Organic & Biomolecular Chem.* 2004. 2. 160; L'Heureux, A. et al. *Tet. Lett.* 2004. 45. 2317.

Methods applicable to the synthesis of indazole intermediates which can be substituted for indoles 1a and 2a in Schemes 1 & 2 above to allow preparation of additional compounds of the present invention, wherein $X^5$ is N, are described by Stadlbauer (*Science of Synthesis,* 2002, 12, 227), Paterson et al. (*Tet. Lett.* 1977, 45, 3973), Dennler & Frasca (*Tetrahedron* 1966, 22, 3131, and Rodgers et al. (*Bioorg. Med. Chem. Lett.* 1998, 8, 715). Specific indazole intermediates useful for the synthesis of compounds of the present invention can also be prepared as shown in Scheme 2a below wherein an appropriately substituted benzylbromide is reacted with zinc dust followed by Pd-catalyzed coupling of the resulting benzylzinc bromide species with a suitably substituted benzoyl chloride. Treatment of the resulting ketone with an alkyl hydrazine under microwave heating provides the indazole. Deprotection of the t-butyl ester and amide formation leads to an intermediate which, after further elaboration as described in Scheme 1 and further illustrated in the examples given below, will lead to indazole compounds of this invention.

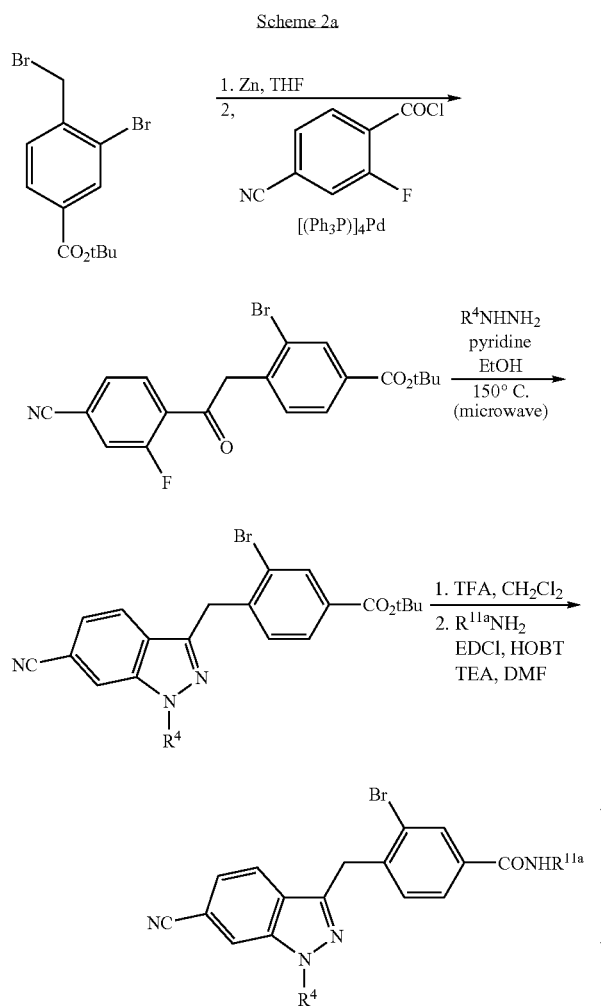

Scheme 2a

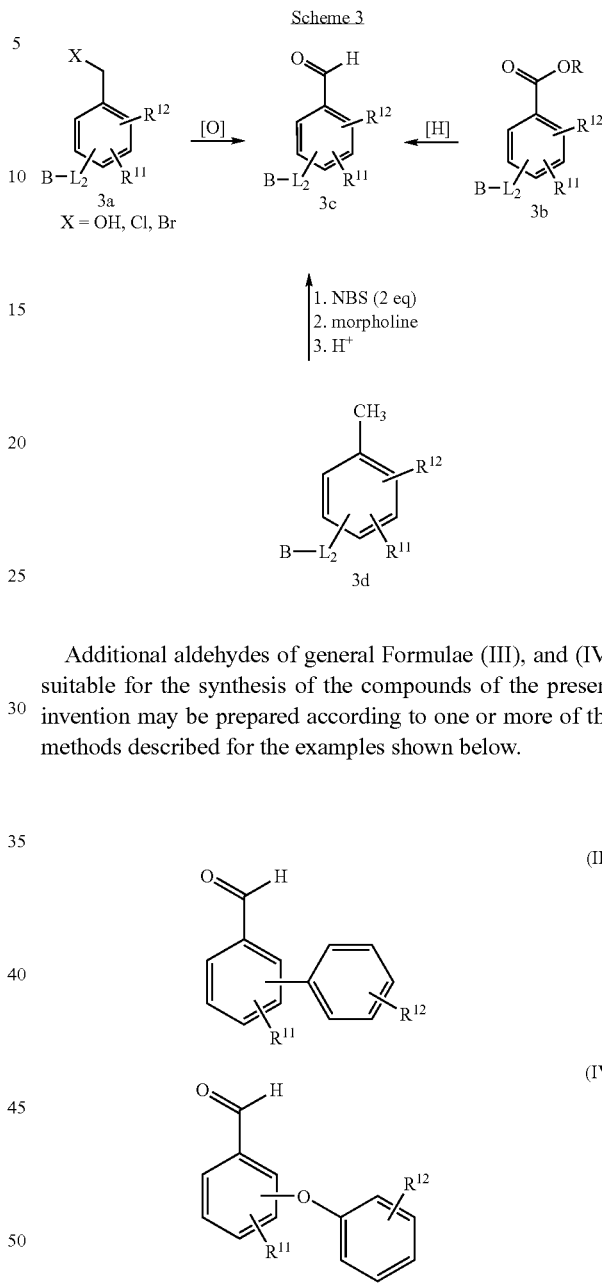

Scheme 3

Suitable aldehydes useful for the synthesis of compounds in Scheme 1 are accessible from a variety of straightforward chemical transformations known to one skilled in the art. As outlined in Scheme 3, aldehydes 3c suitable for use in preparing compounds of this invention may be obtained through oxidation of the corresponding alcohols or halides 3a as taught in "*Advanced Organic Chemistry*" (Jerry March, Wiley Interscience pg 1057-60 and pg 1081 and references therein). Alternatively suitable aldehydes may be prepared by hydrogenation of the corresponding carboxylic acids 3b (Scheme 5, R=H) in the presence of palladium complexes and pivalic anhydride (Nagayama et al. *Chemistry Letters* 1998, 27, 1143-1144) or by reduction of an ester (R=alkyl) with DIBAL-H (Chandrasekhar et al. *Tetrahedron Letters* 1998, 39, 909-910). Additional aryl aldehydes may be obtained directly from the corresponding toluene derivatives 3d via oxidation or bromination of the methyl group.

Additional aldehydes of general Formulae (III), and (IV) suitable for the synthesis of the compounds of the present invention may be prepared according to one or more of the methods described for the examples shown below.

Substituted biaryl aldehyde intermediates of general Formula (III) may be prepared as outlined in Scheme 4. It is appreciated that one skilled in the art could readily apply the methods described below to make additional substituted biphenyl aldehydes of Formula (III). In this approach, a suitably substituted aryl iodide, bromide or triflate can serve as a common intermediate for the preparation of biaryl aldehydes through metal-mediated cross coupling reactions of the type described by Fu et al. (*J. Amer. Chem. Soc.* 2000, 122, 4020-4028). For example, 2-formylphenylboronic acid can be coupled with methyl 2-iodobenzoate in the presence of a palladium catalyst, such as tetrakis(triphenylphosphine)palladium, a suitable base, such as aqueous sodium carbonate or anhydrous potassium phosphate, in a suitable solvent such as toluene, toluene/EtOH mixtures, dioxane or DMF, at a reaction temperature between 85-110° C. and a reaction time of between 2-24 h.

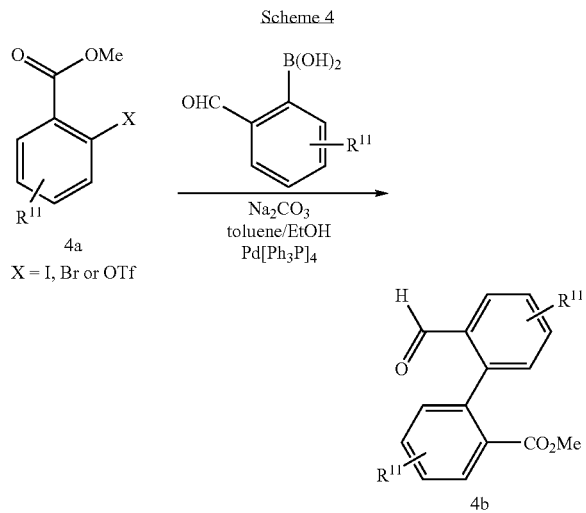

In cases where suitably substituted boronic acids are not commercially available, a modification to this approach may be adopted wherein an aryl bromide intermediate, for example, t-butyl 3-bromo-4-methylbenzoate, is subjected to a palladium mediated coupling with a diboron species such as bis(pinacolato) diboron to provide the corresponding 4,4,5,5-tetramethyl-[1,3,2]dioxaborolane intermediate using the method of Ishiyama et al. (J. Org. Chem. 1995, 60, 7508). Alternately, this same intermediate can be prepared by reaction of the intermediate bromide with the corresponding dialkoxyhydroborane as described by Murata et al. (J. Org. Chem. 1997, 62, 6458). The boron pinacolate intermediates can be used in place of boronic acids for coupling to the aryl halides or triflates in Scheme 4.

Intermediate aldehydes of the general Formula (IV) may be synthesized via an Ullmann-type copper-mediated displacement of an aryl bromide with a suitably substituted phenol (for a review see S. V. Ley & A. W. Thomas Angew. Chemie Int. Ed. 2003, 42, 5400) or a copper mediated cross-coupling reaction of a phenol with aryl boronic acids using the methodology developed by Chan and co-workers (see Tetrahedron Lett. 1998 39, 2933).

The approaches described herein when applied to the synthesis of biaryl aldehyde intermediates can therefore facilitate the synthesis of a wide range of intermediates derived from either aryl halides or phenols, the precursors to aryl triflates.

It is also realized that the scope of intermediate synthesis can be further extended outside the use of Suzuki methodology since the precursor aryl halides or triflates described above are also precursors for Stille-type cross coupling methodologies. Suitable methodology for the synthesis of substituted aldehydes of Formula III using Stille coupling has been reported by Kohrt et al. (Tetrahedron Lett. 2000, 41, 6041-44).

The various coupling methods described above for the preparation of biarylaldehydes can similarly be used for the preparation of biarylamine and phenol intermediates useful in the synthesis of compounds of this invention described in Scheme 2 above.

Other features of the invention will become apparent in the course of the following descriptions of exemplary embodiments that are given for illustration of the invention and are not intended to be limiting thereof.

EXAMPLES

Solution ratio expresses a volume relationship, unless stated otherwise. NMR chemical shifts (δ) are reported in parts per million. Flash chromatography was carried out on silica gel according to Still's method (Still, W. C. et al. J. Org. Chem. 1978, 43, 2923).

As used throughout the specification, the following abbreviations for chemical reagents apply:
HOAc or AcOH=acetic acid
Bn=benzyl
BOP=benzotriazol-1-yloxy-tris(dimethylamino)-phosphonium hexafluorophosphate
Bu=butyl
t-Bu=tertiary butyl
Boc tert-butyl oxycarbonyl
$CH_2Cl_2$=dichloromethane
DCE=1,2-dichloroethane
DMF=dimethylformamide
DMSO=dimethyl sulfoxide
Et=ethyl
$Et_2O$=diethyl ether
EtOH=ethanol
EtOAc=ethyl acetate
HCl=hydrochloric acid
Me=methyl
MeOH=methanol
NaOAc=sodium actetate
$Na_2SO_4$=sodium sulfate
NMM=N-methyl morpholine
OAc=acetate
Ph=phenyl
Pr=propyl
i-Pr=isopropyl
i-PrOH=isopropanol
TFA=trifluoroacetic acid
THF=tetrahydrofuran
° C.=degrees Celsius
anh.=anhydrous
atm=atmosphere
conc.=concentrated
eq=equivalent(s)
h or hr=hour(s)
g=gram(s)
mg=milligram(s)
L=liter(s)
mL=milliliter(s)
μL=microliter(s)
mmol=millimolar
M=molar
meq=milliequivalent(s)
Min=minute(s)
MW=molecular weight
mp=melting point
rt or RT=room temperature
sat or sat'd=saturated
ESI=electrospray ionization mass spectroscopy
HPLC=high performance liquid chromatography
MS=mass spectrometry
LC/MS=liquid chromatography mass spectrometry
NMR=nuclear magnetic resonance spectroscopy
TLC=thin layer chromatography "α", "β", "R", "S", "E", and "Z" are stereochemical designations familiar to one skilled in the art. One stereoisomer of a compound of Formula I may display superior activity compared with the others. Thus, each stereoisomer of a compound of Formula I is considered to be a part of the present invention. When required, separation of the racemic material can be achieved by HPLC using a chiral column or by a resolution using a resolving agent such as described in Wilen, S. H. *Tables of Resolving Agents and Optical Resolutions* 1972, 308 or using enantiomerically pure acids and bases. A chiral compound of Formula I may also be directly synthesized using a chiral catalyst or a chiral ligand, e.g., Jacobsen, E. *Acc. Chem. Res.* 2000, 33, 421-431 or using other enantio- and diastereo-selective reactions and reagents known to one skilled in the art of asymmetric synthesis.

The following Examples have been prepared, isolated and characterized using the methods disclosed herein. The following Examples demonstrate a partial scope of the invention and are not meant to be limiting of the scope of the invention.

Example 1

2'-(6-Carbamimidoyl-1H-indol-3-ylmethyl)-4-methoxy-biphenyl-2-carboxylic acid

Part A. 3-(2-bromobenzyl)-1H-indole-6-carbonitrile: A mixture of 6-cyanoindole (0.5 g, 3.52 mmol), 2-bromobenzaldehyde (0.97 g, 5.28 mmol) and sodium hydroxide (0.15 g, 3.87 mmol) in 20 mL MeOH was stirred at rt overnight. Solvent was removed by evaporation, and residue was partitioned between EtOAc and water. Phases were separated, and organic phase was washed with brine and dried over anh. $Na_2SO_4$, filtered and evaporated to provide 1.5 g crystalline product which was dissolved in 15 mL $CH_2Cl_2$ and treated with triethylsilane (0.82 g, 0.73 mmol). The resulting mixture was cooled to 0° C. in an ice bath and then TFA (0.4 ml, 5.3 mmol) was added dropwise. The mixture was stirred for 2 h allowing a gradual warm-up to rt. Reaction was stripped to dryness and residue was chromatographed on silica get eluted with a gradient from 0-80% EtOAc in hexane to provide the 3-benzylindole analog (0.64 g, 58%). $^1$HNMR (500 MHz, $CDCl_3$) δ 4.21 (s, 2H); 7.09 (m, 1H); 7.15 (m, 2H); 7.20 (m, 1H); 7.34 (m, 1H); 7.61 (m, 2H); 7.71 (sm 2H); 8.28 (bs, 1H). LC/MS m/z 309.1/311.2 $(M+H)^+$.

Part B. 3-(2'-formyl-4'-methoxy-biphenyl-2-ylmethyl)-1H-indole-6-carbonitrile: A mixture of the compound of Part A (0.24 g, 0.77 mmol) and 2-formyl-4-methoxyphenylboronic acid (0.17 g, 0.93 mmol) in 10 mL dioxane was treated with $K_3PO_4$ (0.41 g, 1.9 mmol). The resulting mixture was degassed followed by addition of tetrakis(triphenylphosphine)palladium (36 mg, 0.03 mmol). The reaction was then heated in 100° C. oil bath overnight. Work-up and flash chromatography provided the desired product (0.2 g, 71%). $^1$HNMR (500 MHz, $CDCl_3$) δ 3.87 (s, 3H); 3.86-3.91 (m, 2H); 6.75 (s, 1H); 7.10 (m, 1H); 7.20 (m, 4H); 7.31 (m, 2H); 7.39 (m, 2H); 7.63, (s, 1H); 8.14 (bs, 1H); 9.44 (s, 1H). LC/MS m/z 365.3/367.2 $(M+H)^+$.

Part C. 2'-(6-cyano-1H-indol-3-ylmethyl)-4-methoxy-biphenyl-2-carboxylic acid: The compound of Part B (0.1 g, 0.27 mmol) was dissolved in a mixture of 6 mL tBuOH, 1 mL $CH_3CN$ and 2 mL $H_2O$. To this solution was added 2-methyl-2-butene (0.17 ml, 1.64 mmol), followed by sodium dihydrogen phosphate (49 mg, 0.41 mmol) and sodium chlorite (0.11 g, 1.2 mmol). The reaction was stirred at rt for 1 h, then diluted with water and extracted with EtOAc (3×). The combined extracts were washed with brine, dried and evaporated. Flash chromatography provided the acid (72 mg, 72%). LC/MS m/z 381.2/383.1 $(M+H)^+$.

Part D. Example 1: A mixture of the compound of Part C (72 mg, 0.19 mmol), hydroxylamine hydrochloride (79 mg, 1.13 mmol) and triethylamine (0.16 ml, 1.13 mmol) in 5 mL EtOH was heated in a 95° C. oil bath at reflux for 6 h. Reaction was then cooled to rt and evaporated to dryness. Residue was purified by reverse phase HPLC to provide the amidoxime in 74% yield. (LC/MS m/z 414.2/416.1 $(M+H)^+$.) The product (0.14 mmol) was redissolved in 5 mL EtOH and treated with HOAc (0.016 ml, 0.28 mmol) followed by addition of 0.11 mL cyclohexene and 20 mg palladium hydroxide. The reaction mixture was heated to reflux in 95° C. oil bath for 5 h, cooled to rt and catalyst removed by filtration. Reverse phase HPLC using a C18 column and a $H_2O/CH_3CN/TFA$ mobile phase followed by lyophilization provided Example 1 as its TFA salt (45.6 mg, 64%). $^1$HNMR (500 MHz, DMSO-$d_6$) δ 3.82 (s, 3H); 3.83 (m, 2H); 7.03 (m, 2H); 7.12 (m, 4H); 7.30 (m, 2H); 7.39 (m, 2H); 7.82 (m, 1H) 8.68 (s, 2H); 9.10 (s, 2H). HRMS calcd. for $C_{21}H_{22}N_3O_3$: 400.1661. Found: 400.1646.

Example 2

2'-(1-Benzyl-6-carbamimidoyl-1H-indol-3-ylmethyl)-4-methoxy-biphenyl-2-carboxylic acid Part A. 1-benzyl-3-(2'-formyl-4'-methoxy-biphenyl-2-ylmethyl)-1H-indole-6-carbonitrile: The compound of Example 1, Part B (0.1 g, 0.27 mmol) was dissolved in 2 mL DMF and cooled to 0° C. in an ice bath. To the cold solution was added sodium hydride (60% in oil, 12 mg, 0.30 mmol), and the mixture was stirred for 10-15 min followed by addition of benzyl bromide (0.036 ml, 0.30 mmol). The reactoin was then stirred overnight at rt. Work-up and chromatography provided the N-benzylindole (0.1 g, 83%) as a white solid. LRMS m/z 457.1 $(M+H)^+$.

Part B. 2'-(1-benzyl-6-cyano-1H-indol-3-ylmethyl)-4-methoxy-biphenyl-2-carboxylic acid: The compound of Part A was oxidized with sodium chlorite using the procedure of Example 1, Part C to provide the corresponding acid as a crystalline solid. LRMS m/z 473.0 $(M+H)^+$.

Part C. Example 2: The compound of Part B was converted to the corresponding amidoxime using the procedure described in Example 1, Part D. The crude amidoxime was dissolved in 2 mL glacial acetic acid and treated with acetic anhydride (0.066 ml, 3 eq). The solution was stirred for 10 min followed by addition of zinc dust (0.15 g, 10 eq). Stirring was continued at rt for 2 h. Reaction mixture was filtered and filtrate concentrated. Reverse phase HPLC of the residue as described above and lyophilization provided Example 2 as its TFA salt in 51% yield. $^1$HNMR (500 MHz, DMSO-$d_6$) δ 3.80 (s, 3H); 3.82 (m, 2H); 5.39 (m, 2H); 7.06 (m, 4H); 7.17 (m, 4H); 7.26 (m, 2H); 7.32 (m, 4H); 7.42 (m, 1H); 8.04 (s, 1H); 8.71 (s, 2H); 9.09 (s, 2H). HRMS calcd for $C_{31}H_{28}N_3O_3$: 490.2131. Found: 490.2110.

Example 3

2'-(6-Carbamimidoyl-1-ethyl-1H-indol-3-ylmethyl)-4-methoxy-biphenyl-2-carboxylic acid Example 3 was prepared as its TFA salt from the compound of Example 1, Part B as described for Example 2 using ethyl bromide in place of benzyl bromide. $^1$H NMR (500 MHz, DMSO-$d_6$) δ ppm 1.29 (t, J=7.42 Hz, 3H) 3.76 (s, 5H) 4.12 (q, J=7.15 Hz, 2H) 6.99 (m, 2H) 7.03 (s, 2H) 7.10 (m, 2H) 7.14

(s, 1H) 7.28 (dd, J=30.79, 8.80 Hz, 3H) 7.92 (s, 1H) 8.67 (s, 2H) 9.05 (s, 2H) 12.66 (s, 1H). HRMS calcd for $C_{26}H_{26}N_3O_3$: 428.1974. Found: 428.1968.

Example 4

2'-(6-Carbamimidoyl-1-isobutyl-1H-indol-3-ylmethyl)-4-methoxy-biphenyl-2-carboxylic acid Example 4 was prepared as its TFA salt from the compound of Example 1, Part B as described for Example 2 using isobutyl bromide in place of benzyl bromide. $^1$H NMR (500 MHz, DMSO-d6) δ ppm 0.82 (m, 6H) 2.15 (m, 1H) 3.82 (s, 5H) 3.95 (dd, J=7.42, 2.47 Hz, 2H) 7.00 (m, 1H) 7.05 (m, 1H) 7.08 (m, 1H) 7.15 (m, 3H) 7.21 (s, 1H) 7.35 (m, 3H) 7.98 (s, 1H) 8.73 (s, 2H) 9.10 (s, 21H) 12.73 (s, 1H). HRMS calcd for $C_{28}H_{30}N_3O_3$: 456.2287. Found: 456.2279.

Example 5

2'-(6-Carbamimidoyl-1-cyclopropylmethyl-1H-indol-3-ylmethyl)-4-methoxy-biphenyl-2-carboxylic acid Example 5 was prepared as its TFA salt from the compound of Example 1, Part B as described for Example 2 using cyclopropylmethyl bromide in place of benzyl bromide. $^1$H NMR (500 MHz, DMSO-d$_6$) δ ppm 0.36 (q, J=4.58 Hz, 2H) 0.49 (m, 2H) 1.27 (m, 1H) 3.81 (m, 5H) 3.99 (m, 2H) 7.09 (m, 6H) 7.26 (s, 1H) 7.36 (m, 3H) 8.03 (s, 1H) 8.72 (s, 2H) 9.09 (s, 2H) 12.71 (s, 1H). HRMS calcd for $C_{28}H_{28}N_3O_3$: 454.2131. found: 454.2132.

Example 6

2'-(6-Carbamimidoyl-1-pyridin-3-ylmethyl-1H-indol-3-ylmethyl)-4-methoxy-biphenyl-2-carboxylic acid Example 6 was prepared as its TFA salt from the compound of Example 1, Part B as described for Example 2 using 3-picolylchloride in place of benzyl bromide. $^1$HNMR (500 MHz, DMSO-6) δ 9.09 (s, 2H); 8.72 (s, 2H); 8.51 (m, 2H); 8.07 (m, 1H); 7.62 (m, 1H); 7.41 (m, 2H); 7.34 (m, 3H); 7.17 (m, 2H); 7.05 (m, 4H); 5.45 (s, 2H); 3.83 (m, 2H); 3.79. HRMS calcd. for $C_{30}H_{27}N_4O_3$: 491.2083. Found: 491.0613.

Example 7

3'-(1-Benzyl-6-carbamimidoyl-1H-indol-3-ylmethyl)-4-carbamoyl-biphenyl-2-carboxylic acid Part A. 3-(3-bromobenzyl)-1H-indole-6-carbonitrile: A solution of 6-cyanoindole (1.4 g, 9.85 mmol) and 3-bromobenzaldehyde (3.64 g, 19.7 mmol) in 50 mL MeOH was treated with sodium hydroxide (0.4 g, 9.85 mmol) and the resulting yellow solution stirred for 48 h at rt. Most of the solvent was then removed on rotary evaporator and the residue diluted with $CH_2Cl_2$, washed with water and brine and dried over $Na_2SO_4$, filtered and evaporated. Flash chromatography provide the intermediate hydroxyl compound (1.73 g, 54%) which was redissolved in 10 mL $CH_2Cl_2$ and treated with triethylsilane (0.73 ml, 10.6 mmol). The solution was cooled in ice bath and trifluoroacetic acid (1.51 ml, 7.9 mmol) was added dropwise. Stirring was continued for 1 h at rt then the reaction mixture was diluted with 10% $Na_2CO_3$ solution and phases separated. Aqueous was re-extracted 2× with $CH_2Cl_2$ then combined organic extracts were washed with water and brine, dried over $Na_2SO_4$, filtered and evaporated. Flash chromatography provide the product as a white solid (1.25 g, 76%). $^1$H NMR (500 MHz, CDCl$_3$) δ ppm 4.07 (s, 2H) 7.15 (m, J=7.15 Hz, 3H) 7.32 (m, 2H) 7.37 (s, 1H) 7.51 (d, J=8.25 Hz, 1H) 7.70 (s, 1H) 8.29 (s, 1H).

Part B. 1-benzyl-3-(3-Bromobenzyl)-1H-indole-6-carbonitrile: The compound of Part A (0.2 g, 0.64 mmol) was dissolved in 2 mL DMF with stirring under $N_2$ and cooled in an ice bath. Sodium hydride (60% in oil, 0.03 g, 0.71 mmol) was then added to the cold solution and the mixture was stirred for 10-15 min followed by addition of benzyl bromide (0.09 ml, 0.77 mmol). Stirring was continued for 1 h at 0° C. then overnight at rt. Reaction mixture was poured into water and extracted 3× with EtOAc. The combined extracts were washed with water and brine then dried over anhydrous $Na_2CO_3$, filtered and evaporated. Flash chromatography provided the product (0.124 g, 48%). $^1$H NMR (400 MHz, CDCl$_3$) δ ppm 4.07 (s, 2H) 5.30 (s, 2H) 7.08 (d, J=6.15 Hz, 3H) 7.15 (d, J=5.71 Hz, 2H) 7.33 (m, 6H) 7.51 (d, J=8.35 Hz, 1H) 7.57 (s, 1H).

Part C. 3'-(1-benzyl-6-cyano-1H-indol-3-ylmethyl)-4-carbamoyl-biphenyl-2-carboxylic acid benzyl ester: 2-Bromo-5-iodobenzoic acid (6.54 g, 20.0 mmol) was dissolved in DMF (70 mL). Potassium bicarbonate (2.2 g, 22.0 mmol) was added, followed by benzyl bromide (2.8 mL, 22.0 mmol). The mixture was stirred at rt under $N_2$ for 12 h. The reaction mixture was poured into water and extracted with EtOAc. The combined organic solution was washed with brine, dried over $MgSO_4$, and concentrated and dried to give 9.05 g of the benzyl ester. The ester (2.3 g, 7.69 mmol), $Zn(CN)_2$ (1.3 g, 11.5 mmol), and Pd[PPh$_3$]$_4$ were dissolved together in 25 mL of DMF. The mixture was de-gassed and heated at 90° C. for 4 h. Reaction mixture was concentrated and purified by chromatography (silica gel, 5% EtOAc in hexane) to give 1.8 g of the benzonitrile. MS: 316.0, 317.9 (M+1)$^+$. The benzonitrile (1.4 g, 4.4 mmol) was dissolved in 15 mL of DMF. The reaction mixture was cooled at 0° C. Potassium carbonate (0.20 g, 1.45 mmol) was added, followed by dropwise addition of 30% hydrogen peroxide solution (1.2 mL). The cooling bath was removed and the mixture was stirred at rt for 12 h. The reaction was quenched with aqueous NaHSO$_3$ and water. The formed precipitate was filtered and dried to give 1.1 g of the desired amide. MS: 334.2, 336.3 (M+1)$^+$. A mixture of the resulting amide (0.2 g, 0.6 mmole), bis(pinacolato)diboron (0.228 g, 0.9 mmol) and anhydrous KOAc (0.18 g, 1.8 mmol) in 2 mL of 1,4-dioxane was purged with argon, then (1,1')-bis(diphenylphosphino)ferrocene)palladium(II) chloride (20 mg, 0.024 mmol) was added. The resulting mixture was heated in a sealed tube in a microwave reactor at 100° C. for 2 h then left standing overnight at rt. The reaction was diluted with water and extracted 3× with EtOAc. The combined extracts were washed with brine, dried over $Na_2SO_4$, filtered and evaporated in vacuo. Chromatography on silica gel (hexane/ethyl acetate 1:1) provided the boronate (0.13 g, 57%). A mixture of this compound, the compound of Part B (0.1 g, 0.25 mmol), and K$_3$PO$_4$ (0.11 g, 0.5 mmol) in 5 mL dioxane was degassed and then treated with tetrakis (triphenylphosphine)palladium(20 mg, 0.017 mmol). The resulting mixture was heated in a 95-100° C. oil bath under $N_2$ for 2 h, then stirred at rt overnight. The reaction mixture was diluted with brine and extracted 3× with EtOAc. The combined extracts were washed with brine then dried over anhydrous $Na_2CO_3$, filtered and evaporated. Chromatography on silica gel (hexane/ethyl acetate 1:1) provided the product (0.12 g, 83%) as a light yellow foam. $^1$H NMR (400 MHz, CDCl$_3$) δ ppm 4.07 (s, 2H) 4.90 (s, 2H) 5.23 (s, 2H) 6.91 (d, J=6.15 Hz, 2H) 7.05 (m, 3H) 7.20 (m, 6H) 7.29 (m, 5H) 7.42 (d, J=7.91 Hz, 1H) 7.51 (d, J=10.99 Hz, 2H) 7.98 (dd, J=8.13, 1.98 Hz, 1H) 8.19 (d, J=2.20 Hz, 1H). LC/MS m/z 576.16 (M+H)+.

Part D. Example 7: The compound of Part C was converted to Example 7 which was isolated as its TFA salt using the procedure described in Example 1, Part D. $^1$HNMR (500 MHz, DMSO-$d_6$) δ ppm 4.14 (s, 2H) 5.45 (s, 2H) 7.15 (d, J=7.70 Hz, 1H) 7.21 (d, J=6.60 Hz, 2H) 7.26 (t, J=6.32 Hz, 2H) 7.30 (m, 4H) 7.39 (d, J=7.70 Hz, 1H) 7.43 (d, J=9.90 Hz, 1H) 7.50 (s, 1H) 7.65 (s, 1H) 7.70 (d, J=8.25 Hz, 1H) 8.01 (d, J=9.90 Hz, 1H) 8.08 (s, 1H) 8.14 (s, 1H) 8.20 (s, 1H) 8.75 (s, 2H) 9.11 (s, 2H) 12.95 (s, 1H). HRMS calcd. for $C_{31}H_{27}N_4O_3$: 503.2083. Found: 503.2101.

Example 8

3'-(6-Carbamimidoyl-1-ethyl-1H-indol-3-ylmethyl)-4-carbamoyl-biphenyl-2-carboxylic acid Example 8 was prepared as its TFA salt following the procedures described for Example 7 by replacing benzyl bromide with ethyl bromide. $^1$H NMR (500 MHz, DMSO-$d_6$) δ ppm 1.39 (t, J=7.15 Hz, 3H) 4.12 (s, 2H) 4.24 (q, J=7.15 Hz, 2H) 7.16 (d, J=7.70 Hz, 1H) 7.25 (d, J=7.70 Hz, 1H) 7.30 (m, 2H) 7.41 (m, J=7.15, 7.15 Hz, 2H) 7.50 (s, 1H) 7.57 (s, 1H) 7.68 (d, J=8.25 Hz, 1H) 8.01 (m, J=6.05 Hz, 2H) 8.14 (s, 1H) 8.20 (s, 1H) 8.75 (s, 2H) 9.13 (s, 2H) 12.97 (s, 1H). HRMS calcd. for $C_{26}H_{25}N_4O_3$: 441.1927. Found: 441.1915.

Example 9

3'-(6-Carbamimidoyl-1-ethyl-1H-indol-3-ylmethyl)-4-methoxy-biphenyl-2-carboxylic acid Part A. 1-ethyl-3-(2'-formyl-4'-methoxy-biphenyl-3-ylmethyl)-1H-indole-6-carbonitrile: 1-Ethyl-3-(3-Bromobenzyl)-1H-indole-6-carbonitrile (0.14 g, 0.43 mmol) was dissolved in a mixture of 5 mL toluene and 2 mL EtOH. To the solution was added 2-formyl-4-methoxyphenyl boronic acid (0.12 g, 0.64 mmol) and a 2M solution of sodium carbonate (0.43 ml, 0.86 mmol). The mixture was degassed and then tetrakis(triphenylphosphine)palladium (25 mg) was added. The reaction was heated at reflux in a 95° C. oil bath under $N_2$ overnight. Reaction was cooled to rt, diluted with EtOAc and washed with brine. The organic layer was dried over anh. $Na_2SO_4$, filtered and evaporated. Chromatography on silica gel (hexane/ethyl acetate 4:1) provided the product (0.15 g, 90%). $^1$H NMR (400 MHz, CDCl$_3$) δ ppm 1.46 (t, J=7.25 Hz, 3H) 3.88 (s, 3H) 4.15 (q, J=7.25 Hz, 2H) 7.08 (s, 1H) 7.18 (m, 3H) 7.33 (m, 4H) 7.47 (d, J=2.64 Hz, 1H) 7.53 (d, J=8.35 Hz, 1H) 7.64 (s, 1H) 9.89 (s, 1H).

Part B. Example 9 was prepared as its TFA salt from the compound of Part A as described for Example 1, Part C and D$^1$H NMR (500 MHz, DMSO-$d_6$) δ ppm 1.39 (t, J=7.15 Hz, 3H) 3.80 (m, 3H) 4.10 (s, 2H) 4.24 (q, J=7.15 Hz, 2H) 7.09 (m, 2H) 7.18 (m, 2H) 7.25 (m, 3H) 7.40 (d, J=8.80 Hz, 1H) 7.56 (s, 1H) 7.67 (d, J=8.25 Hz, 1H) 8.02 (s, 1H) 8.75 (s, 2H) 9.13 (s, 2H) 12.81 (s, 1H). HRMS calcd for $C_{26}H_{26}N_3O_3$: 428.1974. Found: 428.1963.

Example 10

2'-(6-Carbamimidoyl-1-methyl-1H-indol-3-ylmethyl)-4-methoxy-5'-methylcarbamoyl-biphenyl-2-carboxylic acid Part A. 3-bromo-4-formyl-benzoic acid tert-butyl ester: A solution of 3-bromo-4-methylbenzoic acid (5 g, 0.023 mol) in 40 mL toluene was heated to 80° C. in an oil bath and DMF-di-t-butylacetal (22.4 ml, 0.093 mol) was added dropwise over 20 min. The resulting mixture was heated for an additional 1 h and then cooled to rt and evaporated to dryness. Chromatography on silica gel (hexane/ethyl acetate 1:1) provided the t-butyl ester (5.1 g, 81%) which was dissolved in 50 mL CCl$_4$ and treated with N-bromosuccinimide (6.7 g, 0.037 mol) and benzoylperoxide (0.22 g, 0.94 mmol). The mixture was then heated in an 80° C. oil bath overnight. Solvent was removed by evaporation, and residue was taken up in EtOAc and washed with water, sat'd $Na_2CO_3$ and brine then dried over anh. $Na_2SO_4$, filtered and concentrated. Chromatography on silica gel (hexane/ethyl acetate 1:1) provided the dibromide (7.5 g, 94%) to which was added 30 mL morpholine and the mixture was heated overnight at 60° C. After cooling to rt, the mixture was diluted with EtOAc and washed with 5% citric acid solution until aqueous phase stays at pH 4, then with sat'd bicarbonate solution and brine. Organic phase was dried and concentrated to provide the aldehyde in 74% yield after flash chromatography. $^1$NMR (500 MHz, CDCl$_3$) δ 10.40 (s, 1H); 8.24 (s, 1H); 7.95 (m, 1H); 7.93 (m, 1H); 1.61 (s, 9H).

Part B. 3-bromo-4-(6-cyano-1-methyl-1H-indol-3-ylmethyl)-N-methyl-benzamide: 3-Bromo-4-(6-cyano-1-methyl-1H-indol-3-ylmethyl)-benzoic acid tert-butyl ester (prepared from the compound of Part A as described under Ex. 12, Part A by substituting methyl iodide for ethyl iodide) was stirred in a mixture of 2:1CH$_2$Cl$_2$/TFA for 1 h. Reaction was evaporated to dryness and crude acid dried in vacuo. A mixture of the acid (74 mg, 0.2 mmol), methylamine hydrochloride (27.2 mg, 0.4 mmol), NMM (0.16 g, 1.6 mmol), and BOP reagent (0.14 g, 0.32 mmol) in 1.5 mL DMF was stirred at rt under $N_2$ for 3 days. Reaction mixture was poured into water and extracted 3× with EtOAc. The combined extracts were washed with water and brine then dried over anhydrous $Na_2CO_3$, filtered and evaporated to provide the N-methylamide which was used without purification. LRMS m/z 381.9/383.9 (M+H)+.

Part C. Example 10: The compound of Part B was converted into Example 10 using the procedures of Example 9, Part A, Example 1, Part C and Example 2, Part C. $^1$HNMR (500 MHz, DMSO-d6) δ 9.12 (s, 2H); 8.72 (s, 2H); 8.35 (m, 1H); 7.98 (s, 1H); 7.64 (m, 1H); 7.56 (m, 1H); 7.43 (m, 1H); 7.33 (m, 2H); 7.20 (2, 1H); 7.14 (s, 2H); 7.10 (m, 1H); 3.83 (m, 5H); 3.78 (2, 3H); 2.73 (m, 3H). HRMS calcd. for $C_{27}H_{27}N_4O_4$: 471.2032. Found: 471.2018.

Example 11

2'-(6-Carbamimidoyl-1-ethyl-1H-indol-3-ylmethyl)-4-methoxy-5'-methylcarbamoyl-biphenyl-2-carboxylic acid Example 11 was prepared in a similar manner as described for Example 12 by substituting methylamine hydrochloride for the 2-aminomethylpyridine in Example 12, Part B. $^1$HNMR (500 MHz, DMSO-6) δ 9.11 (2, 2H); 8.72 (s, 2H); 8.35 (m, 1H); 7.99 (s, 1H); 7.63 (m, 1H); 7.55 (m, 1H); 7.43 (s, 1H); 7.34 (m, 1H); 7.32 (m, 1H); 7.21 (s, 1H); 7.13 (m, 3H); 41.8 (q, 2H); 3.85 (m, 2H); 3.83 (s, 3H); 2.73 (m, 3H); 1.36 (t, 3H). HRMS calcd for $C_{28}H_{29}N_4O_4$: 485.2189. Found: 485.2195.

Example 12

2'-(6-Carbamimidoyl-1-ethyl-1H-indol-3-ylmethyl)-4-methoxy-5'-[(pyridine-2-ylmethyl)-carbamoyl]-biphenyl-2-carboxylic acid Part A. 3-bromo-4-(6-cyano-1-ethyl-1H-indol-3-ylmethyl)-benzoic acid tert-butyl ester: A mixture of the compound of Example 10, Part A (5 g, 0.175 mol) and 6-cyanoindole (1.7 g, 0.0.12 mol) in t-butanol (60 ml) and THF (~5 mL) was treated with potassium t-butoxide (0.012 mol) and the mixture was stirred at rt under $N_2$. After 18 h the reaction mixture was diluted with EtOAc and washed with water and brine, dried over anh. $Na_2SO_4$, filtered and solvent evaporated. The residue was purified by flash chromatography on silica gel to provide 3-Bromo-4-[(6-cyano-1H-indol-3-yl)-hydroxy-methyl]-benzoic acid tert-butyl ester (4.05 g, 79%) as an off-white foam. $^1$H NMR (400 MHz, $CDCl_3$) δ ppm 1.58 (s, 9H) 2.43 (d, J=0.39 Hz, 1H) 6.47 (d, J=0.39 Hz, 1H) 7.11 (d, J=2.20 Hz, 1H) 7.36 (d, J=8.35 Hz, 1H) 7.70 (s, 1H) 7.78 (dd, J=15.60, 8.13 Hz, 2H) 7.98 (m, 1H) 8.14 (s, 1H) 8.39 (s, 1H). This material was dissolved in methylene chloride (55 ml) and cooled in an ice/salt water bath under $N_2$. To the cold, stirred solution was added triethylsilane (3.03 mL, 2 eq) followed by slow addition of trifluoroacetic acid (0.72 mL, 1 eq) over 20-25 min. The resulting solution was stirred for 1 h allowing ice bath to melt and reaction to gradually assume rt. Additional methylene chloride was added and the solution was washed with brine, dried and evaporated.

Chromatography on silica gel provided 3-bromo-4-(6-cyano-1H-indol-3-ylmethyl)-benzoic acid tert-butyl ester (2.72 g, 70%) as a white solid. $^1$H NMR (400 MHz, $CDCl_3$) δ ppm 1.57 (s, 9H) 4.24 (s, 2H) 7.16 (m, 2H) 7.32 (d, J=8.35 Hz, 1H) 7.55 (d, J=8.35 Hz, 1H) 7.71 (s, 1H) 7.79 (dd, J=7.91, 1.76 Hz, 1H) 8.18 (d, J=1.76 Hz, 1H) 8.33 (s, 1H). A solution of this intermediate (6.56 mmol) in DMF (30 mL) was cooled in an ice bath with stirring under $N_2$. To the cold solution was added sodium hydride (0.3 g, 60% in oil, 7.5 mmol), and the mixture was stirred for 15 min followed by addition of ethyl iodide (0.66 mL, 8.25 mmol). Stirring was continued overnight allowing the reaction to gradually assume room temperature. The resulting mixture was diluted with water and extracted 3× with EtOAc. Combined extracts were washed with water and brine then dried over anh. $Na_2SO_4$, filtered and solvent evaporated. The residue was chromatographed on silica gel to proved the alkylated product (2.16 g, (75%) as an off-white foam. $^1$H NMR (400 MHz, $CDCl_3$) δ ppm 1.45 (t, J=7.25 Hz, 3H) 1.57 (s, 9H) 4.15 (q, J=7.47 Hz, 2H) 4.22 (s, 2H) 7.04 (s, 1H) 7.18 (d, J=7.91 Hz, 1H) 7.29 (d, J=7.91 Hz, 1H) 7.53 (d, J=7.91 Hz, 1H) 7.66 (s, 1H) 7.80 (m, 1H) 8.18 (s, 1H).

Part B. 3-bromo-4-(6-cyano-1-ethyl-1H-indol-3-ylmethyl)-N-pyridin-2-ylmethyl-benzamide: The compound of Part A was dissolved in methylene chloride (5 mL) and trifluoroacetic acid (1.25 mL) was added. The resulting solution was stirred at room temperature under $N_2$ overnight. Reaction mixture was then diluted with additional methylene chloride and washed 3× with water, then dried over anh. $Na_2SO_4$, filtered and solvent evaporated to leave a lt pink solid which was dried in vacuo and used with purification for conversion to the amide. A mixture of the acid (0.26 g, 0.68 mmol), 2-aminomethylpyridine (85 µL, 1.2 eq), NMM (0.35 mL, 5 eq) and BOP (0.45 g, 1.5 eq) in DMF (5 mL) was stirred at room temperature under $N_2$ for 2 days. Reaction mixture was diluted with water and extracted 3× with EtOAc. Combined extracts were washed with water, sat'd. $NaHCO_3$, and brine, then dried over $Na_2SO_4$, filtered and evaporated. Flash chromatography on silica gel provided the pyridylmethylamide (0.23 g, 71%).

Part C. Example 12: The compound of Part B was coupled to 2-formyl-4-methoxyphenylboronic acid using the procedure outlined under Example 9, Part A. The resulting aldehyde was oxidized to the corresponding acid by the procedure of Example 1, Part C. Finally the nitrile group was converted to the corresponding amidine by the procedure described under Example 1, Part D to give Example 12. $^1$H NMR (500 MHz, DMSO-d6) δ ppm 1.35 (t, J=7.39 Hz, 3H) 3.83 (s, 3H) 3.87 (d, J=6.05 Hz, 2H) 4.18 (q, J=7.39 Hz, 2H) 4.55 (d, J=6.05 Hz, 2H) 7.13 (s, 2H) 7.17 (d, J=8.07 Hz, 1H) 7.21 (s, 1H) 7.34 (m, 4H) 7.66 (s, 1H) 7.73 (m, J=10.08 Hz, 2H) 7.84 (m, 1H) 7.99 (s, 1H) 8.53 (d, J=5.38 Hz, 1H) 8.74 (s, 2H) 9.09 (t, J=5.71 Hz, 1H) 9.11 (s, 2H). HRMS calcd for $C_{33}H_{32}N_5O_4$: 562.2454. Found: 562.2445.

Example 15

2'-(6-Carbamimidoyl-1-ethyl-1H-indol-3-ylmethyl)-4-methoxy-5'-[(pyridin-3-ylmethyl)-carbamoyl]-biphenyl-2-carboxylic acid, bis trifluoroacetic acid salt Part A. 3-bromo-4-[(6-cyano-1H-indol-3-yl)-hydroxy-methyl]-benzoic acid tert-butyl ester: A mixture of the compound of Example 10, Part A (3.4 g, 0.012 mol) and 6-cyanoindole (1.1 g, 0.0077 mol) was dissolved in 40 mL t-BuOH and potassium t-butoxide (0.87 g, 0.0077 mol) was added. The reaction mixture was stirred at rt under $N_2$ overnight. Resulting mixture was diluted with EtOAc and washed with water and brine then dried over anhydrous $Na_2SO_4$, filtered and evaporated. Chromatography on silica gel (hexane EtOAc 4:1 then 1:1) provided the desired product (3.2 g, 96%). $^1$H NMR (400 MHz, $CDCl_3$) δ ppm 1.58 (s, 9H) 2.43 (d, J=4.39 Hz, 1H) 6.47 (d, J=4.39 Hz, 1H) 7.11 (d, J=2.20 Hz, 1H) 7.36 (d, J=8.35 Hz, 1H) 7.70 (s, 1H) 7.78 (dd, J=15.60, 8.13 Hz, 2H) 7.98 (m, 1H) 8.14 (s, 1H) 8.39 (s, 1H).

Part B. 3-bromo-4-(6-cyano-1H-indol-3-ylmethyl)-benzoic acid tert-butyl ester: The compound of Part A (1.00 eq, 8 mmol, 3.43 g) was dissolved in dichloromethane (35 mL) and stirred under $N_2$ with cooling in an ice bath. To the cold solution was added triethylsilane (16 mmol, 2.57 mL) followed by slow dropwise addition of trifluoroacetic acid (8 mmol, 0.61 mL) over 15 min. The resulting yellow solution was stirred for 1 h allowing the ice to melt and the reaction to assume rt. Reaction was quenched by addition of 10% $Na_2CO_3$ and phases were separated. Organic layer was washed with brine, dried over anhydrous $Na_2CO_3$, filtered and evaporated. Residue was chromatographed on silica gel eluted with hexane-EtOAc 85:15 followed by hexane-EtOAc 80:20 to provide the product (2.22 g, 67%). $^1$H NMR (400 MHz, $CDCl_3$) δ ppm 1.57 (s, 9H) 4.24 (s, 2H) 7.16 (m, 2H) 7.32 (d, J=8.35 Hz, 1H) 7.55 (d, J=8.35 Hz, 1H) 7.71 (s, 1H) 7.79 (dd, J=7.91, 1.76 Hz, 1H) 8.18 (d, J=1.76 Hz, 1H) 8.33 (s, 1H).

Part C. 3-bromo-4-(6-cyano-1-ethyl-1H-indol-3-ylmethyl)-benzoic acid tert-butyl ester: The compound of Part B (1.00 eq, 5.35 mmol, 2.20 g) was dissolved in Dimethylformamide (20 mL) and cooled in an ice bath with stirring under $N_2$. To the cold solution was added sodium hydride (60% in oil, 5.88 mmol, 235 mg) and the mixture was stirred for 10-15 min to obtain a clear solution. Ethyl bromide (6.42 mmol, 0.48 mL) was then added in one portion and the mixture was stirred in an ice bath for ~1 h then at rt overnight. Reaction was diluted with water and extracted 3× with EtOAc. Combined extracts were washed with water (2×) then brine, dried over anh. $Na_2SO_4$, filtered and evaporated. Chromatography on silica gel eluted with hexane/EtOAc 85:15 provided the alkylated product (1.90 g; 80.8% yield). $^1$H NMR (400 MHz, $CDCl_3$) δ ppm 1.45 (t, J=7.25 Hz, 3H) 1.57 (s, 9H) 4.15 (q, J=7.47 Hz, 2H) 4.22 (s, 2H) 7.04 (s, 1H) 7.18 (d, J=7.91 Hz, 1H) 7.29 (d, J=7.91 Hz, 1H) 7.53 (d, J=7.91 Hz, 1H) 7.66 (s, 1H) 7.80 (m, 1H) 8.18 (s, 1H).

Part D. 6-(6-cyano-1-ethyl-1H-indol-3-ylmethyl)-2'-formyl-4'-methoxy-biphenyl-3-carboxylic acid tert-butyl ester: The compound of Part C was coupled to 2-formyl-4-methoxyphenylboronic acid using the procedure described for Example 9, Part A to provide the desired product, which was used without purification in step E below.

Part E. 6'-(6-cyano-1-ethyl-1H-indol-3-ylmethyl)-4-methoxy-biphenyl-2,3'-dicarboxylic acid 2-benzyl ester 3'-tert-butyl ester: The aldehyde of Part D was oxidized to the corresponding carboxylic acid using the procedure of Example 1, Part C and the resulting crude acid (1.24 g, 2.43 mmol) was dissolved in DMF (10 mL) and treated with $KHCO_3$ (0.3 g, 2.92 mmol) and benzyl bromide (0.35 ml, 2.92 mmol) followed by stirring overnight at rt. The reaction was diluted with water and extracted with EtOAc. The extracts were washed with brine, dried and evaporated. Silica gel chromatography using a gradient from 0-40% EtOAc in hexane provided the benzyl ester (1.17 g, 80%). $^1$HNMR (500 MHz, $CDCl_3$) δ 1.40 (t, J=7.1 Hz, 3H); 1.57 (s, 9H); 3.78 (m, 2H); 3.87 (s, 3H); 4.04 (q, J=7.1 Hz, 2H); 4.98 (m, 2H); 6.66 (s, 1H); 6.99 (s, 2H); 7.02 (m, 2H); 7.17 (m, 2H); 7.22 (m, 4H); 7.56 (m, 2H); 7.69 (s, 1H); 7.81 (m, 1H).

Part F. 6'-(6-cyano-1-ethyl-1H-indol-3-ylmethyl)-4-methoxy-biphenyl-2,3'-dicarboxylic acid 2-benzyl ester: The compound of Part E was dissolved in a 4:1 mixture of methylene chloride and TFA at 0° C. and then stirred overnight at rt. Reaction mixture was stripped to dryness on a rotary evaporator, and product used without purification in step G below.

Part G. 2'-(6-cyano-1-ethyl-1H-indol-3-ylmethyl)-4-methoxy-5'-[(pyridin-3-ylmethyl)-carbamoyl]-biphenyl-2-carboxylic acid benzyl ester: A mixture of the acid from Part F, (0.19 g, 0.18 mmol), 3-aminomethylpyridine (28 μL, 0.28 mmol), N-methylmorpholine (0.16 mL, 1.47 mmol) and BOP reagent (0.1 g, 0.23 mmol) in DMF (1 mL) was stirred at rt overnight under $N_2$. The reaction was diluted with water and extracted with EtOAc. The extracts were washed with brine, dried and evaporated. Silica gel chromatography provided the amide (0.1 g, 86%). LC/MS m/z 635.4 $(M+H)^+$.

Part H. Example 15: The compound of Part G was converted to Example 15 in 77% yield as described in Example 1, Part D. $^1$HNMR (500 MHz, DMSO-d6) δ 9.09 (s, 2H); 9.05 (s, 1H); 8.71 (s, 2H); 8.61 (s, H); 8.54 (m, 1H); 7.98 (s, 1H); 7.92 (bs, 1H); 7.71 (m, 1H); 7.61 (m, 1H); 7.53 (m, 1H); 7.44 (m, 1H); 7.33 (m, 2H); 7.17 (m, 2H); 7.11 (m, 2H); 4.49 (m, 2H); 4.17 (m, 2H); 3.86 (m, 2H); 3.82 (s, 3H); 1.35 (t, J=7.2 Hz, 3H). HRMS calcd for $C_{33}H_{32}N_5O_4$: 562.2454. Found: 562.2450.

Example 16

2'-(6-Carbamimidoyl-1-ethyl-1H-indol-3-ylmethyl)-4-methoxy-5'-[(pyridin-4-ylmethyl)-carbamoyl]-biphenyl-2-carboxylic acid, bistrifluoroacetic acid salt Example 16 was prepared as described for Example 15 using 4-aminomethylpyridine in place of 3-aminomethylpyridine. $^1$HNMR (500 MHz, DMSO-d6) δ 9.15 (m, 1H); 9.10 (s, 2H); 8.74 (s, 2H); 8.62 (m, 2H); 7.99 (s, 1H); 7.73 (m, 1H); 7.65 (m, 1H); 7.54 (m, 1H); 7.4 (s, 1H); 7.35 (m, 2H); 7.20 (m, 2H); 7.12 (m, 2H); 4.55 (m, 2H0; 4.18 (m, 2H0; 3.88 (m, 2H); 3.83 (s, 3H); 1.36 (t, J=7.2, 3H). HRMS calcd for $C_{33}H_{32}N_5O_4$: 562.2454. Found: 562.2445.

Example 19

2'-(6-Carbamimidoyl-1-ethyl-1H-indol-3-ylmethyl)-biphenyl-2-carboxylic acid

Part A. 1-ethyl-3-[2-(4,4,5,5-tetramethyl-1,3,2-dioxaborolan-2-yl)-benzyl]-1H-indole-6-carbonitrile: To a round-bottomed flask equipped with a condenser was added Pd(dppf) $Cl_2CH_2Cl_2$ complex (0.122 g, 0.15 mmol), KOAc (1.472 g, 15 mmol), bis(pinacolato)diboron (6.983 g, 27.5 mmol), 1-ethyl-3-(2-bromobenzyl)-1H-indole-6-carbonitrile (prepared from the compound of Example 1, Part A following the procedure described under Example 2, Part A) (1.696 g, 5 mmol), and DMSO (30 mL). The mixture was degassed by bubbling argon for 10 min, then stirred at 80° C. for 4 h. The reaction mixture was cooled to rt, diluted with EtOAc (100 mL), washed with water (50 mL), brine (50 mL), dried over $Na_2SO_4$, filtered and concentrated. Chromatography on silica gel gave 1.14 g (59%) of product as an off-white solid. The impure fractions were repurified as above to give 0.68 g (35%) of product as an off-white solid. Both lots were combined to give 1.82 g (94%). $^1$H NMR (500 MHz, $CDCl_3$) δ 1.18 (s, 12H), 1.40 (t, J=7.4 Hz, 3H), 4.09 (q, J=7.4 Hz, 2H), 4.37 (s, 2H), 6.84 (s, 1H), 7.21-7.36 (m, 4H), 7.61 (s, 1H), 7.67 (d, J=8.3 Hz, 1H), 7.81 (d, J=7.7 Hz, 1H). HRMS calc'd for: $C_{24}H_{28}BN_2O_2$ $(M+H)^+$: 387.2244. Found: 387.2260.

Part B. 2'-(6-cyano-1-ethyl-1H-indol-3-ylmethyl)-biphenyl-2-carboxylic acid ethyl ester: To a round-bottomed flask was added the compound of Part A (0.348 g, 0.9 mmol), ethyl 2-bromobenzoate (0.227 g, 0.99 mmol), $K_3PO_4$ (0.477 g, 2.25 mmol) and 1,4-dioxane (15 mL). The mixture was degassed by bubbling argon for 10 min. Next tetrakis(triphenylphosphine)palladium(0) (0.042 g, 0.036 mmol) was added and the reaction was stirred at 95° C. for 24 h. After cooling the reaction to rt, it was diluted with EtOAc (100 mL), washed with water (50 mL), brine (50 mL), dried over $Na_2SO_4$, filtered and concentrated. Chromatography on silica gel gave 0.2 g (55%) of product as a white solid. $^1$H NMR (400 MHz, $CDCl_3$) δ0.90 (t, J=7.0 Hz, 3H), 1.39 (t, J=7.2 Hz, 3H), 3.81-4.01 (m, 4H), 4.05 (q, J=7.2 Hz, 2H), 6.99 (s, 1H), 7.08-7.46 (m, 9H), 7.57 (s, 1H), 7.94-7.96 (m, 1H). HRMS calc'd for $C_{27}H_{25}N_2O_2$ $(M+H)^+$: 409.1916. Found: 409.1931.

Part C. Example 19: To a suspension of compound from Part B (0.203 g, 0.5 mmol) in MeOH (5 mL) was added 1.0 N NaOH (2 mL, 2 mmol). The mixture was stirred at 80° C. for 3 h to give a clear solution. The reaction mixture was cooled to rt and concentrated to dryness. The residue was partitioned between 1.0 N HCl (2.5 mL, 2.5 mmol) and EtOAc (40 mL). The layers were separated and the organic layer was washed with brine, dried over $Na_2SO_4$, filtered and concentrated to give 0.19 g of the carboxylic acid as an off-white solid. The acid (0.075 g) was dissolved in EtOH (3 mL) and the solution was cooled to 0° C. Into this solution was bubbled HCl gas for 10 min. The vessel was sealed with a rubber septum and the reaction was stirred at rt for 16 h. The reaction mixture was concentrated to dryness and then the residue was dissolved in EtOH (3 mL). To this solution was added $NH_4OAc$ (0.228 g, 3 mmol), and the resulted solution was stirred at rt for 24 h. The reaction mixture was concentrated, and the residue was purified by C18 Prep. HPLC to yield 0.052 g (51%) of Example 19 as its TFA salt. $^1$H NMR (400 MHz, $CD_3OD$) δ 1.32 (t, J=7.2 Hz, 3H), 3.82 (s, 2H), 4.09 (q, J=7.2 Hz, 2H), 6.86-6.97 (m, 3H), 7.11-7.29 (m, 6H), 7.76 (d, J=2.2 Hz, 1H), 7.78 (d, J=1.3 Hz, 1H). HRMS calcd. for $C_{25}H_{23}ClN_3O_2$: 432.1479. Found: 432.1483.

Example 25

6-(6-Carbamimidoyl-1-ethyl-1H-indol-3-ylmethyl)-2'-hydroxymethyl-4'-methoxy-biphenyl-3-carboxylic acid (pyridin-2-ylmethyl)-amide Part A. 3-bromo-4-(6-cyano-1-ethyl-1H-indol-3-ylmethyl)-benzoic acid: The compound of Example 15, Part C was dissolved in a 1:1 mixture of methylene chloride and trifluoroacetic acid then stirred for 1 h at rt. Evaporation to dryness, trituration with ether and drying in vacuo provided the acid which was used in Part B without further purification.

Part B. 3-bromo-4-(6-cyano-1-ethyl-1H-indol-3-ylmethyl)-N-pyridin-2-ylmethyl-benzamide: A mixture of the compound of Part A (0.18 g, 0.47 mmol), 2-aminomethylpyridine (0.058 mL, 0.56 mmol), NMM (0.4 mL, 3.8 mmol) and BOP reagent (0.26 g, 0.59 mmol) in DMF (1.5 mL) was stirred overnight at rt. Reaction mixture was diluted with water and extracted with EtOAc. Organic layer was washed with brine, dried over anh. $Na_2SO_4$, filtered and evaporated. Chromatography on silica gel provided the amide product (0.2 g, 91%). LC/MS m/z 473.2, 475.2 $(M+H)^+$.

Part C. 6-(6-cyano-1-ethyl-1H-indol-3-ylmethyl)-2'-formyl-4'-methoxy-biphenyl-3-carboxylic acid (pyridin-2-ylmethyl)-amide: The compound of Part B (0.2 g, 0.42 mmol) and 2-formyl-4-methoxyphenylboronic acid (0.11 g, 0.64 mmol) were dissolved in dioxane (10 mL) and potassium phosphate (0.22 g, 1.06 mmol) was added. The mixture was degassed followed by addition of tetrakis(triphenylphosphine)palladium(0) (20 mg, 0.016 mmol). The resulting mixture was heated in a 95° C. oil bath overnight under $N_2$. Reaction was cooled to rt, diluted with EtOAc, and washed with water and brine. Organic layer was dried over anh. $Na_2SO_4$, filtered and evaporated. Flash chromatography on silica gel provided the product (0.18 g, 82%). LC/MS m/z 529.2 $(M+H)^+$.

Part D. 6-(6-cyano-1-ethyl-1H-indol-3-ylmethyl)-2'-hydroxymethyl-4'-methoxy-biphenyl-3-carboxylic acid (pyridin-2-ylmethyl)-amide: The compound of Part C (80 mg, 0.15 mmol) was dissolved in MeOH (1 mL), and sodium borohydride (5.7 mg, 0.15 mmol) was added in one portion. After stirring for 1 h, an additional 0.5 eq of sodium borohydride was added, and the mixture was stirred for an additional 30 min. Reaction was quenched with water, methanol removed on rotary evaporator and aqueous extracted with EtOAc. The organic layer was washed with brine, dried over $Na_2SO_4$, filtered and evaporated. Flash chromatography on silica gel provided the alcohol (57 mg, 71%). LC/MS m/z 531.4 $(M+H)^+$.

Part E. 6-(6-carbamimidoyl-1-ethyl-1H-indol-3-ylmethyl)-2'-hydroxymethyl-4'-methoxy-biphenyl-3-carboxylic acid (pyridin-2-ylmethyl)-amide: The compound of Part D was converted to the title compound in ~60% yield using the procedures described under Example 1, Part D. $^1$HNMR (500 MHz, DMSO-d6) δ 1.3 (m, 3H); 3.78 (m, 4H); 3.87 (m, 2H); 4.13 (m, 3H); 4.53 (m, 2H); 6.84 (m, 1H); 7.02 (m, 1H, 0.08 (m, 1H); 7.14 (m, 1H); 7.32 (m, 5H); 7.65 (m, 1H); 7.76 (m, 1H); 7.81 (m, 1H); 7.98 (m, 1H); 8.52 (m, 1H); 8.70 (s, 2H); 9.08 (m, 3H). LC/MS m/z 548.4 $(M+H)^+$. HRMS calcd for $C_{33}H_{34}N_5O_3$: 548.2662. Found: 548.2643.

Example 26

2'-(6-Carbamimidoyl-1-ethyl-1H-indol-3-ylmethyl)-4-chloro-biphenyl-2-carboxylic acid Coupling of the compound from Example 19, Part A and 2-Bromo-5-chloro-benzoic acid methyl ester using the procedure from Example 19, Part B gave the biphenyl derivative which was converted to Example 26, as the TFA salt, using the procedure from Example 47, Part C $^1$H NMR (400 MHz, $CD_3OD$) δ 1.32 (t, J=7.2 Hz, 3H), 3.82 (s, 2H), 4.09 (q, J=7.2 Hz, 2H), 6.86-6.97 (m, 3H), 7.11-7.29 (m, 6H), 7.76 (d, J=2.2 Hz, 1H), 7.78 (d J=1.3 Hz, 1H). HRMS calc'd for $C_{25}H_{23}ClN_3O_2$ $(M+H)^+$: 432.1479. Found: 432.1483.

Example 28

2'-(6-Carbamimidoyl-1-ethyl-1H-indol-3-ylmethyl)-5'-(ethylcarbamoylmethyl-carbamoyl)-4-methoxy-biphenyl-2-carboxylic acid and

Example 29

2'-(6-Carbamimidoyl-1-ethyl-1H-indol-3-ylmethyl)-4-methoxy-5'-[(oxazol-2-ylmethyl)-carbamoyl]-biphenyl-2-carboxylic acid Part A. 2'-(6-cyano-1-ethyl-1H-indol-3-ylmethyl)-4-methoxy-5'-[(oxazol-2-ylmethyl)-carbamoyl]-biphenyl-2-carboxylic acid: A mixture of the compound of Example 15, Part F (75 mg, 0.138 mmol), oxazol-2-yl-methylamine hydrochloride (28 mg, 0.208 mmol) NMM (0.012 mL, 1.10 mmol) and BOP reagent (76 mg, 0.172 mmol) in DMF (1 mL) was stirred at rt over 3 days. Reaction was worked up and product isolated as described for Example 15, Part G to provide the amide (78.3 mg, 91%). LC/MS m/z 625.3 $(M+H)^+$.

Part B. Example 28 and Example 29: The compound of Part A was converted to the amidine using the procedure described for Example 1, Part D. The reduction resulted in the formation of two products which were separated by C18 HPLC to provide the oxazolyl compound (Example 29-22 mg, 26%) along with ring opened N-ethylcarbonyl analog (Example 28-24.5 mg, 29%). Example 28: $^1$HNMR (500 MHz, DMSO-d6) δ 9.10 (s, 2H); 9.06 (m, 1H); 8.71 (s, 2H); 8.01 (s, 1H); 7.98 (s, 1H); 7.70 (m, 1H); 7.63 (m, 1H); 7.44 (m, 1H); 7.32 (m, 2H); 7.21 (s, 1H); 7.16 (m, 1H); 7.12 (m, 3H); 4.53 (m, 2H); 4.18 (m, 2H); 3.86 (m, 2H); 3.83 (s, 3H), 1.36 (t, J=7.2 Hz, 3H). LC/MS m/z 552.3 $(M+H)^+$. HRMS calcd for $C_{31}H_{20}N_5O_5$: 552.2247. Found: 552.2264. Example 29: $^1$HNMR (500 MHz, DMSO-d6) δ 9.10 (s, 2H); 8.71 (s, 2H); 8.60 (m, 1H); 7.98 (s, 1H); 7.88 (m, 1H); 7.70 (m, 1H); 7.61 (m, 1H); 7.45 (m, 1H); 7.33 (m, 2H); 7.21 (s, 1H); 7.12 (m, 3H); 4.18 (m, 2H); 3.86 (m, 2H); 3.83 (s, 3H); 3.78 (m, 2H); 3.06 (m, 2H); 1.35 (t, J=7.4 Hz, 3H) 0.99 (t, J=7.1 Hz, 3H). LC/MS m/z 556.4 $(M+H)^+$. HRMS calcd for $C_{31}H_{34}N_5O_5$: 556.2560. Found: 556.2549.

Example 33

2'-(6-Carbamimidoyl-1-ethyl-1H-indol-3-ylmethyl)-4-methoxy-5'-[(1H-[1,2,4]triazol-3-ylmethyl)-carbamoyl]-biphenyl-2-carboxylic acid Part A. 3-aminomethyltriazole acetate: To a solution of 3-cyanotriazole (0.5 g, 5.3 mmol) in 13 ml 1:1 EtOAc/HOAc was added 75 mg 5% Pd/C and the mixture was stirred under 1 atm of $H_2$ overnight. The catalyst was removed by filtration and filtrate evaporated. Residue was triturated with $Et_2O$ and dried in vacuo. The crude amine salt was used without purification.

Part B. 2'-(6-cyano-1-ethyl-1H-indol-3-ylmethyl)-4-methoxy-5'-[(1H-[1,2,4]triazol-3-ylmethyl)-carbamoyl]-biphenyl-2-carboxylic acid: To a solution of the compound of Example 15, Part F (0.15 g, 0.278 mmol) and 3-aminomethyltriazole acetate (65 mg, 0.414 mmol) in DMF (2 mL) was added NMM (0.24 mL, 2.2 mmol) and BOP reagent (0.18 g, 0.414 mmol) and the mixture was stirred at rt overnight. An additional 1 eq of the amine, NMM and BOP reagent were added and stirring was continued for 3 days. Reaction was worked up as described for Example 15, Part G. Flash chromatography provided the product (54.8 mg, 32%). LC/MS m/z 625.2 (M+H)$^+$.

Part C. Example 33: The compound of Part B was converted into the title compound in ~50% yield following the procedures outlined in Example 1, Part D. $^1$HNMR (500 MHz, DMSO-d6) δ 9.11 (s, 2H), 8.84 (bs, 1H); 8.71 (s, 2H); 7.99 (s, 1H); 7.70 (m, 1H); 7.64 (2, 1H); 7.45 (m, 1H); 7.34 (m, 2H); 7.21 (m, 1H); 7.12 (m, 3H); 4.50 (m, 2H); 4.19 (m, 2H); 3.86 (m, 2H); 3.83 (s, 3H); 1.37 (t, J=7.4 Hz, 3H). LC/MS m/z 552.3 (M+H)$^+$. HRMS calcd for C30H30N7O4: 552.2359. Found: 552.2341.

Example 36

2'-(6-Carbamimidoyl-1-ethyl-1H-indol-3-ylmethyl)-5'-(ethylcarbamoylmethyl-carbamoyl)-4-methyl-biphenyl-2-carboxylic acid Part A. 5'-(tert-butoxycarbonylmethyl-carbamoyl)-2'-(6-cyano-1-ethyl-1H-indol-3-ylmethyl)-4-methyl-biphenyl-2-carboxylic acid benzyl ester: A mixture of the compound of Example 37, Part D (0.25 g., 0.47 mmol), t-butyl glycine (70 mg, 0.53 mmol), NMM (0.15 ml, 1.4 mmol) and BOP reagent (0.32 g, 0.72 mmol) in DMF (3 ml) was stirred for 48 h at rt under $N_2$. The reaction was then diluted with water and extracted 3× with EtOAc. The extracts were combined, washed with 5% citric acid, saturated NaHCO$_3$ and brine, then dried over anhydrous Na$_2$SO$_4$, filtered and evaporated. Purification by flash chromatography on silica gel (gradient from 0-50% EtOAc in hexane) provided the product (0.25 g, 79.5%).

Part B. 5'-(carboxymethyl-carbamoyl)-2'-(6-cyano-1-ethyl-1H-indol-3-ylmethyl)-4-methyl-biphenyl-2-carboxylic acid benzyl ester: The compound of Part A was dissolved in methylene chloride (~3 mL) and treated with TFA (2 mL). The resulting solution was stirred overnight at rt under $N_2$ overnight. Reaction was evaporated to dryness, and residue triturated with diethyl ether. Oily residue was redissolved in methylene chloride and evaporated to give the product as a foam which was used without purification in Part C below. $^1$H NMR (500 MHz, CDCl$_3$) δ ppm 1.37 (t, J=7.15 Hz, 3H) 2.41 (s, 3H) 3.78 (s, 2H) 4.03 (q, J=7.33 Hz, 2H) 4.22 (m, J=12.37, 5.22 Hz, 2H) 4.94 (m, 2H) 6.55 (s, 1H) 6.67 (s, 1H) 6.98 (s, 1H) 7.04 (d, J=5.50 Hz, 2H) 7.17 (m, 2H) 7.25 (m, 5H) 7.48 (s, 1H) 7.56 (s, 1H) 7.64 (d, J=6.05 Hz, 1H) 7.82 (s, 1H).

Part C. 2'-(6-cyano-1-ethyl-1H-indol-3-ylmethyl)-5'-(ethylcarbamoylmethyl-carbamoyl)-4-methyl-biphenyl-2-carboxylic acid benzyl ester: The compound of Part B was dissolved in DMF (1 mL) and ethylamine hydrochloride (31 mg, 0.38 mmol), NMM (0.1 ml, 0.9 mmol) and BOP reagent (0.11 g, 0.25 mmol) were added. The resulting mixture was stirred for 48 h at rt under $N_2$. Workup was as described under Example 15, Part G and provided the ethylamide product as a foam (27 mg, 35.5%). $^1$H NMR (500 MHz, CDCl$_3$) δ ppm 1.15 (t, J=7.15 Hz, 3H) 1.37 (t, J=7.42 Hz, 3H) 2.41 (s, 3H) 3.31 (dd, J=13.75, 6.60 Hz, 2H) 3.77 (s, 2H) 4.02 (m, 4H) 4.96 (m, 2H) 6.66 (s, 1H) 6.71 (t, J=5.22 Hz, 1H) 6.98 (s, 1H) 7.05 (m, 2H) 7.17 (dd, J=12.92, 7.97 Hz, 2H) 7.24 (m, 6H) 7.51 (s, 1H) 7.56 (s, 1H) 7.64 (d, J=6.05 Hz, 1H) 7.83 (s, 1H).

Part D. Example 36: The compound of Part C was converted to Example 36 in ~65% yield using the procedures described in Example 1, Part D. $^1$H NMR (400 MHz, DMSO-d6) δ ppm 0.93 (t, J=7.25 Hz, 3H) 1.29 (t, J=7.25 Hz, 3H) 2.34 (s, 3H) 3.00 (m, 2H) 3.71 (d, J=6.15 Hz, 2H) 3.80 (m, 2H) 4.12 (q, J=7.32 Hz, 2H) 7.01 (d, J=7.47 Hz, 1H) 7.09 (d, J=7.91 Hz, 1H) 7.14 (s, 1H) 7.28 (m, 3H) 7.55 (d, J=1.76 Hz, 1H) 7.64 (dd, J=8.13, 1.98 Hz, 1H) 7.71 (s, 1H) 7.81 (t, J=5.27 Hz, 1H) 7.93 (s, 1H) 8.55 (t, J=6.15 Hz, 1H) 8.69 (s, 2H) 9.05 (s, 2H) 12.63 (s, 1H). LC/MS m/z 540.3 (M+H)$^+$. HRMS calcd. for C$_{31}$H$_{34}$N$_5$O$_4$: 540.2611. Found: 540.2602.

Example 37

2'-(6-Carbamimidoyl-1-ethyl-1H-indol-3-ylmethyl)-4-methyl-5'-[(pyridin-3-ylmethyl)-carbamoyl]-biphenyl-2-carboxylic acid Part A. 2-iodo-5-methyl-benzoic acid benzyl ester: A solution of 2-iodo-5-methylbenzoic acid (2 g, 7.6 mmol) in 20 ml DMF was treated with KHCO$_3$ (0.92 g, 9.2 mmol) and then benzyl bromide (1.1 mL, 9.2 mmol). The resulting mixture was stirred overnight at rt under $N_2$. Reaction was poured into water and extracted 3× with EtOAc. Combined extracts were washed with sat'd. NaHCO$_3$ and brine, dried over anh.Na$_2$SO$_4$, filtered and evaporated. Flash chromatography gave the pure benzyl ester (2.62 g, 98%) as a colorless liquid.

Part B. 5-methyl-2-(4,4,5,5-tetramethyl-[1,3,2]dioxaborolan-2-yl)-benzoic acid benzyl ester: A mixture of the compound of Part A (2.6 g, 7.38 mmol), bis(pinacolato)boron (2.02 g, 7.97 mmol), KOAc (2.17 g, 22.1 mmol) and palladium acetate (49.7 mg, 0.221 mmol) in DMF 40 ml) was degassed and then heated with stirring for 2 h in an 85° C. oil bath under $N_2$. Reaction was cooled to rt then poured into 10 volumes of water and extracted 3× with EtOAc. Combined extracts were filtered through a pad of Celite then washed with water (3×) and brine, dried and evaporated. Flash chromatography (hexane/EtOAc 9:1) provided the boronate (1.5 g, 58%) as a white crystalline solid.

Part C. 6'-(6-cyano-1-ethyl-1H-indol-3-ylmethyl)-4-methyl-biphenyl-2,3'-dicarboxylic acid 2-benzyl ester 3'-tert-butyl ester: A mixture of the compound of Part B (0.86 g, 2.46 mmol) and the compound of Example 15, Part C (0.9 g, 2.05 mmol) in a mixture of 20 ml toluene and 8.5 ml ethanol was added 2.05 ml of a 2M Na$_2$CO$_3$ solution (2 eq) and the mixture was degassed by repeated evacuation and flushing with $N_2$ then tetrakis(triphenyl-phosphine)palladium (0.12 g., 0.1 mmol) and tetrabutylammonium bromide (30 mg, 0.1 mol) were added. Degassing was repeated, and the mixture was heated overnight in 95° C. oil bath under $N_2$. Reaction was partitioned between water and EtOAc. Organic layer was washed with brine, dried and evaporated. Flash chromatography (hexane/EtOAc) provided the product (1.2 g, 93%).

Part D. 6'-(6-cyano-1-ethyl-1H-indol-3-ylmethyl)-4-methyl-biphenyl-2,3'-dicarboxylic acid 2-benzyl ester: The compound of Part C (1.00 eq, 1.90 mmol, 1.11 g) was dissolved in 5 ml CH$_2$Cl$_2$ and 5 ml TFA added. The mixture was stirred at rt under $N_2$ for 2 h. The reaction was evaporated in vacuo, ether was added and solution was re-evaporated to give a light tan solid which was re-suspended in ether, decanted several times and dried in vacuo to provide the acid (0.94 g; 96%) as an off-white solid.

Part E. 2'-(6-cyano-1-ethyl-1H-indol-3-ylmethyl)-4-methyl-5'-[(pyridin-3-ylmethyl)-carbamoyl]-biphenyl-2-carboxylic acid benzyl ester: The compound of Part D was coupled with 3-aminomethylpyrdine using the procedure described for Example 15, Part G to provide the amide in 88% yield. $^1$H NMR (500 MHz, CDCl$_3$) δ ppm 1.38 (t, J=7.42 Hz, 3H) 2.41 (s, 3H) 3.79 (s, 2H) 4.04 (q, J=7.15 Hz, 2H) 4.60 (m, 2H) 4.94 (m, 2H) 6.29 (t, J=5.50 Hz, 1H) 6.67 (s, 1H) 6.97 (d, J=7.70 Hz, 1H) 7.03 (m, 2H) 7.16 (d, J=8.25 Hz, 1H) 7.24 (m, 7H) 7.44 (s, 1H) 7.56 (s, 1H) 7.67 (t, J=8.52 Hz, 2H) 7.82 (s, 1H) 8.53 (s, 1H) 8.57 (s, 1H). LC/MS m/z 619.4 (M+H)$^+$.

Part F. Example 37: The compound of Part E was converted to the title compound in ~40% yield using the procedures described in Example 1, Part D. $^1$HNMR (500 MHz, DMSO-D6) δ ppm 1.34 (t, J=7.15 Hz, 3H) 2.39 (s, 3H) 3.85 (d, J=8.80 Hz, 2H) 4.17 (q, J=7.15 Hz, 2H) 4.49 (d, J=6.60 Hz, 2H) 7.08 (d, J=7.70 Hz, 1H) 7.16 (d, J=7.70 Hz, 2H) 7.19 (s, 1H) 7.34 (m, 3H) 7.56 (m, 1H) 7.76 (s, 1H) 7.94 (d, J=8.25 Hz, 1H) 7.98 (s, 1H) 8.56 (d, J=4.95 Hz, 1H) 8.62 (s, 1H) 8.74 (s, 2H) 9.08 (t, J=6.05 Hz, 1H) 9.11 (s, 2H) 12.72 (s, 1H). LC/MS m/z 546.45 (M+H)$^+$. HRMS Calcd for $C_{33}H_{32}N_5O_3$: 546.2505. Found: 546.2515.

Example 40

2'-(6-Carbamimidoyl-1-ethyl-1H-indol-3-ylmethyl)-4-methyl-5'-[(5-methylpyrazin-2-ylmethyl)-carbamoyl]-biphenyl-2-carboxylic acid Part A. 2'-(6-cyano-1-ethyl-1H-indol-3-ylmethyl)-4-methyl-5'-[(5-methylpyrazin-2-ylmethyl)-carbamoyl]-biphenyl-2-carboxylic acid benzyl ester: The compound of Example 37, Part D was coupled with 2-aminomethyl-5-methylpyrazine using the procedure described for Example 15, Part G to provide the amide in 84% yield. $^1$H NMR (500 MHz, CDCl$_3$) δ ppm 1.37 (t, J=7.42 Hz, 4H) 2.41 (s, 3H) 2.55 (s, 3H) 3.78 (s, 2H) 4.03 (q, J=7.51 Hz, 2H) 4.71 (dd, J=11.00, 4.95 Hz, 2H) 4.95 (m, 2H) 6.66 (s, 1H) 7.01 (m, 4H) 7.17 (dd, J=14.30, 8.25 Hz, 2H) 7.24 (m, 4H) 7.51 (s, 1H) 7.55 (s, 1H) 7.67 (d, J=8.25 Hz, 1H) 7.83 (s, 1H) 8.36 (s, 1H) 8.52 (s, 1H).

Part B. Example 40: The compound of Part A was converted to Example 40 in 40% yield using the procedures described in Example 1, Part D. $^1$H NMR (400 MHz, DMSO-D6) δ ppm 1.34 (t, J=7.25 Hz, 3H) 2.39 (s, 3H) 2.44 (s, 3H) 3.84 (m, 2H) 4.17 (q, J=7.47 Hz, 2H) 4.51 (d, J=5.71 Hz, 2H) 7.09 (d, J=7.91 Hz, 1H) 7.15 (d, J=8.35 Hz, 1H) 7.20 (s, 1H) 7.34 (m, 3H) 7.63 (s, 1H) 7.71 (d, J=8.35 Hz, 1H) 7.76 (s, 1H) 7.98 (s, 1H) 8.44 (s, 2H) 8.69 (s, 2H) 9.05 (t, J=5.71 Hz, 1H) 9.10 (s, 2H) 12.67 (s, 1H). LC/MS m/z 561.3 (M+H)$^+$. HRMS calcd. for $C_{33}H_{33}N_6O_3$: 561.2614. Found: 561.2609.

Example 43

2'-(6-Carbamimidoyl-ethyl-1H-indol-3-ylmethyl)-5'-(methylcarbamoylmethyl-carbamoyl)-4-methyl-biphenyl-2-carboxylic acid Part A. 2'-(6-cyano-1-ethyl-1H-indol-3-ylmethyl)-4-methyl-5'-(methylcarbamoylmethyl-carbamoyl)-biphenyl-2-carboxylic acid: A solution of the compound of Example 37, Part D (0.1 g, 0.19 mmol), N-methylglycinamide (0.04 mg, 0.28 mmole), NMM (0.1 ml, 0.9 mmol) and BOP reagent (0.13 g, 0.28 mmol) in 1.5 ml DMF was stirred for 3 days at rt in a screw cap test tube. Reaction was diluted with water and extracted 3× with EtOAc. Combined extracts were washed with water and brine then dried over anh. Na$_2$SO$_4$, filtered and evaporated. Chromatography on silica gel provided the amide product (99 mg. 85%). $^1$H NMR (500 MHz, CDCl$_3$) δ ppm 1.37 (t, J=7.15 Hz, 3H) 2.41 (s, 3H) 2.83 (d, J=4.40 Hz, 3H) 3.77 (s, 2H) 4.03 (m, 4H) 6.06 (s, 1H) 6.66 (s, 1H) 6.75 (t, J=5.22 Hz, 1H) 6.97 (d, J=7.70 Hz, 1H) 7.05 (m, 2H) 7.17 (dd, J=15.95, 8.25 Hz, 2H) 7.24 (m, 5H) 7.50 (s, 1H) 7.56 (s, 1H) 7.64 (d, J=6.05 Hz, 1H) 7.83 (s, 1H). LC/MS m/z 599.4)M+H)$^+$.

Part B. Example 43: Using the procedure described for Example 1, Part D, the compound of Part A above was converted into Example 43 (50 mg; 65%) $^1$H NMR (500 MHz, DMSO-D6) δ ppm 1.35 (t, J=7.15 Hz, 3H) 2.39 (s, 3H) 2.56 (d, J=4.40 Hz, 3H) 3.76 (d, J=7.15 Hz, 2H) 3.85 (m, 2H) 4.17 (q, J=7.51 Hz, 2H) 7.07 (d, J=7.70 Hz, 1H) 7.14 (d, J=8.25 Hz, 1H) 7.20 (s, 1H) 7.34 (m, 3H) 7.61 (d, J=2.20 Hz, 1H) 7.70 (m, 1H) 7.77 (s, 1H) 7.81 (m, J=4.40, 4.40, 4.40 Hz, 1H) 7.98 (s, 1H) 8.66 (t, J=6.05 Hz, 1H) 8.79 (s, 2H) 9.11 (s, 2H) 12.71 (s, 1H). LC/MS m/z 526.4 (M+H)$^+$. HRMS calcd for $C_{29}H_{30}N_5O_4$: 512.2298. Found: 512.2282.

Example 46

2'-(6-Carbamimidoyl-1-ethyl-1H-indol-3-ylmethyl)-4-chloro-5'-[(5-methyl-pyrazin-2-ylmethyl)-carbamoyl]-biphenyl-2-carboxylic acid Part A. 5-chloro-2-(4,4,5,5-tetramethyl-[1,3,2]dioxaborolan-2-yl)-benzoic acid methyl ester: A mixture of methyl 2-bromo-5-chlorobenzoate (1.9 g, 7.65 mmol), bis(pinacolato)diboron (2.1 g, 8.41 mmol), potassium acetate (2.3 g, 22.94 mmol) and PdCl$_2$(dppf) (0.25 g, 0.306 mmol) in 1,4-dioxane (40 mL) was degassed then heated in an 80° C. oil bath overnight under N$_2$. The reaction mixture was filtered through a pad of Celite then diluted with EtOAc and washed with water and brine, dried and concentrated. Flash chromatography on silica gel provided the boronate (0.96 g, 42%). $^1$HNMR (400 MHz, CDCl$_3$) δ 7.92 (m, 1H); 7.48 (m, 2H); 3.91 (s, 3H); 1.41 (s, 12H). LC/MS m/z 297.2 (M+H)$^+$; 319.1 (M+Na)$^+$.

Part B. 4-chloro-6'-(6-cyano-1-ethyl-1H-indol-3-ylmethyl)-biphenyl-2,3'-dicarboxylic acid 3'-tert-butyl ester 2-methyl ester: A solution of 3-Bromo-4-(6-cyano-1-methyl-1H-indol-3-ylmethyl), benzoic acid tert-butyl ester (prepared as described in Example 10, Part B) (0.2 g, 0.468 mmol) and the compound of Part A (0.18 g, 0.608 mmol) in a mixture of toluene (10 mL) and EtOH (4 mL) was treated with a 2M solution of Na$_2$CO$_3$ (0.6 mL). The mixture was degassed followed by addition of (tetrakis)triphenylphosphine palladium (22 mg, 0.019 mmol) and tetrabutylammonium bromide (0.75 mg, 0.0023 mmol). The resulting mixture was stirred and heated in a 95° C. oil bath overnight. The reaction was cooled to rt, filtered and filtrate diluted with EtOAc, then washed with water and brine, dried over anh. Na$_2$SO$_4$, filtered and concentrated. Flash chromatography on silica gel provided the product (0.22 g, 88%). $^1$HNMR (500 MHz, CDCl$_3$) δ 7.97 (m, 1H); 7.92 (m, 1H); 7.68 (m, 1H); 7.59 (s, 1H); 7.38 (m, 1H); 7.30 (m, 2H); 7.20 (m, 1H); 7.01 (m, 1H); 6.73 (s, 1H); 4.08 (m, 2H); 3.88 (m, 2H); 3.58 (s, 3H); 157 (s, 9H); 1.41 (t, 3H, J=7.1 Hz). LC/MS m/z 473.3 (M+H-tBu)$^+$.

Part C. 4-chloro-6'-(6-cyano-1-ethyl-1H-indol-3-ylmethyl)-biphenyl-2,3'-dicarboxylic acid 2-methyl ester: The compound of Part B (0.22 g, 0.42 mmol) was dissolved in methylene chloride (2 mL) and TFA (2 mL) was added. The resulting solution was stirred for 1 h at rt. Solvent was removed and residue triturated with ether then dried in vacuo to provide the crude acid as a yellow solid (0.22 g, quant.) which was used without purification in the next step.

Part D. 4-chloro-2'-(6-cyano-1-ethyl-1H-indol-3-ylmethyl)-5'-[(5-methyl-pyrazin-2-ylmethyl)-carbamoyl]-biphenyl-2-carboxylic acid methyl ester: A mixture of the acid from Part C, 2-aminomethyl-5-methylpyrazine (77 mg, 0.63 mmol), NMM (0.37 mL, 3.34 mmol) and BOP reagent (230 mg, 0.52 mmol) in DMF (1.5 mL) was stirred at rt overnight. Reaction mixture was diluted with EtOAc and washed with water and brine, then dried over anh Na$_2$SO$_4$, filtered and concentrated. Flash chromatography on silica gel provided the product (0.24 g, 89%). LC/MS m/z 578.2 (M+H)$^+$.

Part E. 2'-(6-carbamimidoyl-1-ethyl-1H-indol-3-ylmethyl)-4-chloro-5'-[(5-methyl-pyrazin-2-ylmethyl)-carbamoyl]-biphenyl-2-carboxylic acid methyl ester: HCl (g) was bubbled through a solution of the compound of Part D (0.165 g, 0.29 mmol) in 1:1 MeOH/DCDl$_3$ (20 mL) for 30 min at 0° C. The flask was then sealed and kept in the refrigerator overnight. Solvent was removed and the residue dried in vacuo. The resulting material was redissolved in MeOH (20 mL) and ammonium carbonate (1.4 g, 50 eq) was added. The flask was again sealed and contents stirred at rt overnight. Methanol was removed on rotary evaporator and the residue purified by C18 HPLC to provide the amidine as its trifluoroacetic acid salt (0.1 g, 43%). $^1$HNMR (500 MHz, DMSO-d6) δ 9.10 (m, 3H); 8.73 (s, 2H); 8.44 (m, 2H); 7.98 (m, 1H); 7.91 (s, 1H); 7.80 (m, 1H); 7.66 (m, 1H); 7.60 (m, 1H); 7.32 (m, 3H); 7.25 (m, 1H); 7.11 (s, 1H); 4.52 (m, 2H); 4.16 (m, 2H); 3.86 (m, 2H); 3.49 (s, 3H); 2.44 (s, 3H); 1.33 (m, 3H). LC/MS m/z 595.2 (M+H)$^+$.

Part F. Example 46: The compound of Part E (0.1 g, 0.122 mmol) was dissolved in EtOH (2 mL) and 1N NaOH (1 mL) was added. The resulting mixture was stirred at rt overnight. Reaction mixture was evaporated to dryness and the residue was purified by C18 HPLC to provide Example 46 (89.3 mg, 92%). $^1$HNMR (500 MHz, DMSO-d6) δ 9.11 (s, 2H); 9.08 (m, 1H); 8.72 (s, 2H); 8.44 (s, 2H); 7.98 (m, 1H); 7.91 (s, 1H); 7.75 (m, 1H); 7.63 (m, 1H); 7.58 (m, 1H); 7.33 (m, 2H); 7.21 (m, 1H); 7.17 (m, 2H); 4.52 (m, 2H); 4.17 (m, 2H); 3.87 (m, 2H); 2.45 (s, 3H); 1.34 (t, J=7.2 Hz, 3H). LC/MS m/z 581.2 (M+H)$^+$. HRMS calcd for C$_{32}$H$_{29}$ClN$_6$O$_3$: 581.2068. Found: 581.2058.

Example 47

4-[2-(6-Carbamimidoyl-1-ethyl-1H-indol-3-ylmethyl)-phenyl]-2-methyl-2H-pyrazole-3-carboxylic acid Part A. 4-bromo-2-methyl-2H-pyrazole-3-carboxylic acid methyl ester: To the suspension of 4-Bromo-2-methyl-2H-pyrazole-3-carboxylic acid (0.205 g, 1 mmol) in methanol (2 mL) was added thionyl chloride (0.29 mL, 4 mmol). The suspension was heated at 90° C. for 1 h to give a clear solution. The solution was cooled to rt and then concentrated. The residue was dissolved in EtOAc (10 mL), and washed with sat. NaHCO$_3$, brine, dried over Na$_2$SO$_4$, filtered and concentrated to give 0.137 g (63%) of the methyl ester as a white solid. $^1$H NMR (400 MHz, CDCl$_3$) δ: 3.95 (s, 3H), 4.17 (s, 3H), 7.53 (s, 1H). HRMS calc'd for C$_6$H$_8$BrN$_2$O$_2$: 218.9769. Found: 218.9770.

Part B. 4-[2-(6-cyano-1-ethyl-1H-indol-3-ylmethyl)-phenyl]-2-methyl-2H-pyrazole-3-carboxylic acid methyl ester: The compound of Part A was coupled with the compound from Example 19, Part A using the procedure of Example 19, Part B. Column chromatography on silica gel gave 0.022 g (37%) of the desired product as a white solid. $^1$H NMR (400 MHz, CDCl$_3$) δ 1.42 (t, J=7.2 Hz, 3H), 3.48 (s, 3H), 3.93 (s, 2H), 4.10 (q, J=7.2 Hz, 2H), 4.15 (s, 3H), 6.76 (s, 1H), 7.14 (d, J=7.5 Hz, 1H), 7.19-7.33 (m, 6H), 7.60 (s, 1H). HRMS calc'd for C$_{24}$H$_{23}$N$_4$O$_2$: 399.1821. Found: 399.1823.

Part C. Example 47: To a suspension of the compound from Part B (0.022 g, 0.058 mmol) in MeOH (1 mL) was added 1.0 N NaOH (0.23 mL, 0.23 mmol). The mixture was stirred at rt for 3 h, then 80° C. for 1 h to give a clear solution. The solution was cooled to rt, neutralized with 1.0 N HCl (0.23 mL, 0.23 mmol) and then concentrated to dryness. The residue was dissolved in EtOAc (5 mL) and then washed with brine, dried over Na$_2$SO$_4$, filtered and concentrated. The residue was dissolved in EtOH (1 mL) followed by the addition of hydroxylamine hydrochloride (0.02 g, 0.29 mmol) and triethylamine (0.04 mL, 0.29 mmol). The reaction was then stirred at 80° C. for 18 h. The reaction mixture was cooled to rt, concentrated, and the residue was dissolved in AcOH (1 mL). To this solution was added acetic anhydride (0.016 mL, 0.17 mmol) and the reaction was stirred at rt for 2 h. Additional acetic acid (2 mL) and acetic anhydride (0.032 mL) were added and the reaction was stirred at rt for 1 h and then at 50° C. for 20 min. Upon cooling to rt, zinc dust (0.038 g, 0.58 mmol) was added and the resulting suspension was stirred at rt for 18 h. The excess zinc was removed by filtration and the filtrate was concentrated. Purification by C18 Prep. HPLC gave 0.010 g (33%) of the TFA salt of Example 47 as a red solid. $^1$H NMR (400 MHz, DMSO-d$_6$) δ: 1.36 (t, J=7.2 Hz, 3H), 3.92 (s, 2H), 4.10 (s, 3H), 4.19 (q, J=7.2 Hz, 2H), 7.12-7.40 (m, 9H), 8.00 (s, 1H), 8.76 (s, 2H), 9.13 (s, 2H). HRMS calc'd for C$_{23}$H$_{24}$N$_5$O$_2$: 402.1930. Found: 402.1934.

Example 49

1-[2-(6-Carbamimidoyl-1-ethyl-1H-indol-3-ylmethyl)-phenyl]-pyrrolidine-2-carboxylic acid Part A. 1-[2-(6-cyano-1-ethyl-1H-indol-3-ylmethyl)-phenyl]-pyrrolidine-2-carboxylic acid: A mixture of the compound of Example 1, Part A (0.153 g, 0.45 mmol), K$_2$CO$_3$ (0.124 g, 0.9 mmol), DL-proline (0.259 g, 2.25 mmol), and CuI (0.0086 g, 0.045 mmol) was flushed with argon and DMA (3 mL) was added. The resulting mixture was subjected to microwave irradiation for 15 h at 210° C. in a sealed tube. The reaction mixture was cooled to rt and then diluted with EtOAc (20 mL), water (5 mL), and 1.0 N HCl (2.5 mL). The layers were separated and the organic layer was washed with brine, dried over Na$_2$SO$_4$, filtered and concentrated. Column chromatography on silica gel gave 0.045 g (27%) of product as an off-white solid. $^1$H NMR (500 MHz, CDCl$_3$) δ: 1.43 (t, J=7.1 Hz, 3H), 1.85-2.05 (m, 2H), 2.12-2.20 (m, 1H), 2.38-2.45 (m, 1H), 2.92-2.95 (m, 1H), 3.52-3.57 (m, 1H), 4.11-4.15 (m, 3H), 4.28-4.32 (m, 2H), 6.95 (s, 1H), 7.09-7.13 (m, 2H), 7.22-7.29 (m, 3H), 7.49 (d, J=8.2 Hz, 1H), 7.66 (s, 1H). HRMS calc'd for C$_{23}$H$_{24}$N$_3$O$_2$: 374.1869. Found: 374.1854.

Part B. Example 49: The compound from Part A (0.045 g, 0.1 mmol) was dissolved in EtOH (3 mL), and cooled to 0° C. Into this solution was bubbled HCl gas for 10 min, the flask was sealed with a rubber septum, and the mixture stirred at rt for 16 h. The reaction mixture was concentrated to dryness and the residue was dissolved in EtOH (3 mL). To this solution was added NH$_4$OAc (0.14 g, 1.8 mmol), and the resulting solution was stirred at rt for 24 h. The reaction mixture was concentrated and the residue was purified by prep. C18 HPLC to yield 0.013 g of a dark oil. To a portion (0.0065 g) of this oil in MeOH (0.5 mL) was added 1.0 N NaOH (0.02 mL, 0.02 mmol). After 48 h at rt, the reaction was neutralized with 1.0 N HCl (0.02 mL). Purification by C18 prep. HPLC provided 0.003 g (60%) of the TFA salt of Example 49 as an off-white solid. $^1$H NMR (500 MHz, CD$_3$OD) δ: 1.46 (t, J=7.1 Hz, 3H), 1.98-2.14 (m, 3H), 2.39-2.46 (m, 1H), 3.02-3.07 (m, 1H), 3.59-3.64 (m, 1H), 4.19-4.40 (m, 5H), 6.95 (t, J=6.6 Hz, 1H), 7.06 (d, J=7.2 Hz, 1H), 7.17-7.23 (m, 2H), 7.35 (s, 1H), 7.37 (d, J=8.8 Hz, 1H), 7.59 (d, J=8.3 Hz, 1H), 7.95 (s, 1H). LC/MS 391.3 (M+H)$^+$.

Example 50

2'-(6-Carbamimidoyl-1-ethyl-1H-indol-3-ylmethyl)-4-methyl-5'-[(pyrimidin-2-ylmethyl)-carbamoyl]-biphenyl-2-carboxylic acid and

Example 51

2'-(6-Carbamimidoyl-1-ethyl-1H-indol-3-ylmethyl)-4-methyl-5'-[(1,4,5,6-tetrahydro-pyrimidin-2-ylmethyl)-carbamoyl]-biphenyl-2-carboxylic acid Part A. 2'-(6-cyano-1-ethyl-1H-indol-3-ylmethyl)-4-methyl-5'-[(pyrimidin-2-ylmethyl)-carbamoyl]-biphenyl-2-carboxylic acid: The amide was prepared in 55% yield from the acid of Example 37, Part D following the procedure of Example 37, Part E using 2-aminomethylpyrimidine oxalate in place of 3-aminomethylpyridine. $^1$H NMR (500 MHz, CDCl$_3$) δ ppm 1.38 (t, J=7.42 Hz, 3H) 2.41 (s, 3H) 3.79 (s, 2H) 4.03 (q, J=7.15 Hz, 2H) 4.86 (m, 2H) 4.96 (m, 2H) 6.67 (s, 1H) 7.03 (m, 3H) 7.17 (dd, J=15.40, 8.25 Hz, 2H) 7.24 (m, 5H) 7.41 (t, J=12 Hz, 1H) 7.56 (s, 1H) 7.60 (s, 1H) 7.74 (d, J=9.90 Hz, 1H) 7.84 (s, 1H) 8.71 (d, J=0.40 Hz, 2H). LC/MS m/z 620.4 (M+H)$^+$.

Part B. Example 50 and Example 51: The compound of Part A was converted to the amidine using the procedure described for Example 1, Part D. The reduction resulted in the formation of two products which were separated by C18 HPLC to provide the pyrmidine compound (Example 50-31 mg, 52%) along with the tetrahydropyrimidine analog (Example 51-5 mg, 7%). Example 50: $^1$H NMR (500 MHz, DMSO-D6) δ ppm 1.29 (t, J=7.15 Hz, 3H) 1.76 (m, 2H) 2.34 (s, 3H) 3.24 (s, 4H) 3.80 (m, 2H) 4.07 (m, 2H) 4.11 (q, J=7.15 Hz, 2H) 6.99 (d, J=7.70 Hz, 1H) 7.13 (m, 2H) 7.26 (m, 2H) 7.33 (d, J=7.70 Hz, 1H) 7.57 (d, J=2.20 Hz, 1H) 7.67 (d, J=9.90 Hz, 1H) 7.74 (s, 1H) 7.94 (s, 1H) 8.77 (s, 2H) 8.88 (t, J=5.77 Hz, 1H) 9.06 (s, 2H) 9.43 (s, 2H) 12.67 (s, 1H). LC/MS m/z 547.3 (M+H)$^+$. HRMS calcd for C$_{32}$H$_{31}$N$_6$O$_3$: 547.2458. Found: 547.2447. Example 51: $^1$H NMR (400 MHz, DMSO-d6) δ ppm 1.34 (t, J=7.25 Hz, 3H) 2.39 (s, 3H) 2.44 (s, 3H) 3.84 (m, 2H) 4.17 (q, J=7.47 Hz, 2H) 4.51 (d, J=5.71 Hz, 2H) 7.09 (d, J=7.91 Hz, 1H) 7.15 (d, J=8.35 Hz, 1H) 7.20 (s, 1H) 7.34 (m, 3H) 7.63 (s, 1H) 7.71 (d, J=8.35 Hz, 1H) 7.76 (s, 1H) 7.98 (s, 1H) 8.44 (s, 2H) 8.69 (s, 2H) 9.05 (t, J=5.71 Hz, 1H) 9.10 (s, 2H) 12.67 (s, 1H). LC/MS m/z 551.3 (M+H)$^+$. HRMS calcd. for C$_{32}$H$_{35}$N$_6$O$_3$: 551.2771. Found: 551.2754.

Example 52

6'-(6-Carbamimidoyl-1-ethyl-1H-indol-3-ylmethyl)-4-methyl-biphenyl-2,3'-dicarboxylic acid Example 52 was obtained in ~20% yield from the compound of Example 37, Part D using the procedure of Example 1, Part D. $^1$H NMR (500 MHz, DMSO-D6) δ ppm 1.35 (t, J=7.15 Hz, 3H) 2.39 (s, 3H) 3.86 (m, 2H) 4.18 (q, J=7.15 Hz, 2H) 7.10 (d, J=7.70 Hz, 1H) 7.15 (d, J=8.25 Hz, 1H) 7.24 (s, 1H) 7.31 (d, J=9.90 Hz, 1H) 7.36 (d, J=8.25 Hz, 2H) 7.58 (s, 1H) 7.74 (d, J-=7.70 Hz, 2H) 7.98 (s, 1H) 8.82 (s, 2H) 9.10 (s, 2H) 12.79 (bs, 2H). LC/MS m/z 456.2 (M+H)$^+$. HRMS calcd for C$_{27}$H$_{26}$N$_3$O$_4$: 456.1923. Found: 456.1914.

Example 66

2-{2-(6-Carbamimidoyl-1-ethyl-1H-indol-3-ylmethyl)-5-[(pyridin-2-ylmethyl)-carbamoyl]-phenoxy}-5-methyl-benzoic acid Part A. 3-fluoro-4-methyl-benzoic acid tert-butyl ester. A solution of 3-fluoro-4-methylbenzoic acid (1.54 g, 10 mmol) in a mixture of t-BuOH (36 mL) and THF (4 mL) was treated with BOC anhydride (4.36 g, 20 mmol) and DMAP (0.4 g, 3.3 mmol). The reaction mixture was stirred overnight at rt. t-BuOH was removed in vacuo and the residue diluted with EtOAc, washed with water, sat'd. NaHCO$_3$ and brine, then dried over Na$_2$SO$_4$, filtered and evaporated to give the crude t-butyl ester as a light brown oil (1.6 g, 76%).

Part B. 3-fluoro-4-formyl-benzoic acid tert-butyl ester. The ester from Part A (7.5 mmol) was dissolved in CCl4 (40 mL) and N-bromosuccinimide (3.34 g, 18.8 mmol) and benzoyl peroxide (0.36 g, 1.5 mmol) were added. The resulting mixture was stirred at reflux overnight. After cooling to rt, the solvent was removed in vacuo. The residue was diluted with EtOAc and washed with water, sat'd NaHCO$_3$, and brine, then dried over Na$_2$SO$_4$, filtered and concentrated. The crude product mixture was dissolved in hexane and insolubles filtered off. Filtrate was evaporated to give the crude dibromide as a light yellow oil (2.5 g). This material was taken up in morpholine (30 mL) and stirred at 60° C. overnight. Excess morpholine was partially removed under reduced pressure then the residue was diluted with EtOAc, washed repeatedly with 5% citric acid until the aqueous layer remained at pH=4. The organic layer was then washed with brine and dried over Na$_2$SO$_4$, filtered and evaporated. Flash chromatography on silica gel provided the aldehyde as a white solid.

Part C. 6'-formyl-4-methyl-biphenyl-2,3'-dicarboxylic acid 3'-tert-butyl ester 2-methyl ester. A mixture of the compound of Part B (0.157 g, 0.7 mmol), methyl 5-methylsalicylate (0.116 g, 0.7 mmol), N,N-dimethylglycine (14 mg, 0.14 mmol), potassium phosphate (0.327 g, 1.75 mmol), and copper iodide (27 mg, 0.14 mmol) in DMF (4 mL) was stirred at 120° C. overnight. Reaction mixture was cooled to rt, diluted with EtOAc, washed with water and brine then dried over Na$_2$SO$_4$, filtered and concentrated. Purification by flash chromatography provided the diaryl ether as a light yellow oil. (97 mg, 37%).

Part D. Example 66. The aldehyde of part C was converted into the title compound using the procedures described above under Example 12, Part A & B followed by amidine formation using the procedure of Example 1, Part D and saponification of the methyl ester. $^1$H NMR (400 MHz, MeOH-D4) δ ppm 1.38-1.47 (m, 3H) 2.34 (s, 3H) 4.18-4.30 (m, 4H) 4.77 (s, 2H) 6.64 (d, J=8.35 Hz, 1H) 7.21-7.30 (m, 2H) 7.37-7.46 (m, 3H) 7.56 (dd, J=7.91, 1.76 Hz, 1H) 7.70-7.79 (m, 2H) 7.80-7.91 (m, 2H) 7.94 (s, 1H) 8.41 (t, J=7.91 Hz, 1H) 8.68 (d, J=4.83 Hz, 1H). MS m/Z 562.3 (M+H)$^+$.

Example 107

2'-(6-Carbamimidoyl-1-ethyl-1H-indazol-3-ylmethyl)-4-methoxy-5'-[(5-methyl-pyrazin-2-ylmethyl)-carbamoyl]-biphenyl-2-carboxylic acid Part A. 3-bromo-4-bromomethyl-benzoic acid tert-butyl ester: A suspension of tert-butyl 3-bromo-4-methylbenzoate (prepared as described above under Example 10, Part A (14.42 g, 53 mmol), N-bromosuccinimide (10.40 g, 58.5 mmol), and benzoyl peroxide (0.641 g, 2.65 mmol) in carbon tetrachloride (265 mL) was heated to reflux. After 4 h, the reaction was cooled to rt, filtered to remove the succinimide and the filtrate concentrated to give a clear, viscous oil which solidified in the refrigerator to give a yellow solid weighing 20.47 g. Column chromatography on silica gel gave 9.26 g (50%) of the bromide as a white solid. $^1$H NMR (500 MHz, CDCl$_3$) δ: 8.16 (d, J=1.4 Hz, 1H), 7.89 (dd, J=8.2, 1.6 Hz, 1H), 7.49 (d, J=8.2 Hz, 1H), 4.60 (s, 2H), 1.58 (s, 9H).

Part B. 3-bromo-4-[2-(4-cyano-2-fluoro-phenyl)-2-oxo-ethyl]-benzoic acid tert-butyl ester: To a flame-dried flask was added zinc (100 mesh). The flask was purged with argon for several minutes and then degassed THF (2.2 mL) was added. The vigorously stirred suspension was cooled to −5° C. and a 1.0 M solution of the compound from Part A (5.0 g, 14.36 mmol) in degassed THF (14.4 mL) was added dropwise (1 drop every 5-10 seconds) over a 1 h, 45 min period. The temperature was maintained at 0° C. or below during the addition. After the addition was complete the reaction was stirred for an additional 30 min., then stirring was stopped to allow the zinc dust to settle. After 1.5 h, a slightly cloudy, pale yellow supernatant remained. In a separate flame-dried flask was added 4-cyano-2-fluorobenzoyl chloride (2.64 g, 14.40 mmol). The flask was cooled to 0° C., and degassed THF (14.4 mL) was added. To the clear, pale yellow solution was added the benzyl zinc bromide (prepared above) followed by tetrakis(triphenylphosphine)palladium(0) (0.415 g, 0.359 mmol). The resulting clear, orange solution was stirred at 0° C. for 1.5 h, quenched with 1.0 N HCl and extracted with EtOAc (2×). The combined organic layers were washed with sat. NaHCO$_3$, brine, dried over Na$_2$SO$_4$, filtered and concentrated to give an orange solid weighing 5.96 g. Column chromatography on silica gel gave 4.28 g (71%) of the product as a white solid. $^1$H NMR (500 MHz, CDCl$_3$) δ: 8.18 (d, J=1.6 Hz, 1H), 7.97 (t, J=7.4 Hz, 1H), 7.91 (dd, J=7.7, 1.6 Hz, 1H), 7.57 (dd, J=8.8, 1.1 Hz, 1H), 7.51 (dd, J=9.8, 1.1, 1H), 7.30 (d, J=7.7 Hz, 1H), 4.46 (d, J=2.8 Hz, 2H), 1.58 (s, 9H). $^{19}$F NMR (470 MHz, CDCl$_3$) δ -106.5. LCMS m/z 440.11 (M+Na)+ and 442.11 (M+2+Na)+.

Part C. 3-Bromo-4-(6-cyano-1-ethyl-1H-indazol-3-ylmethyl)-benzoic acid tert-butyl ester: A white suspension of the compound from Part B (2.50 g, 5.98 mmol), ethyl hydrazine oxalate (1.80 g, 11.96 mmol), and pyridine (2.90 mL, 35.88 mmol) in ethanol (24 mL) was microwaved at 150° C. for 30 min. The resulting clear, slightly yellow solution was concentrated and partitioned between EtOAc and sat. NaHCO$_3$. The layers were separated and the aqueous layer was extracted with EtOAc (2×). The combined organic layers were washed with brine, dried over Na$_2$SO$_4$, filtered, and concentrated to give a milky yellow residue. Dichloromethane was added to give a suspension which was filtered to give a white solid and a yellow filtrate. The filtrate was concentrated to give a viscous oil weighing 3.6 g. Column chromatography on silica gel gave 1.79 g (68%) of the indazole as a thick, viscous pale yellow oil. $^1$H NMR (500 MHz, CDCl$_3$) δ: 8.18 (d, J=0.8 Hz, 1H), 7.80 (dd, J=8.2, 1.1 Hz, 1H), 7.75 (s, 1H), 7.55 (d, J=8.8 Hz, 1H), 7.24 (dd, J=8.2, 1.1 Hz, 1H), 7.19 (d, J=8.2 Hz, 1H), 4.49 (s, 2H), 4.43 (q, J=7.2 Hz, 2H), 1.56 (s, 9H), 1.51 (t, J=7.2 Hz, 3H). HRMS calc'd. for C$_{22}$H$_{23}$N$_3$O$_2$Br: 440.0974. Found 440.0984.

Part D. 3-Bromo-4-(6-cyano-1-ethyl-1H-indazol-3-ylmethyl)-N-(5-methyl-pyrazin-2-ylmethyl)-benzamide: To a solution of the compound from Part C (0.132 g, 0.3 mmol) in CH$_2$Cl$_2$ (2 mL) was added TFA (2 mL). The reaction was stirred at rt for 1 h and then concentrated. The residue was dissolved in DMF (4 mL) and then triethylamine (0.15 mL, 1.05 mmol), (5-methylpyrazin-2-yl)methanamine (0.037 mL, 0.33 mmol), HOBt (0.061 g, 0.45 mmol), and EDCI (0.086 g, 0.45 mmol) were added. The reaction mixture was stirred at rt for 18 h, and then diluted with EtOAc (50 mL). The mixture was washed with water (15 mL), sat. NaHCO$_3$ (15 mL), brine, dried over Na$_2$SO$_4$, filtered and concentrated. The residue was dissolved in a minimal amount of CH$_2$Cl$_2$ and then hexane was added to give a suspension. The solid was collected by filtration and washed with hexane to give 0.13 g (89%) of product as a white solid. $^1$H NMR (500 MHz, CDCl$_3$) δ: 1.53 (t, J=7.4 Hz, 3H), 2.57 (s, 3H), 4.44 (q, J=7.4 Hz, 2H), 4.51 (s, 2H), 4.74 (d, J=4.9 Hz, 2H), 7.18-7.27 (m, 3H), 7.58 (d, J=8.2 Hz, 1H), 7.66 (dd, J=1.7 Hz, 7.7 Hz, 1H), 7.76 (s, 1H), 8.09 (d, J=1.7 Hz, 1H), 8.39 (s, 1H), 8.54 (s, 1H). HRMS calc'd for C$_{24}$H$_{22}$BrN$_6$O: 489.1038. Found: 489.1024.

Part E. 6-(6-Cyano-1-ethyl-1H-indazol-3-ylmethyl)-2'-formyl-4'-methoxy-biphenyl-3-carboxylic acid (5-methyl-pyrazin-2-ylmethyl)-amide: The compound from Part D and 2-formyl-4-methoxyphenylboronic acid were coupled according to the procedure described in Example 19, Part B. Column chromatography on silica gel gave 0.14 g (95%) of product as a yellow oil. HRMS calc'd for C$_{32}$H$_{29}$N$_6$O$_3$: 545.2301. Found 545.2312.

Part F. Example 107: To the solution of compound from Part D (0.14 g, 0.26 mmol) in t-BuOH/CH$_3$CN/H$_2$O (9 mL/1.5 mL/3 mL) was added 2-methyl-2-butene (0.16 mL, 1.54 mmol), NaH$_2$PO$_4$ (0.046 g, 0.39 mmol), and NaClO$_2$ (0.105 g, 1.16 mmol). The reaction mixture was stirred at rt for 2 h and then diluted with water (20 mL). The mixture was extracted with CH$_2$Cl$_2$ (2×10 mL). The combined organic layers were washed with brine, dried over Na$_2$SO$_4$, filtered and concentrated to give a white solid. This white solid was dissolved in EtOH/CHCl$_3$ (1.2 mL/4.8 mL) and cooled to 0° C. Into this solution was bubbled HCl gas for 10 min, the flask was sealed with rubber septum, and the mixture was stirred at rt for 16 h. The reaction mixture was concentrated to dryness, and the residue was dissolved in EtOH (6 mL). To this solution was added NH$_4$OAc (0.3 g, 3.9 mmol) and the resulting solution was stirred at rt for 24 h. The reaction mixture was concentrated, and the residue was purified by C18 prep. HPLC to yield 0.062 g (30%) of the TFA salt of Example 107 as a white solid. $^1$H NMR (500 MHz, CD$_3$OD) δ: 1.45 (t, J=7.2 Hz, 3H), 2.52 (s, 3H), 3.84 (s, 3H), 4.21 (s, 2H), 4.42 (q, J=7.2 Hz, 2H), 4.64 (s, 2H), 6.93 (d, J=8.8 Hz, 1H), 6.98 (dd, J=2.5 Hz, 8.5 Hz, 1H), 7.28-7.30 (m, 2H), 7.45 (d, J=8.8 Hz, 1H), 7.51 (d, J=2.8 Hz, 1H), 7.63 (d, J=2.2 Hz, 1H), 7.75 (dd, J=1.9 Hz, 7.9 Hz, 1H), 8.02 (s, 1H), 8.45-8.46 (2s, 2H). HRMS calc'd for C$_{32}$H$_{32}$N$_7$O$_4$: 578.2516. Found 578.2531.

Example 108

2'-(6-Carbamimidoyl-1-ethyl-1H-indazol-3-ylmethyl)-4-methyl-5'-[(5-methyl-pyrazin-2-ylmethyl)-carbamoyl]-biphenyl-2-carboxylic acid Part A. 6'-(6-cyano-1-ethyl-1H-indazol-3-ylmethyl)-4-methyl-biphenyl-2,3'-dicarboxylic acid 2-benzyl ester 3'-tert-butyl ester: The compound from Example 107, Part C (0.066 g, 0.15 mmol) and benzyl 5-methyl-2-(4,4,5,5-tetramethyl-1,3,2-dioxaborolan-2-yl)benzoate (0.079 g, 0.225 mmol) were coupled according to the procedure described in Example 19, Part B. Column chromatography on silica gel gave 0.088 g (100%) of product as a greenish thick oil. $^1$H NMR (400 MHz, CDCl$_3$) δ: 1.45 (t, J=7.3 Hz, 3H), 1.55 (s, 9H), 2.41 (s, 3H), 4.03-4.09 (m, 2H), 4.33 (q., J=7.3 Hz, 2H), 4.96 (d, J=12.3 Hz, 1H), 5.05 (d, J=12.3 Hz, 1H), 6.96 (d, J=7.9 Hz, 1H), 7.03-7.28 (m, 9H), 7.65 (s, 1H), 7.70 (d, J=1.8 Hz, 1H), 7.81 (dd, J=2.0 Hz, 8.1 Hz, 1H), 7.86 (d, J=1.3 Hz, 1H). HRMS calc'd for C$_{37}$H$_{36}$N$_3$O$_4$: 586.2706. Found 586.2698.

Part B. 2'-(6-cyano-1-ethyl-1H-indazol-3-ylmethyl)-4-methyl-5'-[(5-methyl-pyrazin-2-ylmethyl)-carbamoyl]-biphenyl-2-carboxylic acid benzyl ester: The compound from Part A (0.088 g, 0.15 mmol) was converted to the amide according to the procedure in Example 107, Part D. Column chromatography on silica gel gave 0.073 g (77%) of the product as a colorless oil. $^1$H NMR (500 MHz, CDCl$_3$) δ: 1.45 (t, J=7.4 Hz, 3H), 2.41 (s, 3H), 2.55 (s, 3H), 4.06-4.11 (m, 2H), 4.44 (q, J=7.4 Hz, 2H), 4.66-4.75 (m, 2H), 4.94 (d, J=12.6 Hz, 1H), 5.02 (d, J=12.6 Hz, 1H), 6.96 (d, J=7.7 Hz, 1H), 7.04-7.27 (m, 10H), 7.55 (d, J=2.2 Hz, 1H), 7.66-7.69 (m, 2H), 7.84 (s, 1H), 8.36 (s, 1H), 8.52 (s, 1H). HRMS m/z calc'd for $C_{39}H_{35}N_6O_3$ [M+H]$^+$: 635.2771. Found 635.2776.

Part C. Example 108: To a suspension of compound from Part B (0.073 g, 0.12 mmol) in MeOH (3 mL) was added 1.0 N NaOH (0.46 mL, 0.46 mmol). The mixture was stirred at 50° C. for 5 h, then 80° C. for 0.5 h to give a clear solution. The solution was cooled to rt, neutralized with 1.0 N HCl (0.5 mL, 0.5 mmol), and concentrated to dryness. Purification by Prep.C18 HPLC gave 0.044 g of the carboxylic acid as a white solid. This solid was dissolved in EtOH/CHCl$_3$ (0.6 mL/2.4 mL) and then cooled to 0° C. Into this solution was bubbled HCl gas for 10 min, the flask was sealed with rubber septum, and the mixture was stirred at rt for 16 h. The reaction mixture was concentrated to dryness and the residue was dissolved in EtOH (3 mL). To this solution was added NH$_4$OAc (0.133 g, 1.73 mmol), and the resulting solution was stirred at rt for 24 h. The reaction mixture was concentrated and the residue was purified by prep. C18 HPLC to yield 0.027 g (28%) of the TFA salt of Example 108 as a white solid. $^1$H NMR (500 MHz, CD$_3$OD) δ: 1.45 (t, J=7.2 Hz, 3H), 2.38 (s, 3H), 2.51 (s, 3H), 4.20 (s, 2H), 4.41-4.43 (m, 2H), 4.65 (s, 2H), 6.93 (dd, J=2.8 Hz, 7.7 Hz, 1H), 7.25-7.31 (m, 3H), 7.44 (d, J=8.8 Hz, 1H), 7.63 (s, 1H), 7.75-7.76 (m, 1H), 7.81 (s, 1H), 8.02 (s, 1H), 8.45 (s, 1H), 8.46 (s, 1H). HRMS calc'd for $C_{32}H_{32}N_7O_3$: 562.2567. Found 562.2571.

Example 201

2'-[1-Ethyl-6-(N-hydroxycarbamimidoyl)-1H-indol-3-ylmethyl]-4-methoxy-5'-[(pyridin-2-ylmethyl)-carbamoyl]-biphenyl-2-carboxylic acid Part A. 2'-[(6-cyano-1-ethyl-1H-indol-3-ylmethyl)]-4-methoxy-5'-[(pyridine-2-ylmethyl)-carbamoyl]-biphenyl-2-carboxylic acid: The compound of Example 12, Part B (0.23 g, 0.48 mmol) was coupled to 2-formyl-4-methoxyphenylboronic acid using the procedure outlined under Example 9, Part A. The resulting aldehyde (50 mg, 0.094 mmol) was then oxidized to the corresponding acid by the procedure of Example 1, Part C.

Part B. Example 201: The crude acid of Part A was dissolved in ethanol (5 mL) and hydroxylamine hydrochloride (35 mg, 5 eq.) and triethylamine (70 μL, ~5 eq) were added. The mixture was stirred in an 80° C. oil bath under reflux and N$_2$ overnight then cooled to rt and evaporated to dryness. Prep C18 HPLC provide Example 201 (16 mg) as a light yellow solid. $^1$H NMR (500 MHz, DMSO-D6) δ ppm 1.34 (m, 3H) 3.85 (m, 5H) 4.17 (q, J=7.15 Hz, 2H) 4.54 (d, J=6.05 Hz, 2H) 7.16 (m, 5H) 7.34 (m, 3H) 7.45 (s, 1H) 7.66 (d, J=2.20 Hz, 1H) 7.73 (m, 1H) 7.82 (t, J=7.15 Hz, 1H) 7.86 (s, 1H) 8.52 (d, J±4.95 Hz, 1H) 8.90 (s, 1H) 9.08 (t, J=5.77 Hz, 1H) 9.23 (s, 1H) 11.01 (s, 1H) 12.53 (s, 1H) 12.83 (s, 1H).

Example 202

2'-[1-Ethyl-6-(N-hydroxycarbamimidoyl)-1H-indol-3-ylmethyl]-4-methyl-5'-[(5-methylpyrazin-2-ylmethyl)-carbamoyl]-biphenyl-2-carboxylic acid Part. A: The compound of Ex. 40, Part A (0.34 g, 0.54 mmol) was dissolved in THF (6 mL) and 1M LiOH solution (2.5 mL) was added along with a small amount of MeOH. The resulting mixture was stirred overnight at rt. Reaction mixture was diluted with water and extracted 2× with EtOAc, and extracts set aside. Aqueous was then adjusted to pH<3 with 1M HCl and reextracted 3× with EtOAc. The latter extracts were combined and washed with brine, then dried over Na$_2$SO$_4$, filtered and evaporated to provide the acid (49 mg, 17%). LC/MS m/z 544.3 (M+H)+. $^1$H NMR (500 MHz, CDCl$_3$) δ ppm 1.34 (t, J=7.42 Hz, 3H) 2.40 (s, 3H) 2.52 (s, 3H) 3.85 (m, 2H) 4.01 (q, J=7.51 Hz, 2H) 4.63 (m, 2H) 6.77 (s, 1H) 6.95 (d, J=8.25 Hz, 1H) 7.03 (m, 1H) 7.08 (d, J=8.25 Hz, 1H) 7.27 (s, 1H) 7.39 (m, 1H) 7.52 (m, 2H) 7.63 (s, 1H) 7.80 (s, 1H) 8.19 (s, 1H) 8.60 (s, 1H).

Part B. Example 202: The compound of Part A (48 mg, 0.088 mmole) was dissolved in ethanol (5 mL) and hydroxylamine hydrochloride (35 mg, 0.50 mmol) and triethylamine (70 μL, 0.5 mmol) were added. The resulting mixture was stirred at reflux in an 80° C. oil bath overnight under N$_2$. Reaction mixture was then cooled to rt and evaporated to dryness. C18 HPLC provided Example 202 as its TFA salt after removal of solvent and lyophilization (30 mg, 50%). LC/MS m/z 577.3 (M+H)$^+$. HRMS calcd for $C_{33}H_{33}N_6O_4$: 577.2563. Found: 577.2570. $^1$H NMR (500 MHz, DMSO-D6) δ ppm 1.33 (q, J=7.51 Hz, 3H) 2.39 (s, 3H) 2.44 (s, 3H) 3.84 (m, 2H) 4.16 (q, J=7.15 Hz, 2H) 4.51 (d, J=6.05 Hz, 2H) 7.12 (dd, J=16.77, 7.97 Hz, 2H) 7.18 (m, 2H) 7.35 (dd, J=15.12, 7.97 Hz, 2H) 7.62 (d, J=2.20 Hz, 1H) 7.71 (m, 1H) 7.76 (s, 1H) 7.85 (s, 1H) 8.44 (s, 2H) 9.07 (t, J=5.77 Hz, 1H) 10.95 (s, 1H) 12.53 (s, 1H) 12.70 (s, 1H).

Example 203

2'-[1-Ethyl-6-(N-hydroxycarbamimidoyl)-1H-indol-3-ylmethyl]-4-methoxy-5'-[(3-triazolylmethyl)-carbamoyl]-biphenyl-2-carboxylic acid Example 203 was prepared from Example 33, Part B following the procedures described under Example 202 above. $^1$H NMR (500 MHz, DMSO-D6) δ ppm 1.34 (t, J=7.15 Hz, 3H) 3.85 (m, 5H) 4.17 (q, J=7.15 Hz, 2H) 4.49 (d, J=5.50 Hz, 2H) 7.12 (m, 4H) 7.18 (m, 2H) 7.35 (d, J=8.80 Hz, 1H) 7.44 (d, J=2.75 Hz, 1H) 7.64 (s, 1H) 7.70 (d, J=7.70 Hz, 1H) 7.86 (s, 1H) 8.95 (m, 2H) 9.24 (s, 1H) 10.99 (s, 1H) 12.52 (s, 1H) 12.81 (s, 1H). LC/MS m/z 568.3 (M+H)$^+$. HRMS calcd for $C_{30}H_{30}N_7O_5$: 568.2308. Found: 568.2316.

Example 204

2'-[1-Ethyl-6-aminomethyl-1H-indol-3-ylmethyl]-4-methoxy-5'-[(pyridin-2-ylmethyl)-carbamoyl]-biphenyl-2-carboxylic acid To a solution of 2'-[1-ethyl-6-cyano-1H-indol-3-ylmethyl]-4-methoxy-5'-[(pyridin-2-ylmethyl)-carbamoyl]-biphenyl-2-carboxylic acid (prepared as described under Example 12, Part C) in ethanol (5 mL) was added TFA (1 eq) and Raney Nickel catalyst. The mixture was kept under 1 atm of H$_2$ with stirring overnight. Catalyst was removed by filtration and filtrate evaporated. Example 204 was isolated by preparative TLC (CH$_2$Cl$_2$/MeOH/NH$_4$OH 80:20:1). $^1$H NMR (500 MHz, METHANOL-D4) δ ppm 1.38 (t, J=7.15 Hz, 3H) 3.88 (m, 5H) 4.15 (m, 4H) 4.79 (m, 2H) 6.82 (s, 1H) 6.96 (d, J=8.25 Hz, 1H) 7.06 (m, 1H) 7.27 (m, J=7.97, 4.12 Hz, 2H) 7.42 (s, 1H) 7.55 (d, J=2.75 Hz, 1H) 7.65 (s, 1H) 7.73 (m, 2H) 7.81 (d, J=8.25 Hz, 1H) 8.30 (t, J=7.70 Hz, 1H) 8.65 (d, J=5.50 Hz, 1H). LC/MS m/z 532.4 (M+H)$^+$.

Other examples were also prepared by following the procedures described above. Tables 1-2 below summarize examples of the prepared compounds in the present invention.

TABLE 1

(Id)

| Ex | R⁴ | A | B | MS (M + 1) |
|---|---|---|---|---|
| 1 | H | 1,2-phenylene | 2-CO₂H-4-OMe-phenyl | 400.2 |
| 2 | Bn | 1,2-phenylene | 2-CO₂H-4-OMe-phenyl | 490.2 |
| 3 | Et | 1,2-phenylene | 2-CO₂H-4-OMe-phenyl | 428.2 |
| 4 | i-Bu | 1,2-phenylene | 2-CO₂H-4-OMe-phenyl | 456.2 |
| 5 | —CH₂-cyclopropyl | 1,2-phenylene | 2-CO₂H-4-OMe-phenyl | 454.2 |
| 6 | —CH₂-(3-pyridyl) | 1,2-phenylene | 2-CO₂H-4-OMe-phenyl | 491.1 |
| 7 | Bn | 1,3-phenylene | 2-CO₂H-4-CONH₂-phenyl | 503.2 |
| 8 | Et | 1,3-phenylene | 2-CO₂H-4-CONH₂-phenyl | 441.2 |
| 9 | Et | 1,3-phenylene | 2-CO₂H-4-OMe-phenyl | 428.2 |
| 10 | Et | 5-CONHMe-1,2-phenylene | 2-CO₂H-4-OMe-phenyl | 471.2 |
| 11 | Et | 5-CONHMe-1,2-phenylene | 2-CO₂H-4-OMe-phenyl | 485.2 |
| 12 | Et | 5-CONH(—CH₂-2-pyridyl)-1,2-phenylene | 2-CO₂H-4-OMe-phenyl | 562.3 |
| 13 | Me | 1,2-phenylene | 2-CO₂H-4-OMe-phenyl | 414.3 |
| 14 | Pr | 1,2-phenylene | 2-CO₂H-4-OMe-phenyl | 442.3 |
| 15 | Et | 5-CONH(—CH₂-3-pyridyl)-1,2-phenylene | 2-CO₂H-4-OMe-phenyl | 562.4 |
| 16 | Et | 5-CONH(—CH₂-4-pyridyl)-1,2-phenylene | 2-CO₂H-4-OMe-phenyl | 562.3 |
| 17 | Et | 5-CONHMe-1,2-phenylene | 2-CO₂H-4-Me-phenyl | 469.4 |
| 18 | Et | 5-CONH(—CH₂-2-pyridyl)-1,2-phenylene | 2-CO₂H-4-Me-phenyl | 546.3 |
| 19 | Et | 1,2-phenylene | 2-CO₂H-phenyl | 398.2 |
| 20 | Et | 5-CONHEt-1,2-phenylene | 2-CO₂H-4-OMe-phenyl | 499.3 |
| 21 | Et | 5-CONHPr-1,2-phenylene | 2-CO₂H-4-OMe-phenyl | 513.4 |
| 22 | —(CH₂)₂CONH₂ | 1,2-phenylene | 2-CO₂H-4-OMe-phenyl | 471.4 |
| 23 | —(CH₂)₃CONH₂ | 1,2-phenylene | 2-CO₂H-4-OMe-phenyl | 485.4 |
| 24 | —CONH₂ | 1,2-phenylene | 2-CO₂H-4-OMe-phenyl | 443.2 |
| 25 | Et | 5-CONH(—CH₂-2-pyridyl)-1,2-phenylene | 2-CH₂OH-4-OMe-phenyl | 548.4 |
| 26 | Et | 1,2-phenylene | 2-CO₂H-4-Cl-phenyl | 432.1 |
| 27 | Et | 5-CONHBn-1,2-phenylene | 2-CO₂H-4-OMe-phenyl | 561.3 |
| 28 | Et | 5-CONHCH₂CONHEt-1,2-phenylene | 2-CO₂H-4-OMe-phenyl | 556.4 |
| 29 | Et | 5-CONH(—CH₂-2-oxazolyl)-1,2-phenylene | 2-CO₂H-4-OMe-phenyl | 552.3 |
| 30 | Et | 5-CONH(—CH₂-(5-Me-2-pyrazinyl))-1,2-phenylene | 2-CO₂H-4-OMe-phenyl | 577.3 |
| 31 | Et | 5-CONH(—CH₂-(2-pyrimidinyl))-1,2-phenylene | 2-CO₂H-4-OMe-phenyl | 563.2 |

TABLE 1-continued (Id)

| Ex | R⁴ | A | B | MS (M + 1) |
|---|---|---|---|---|
| 32 | Et | 5-CONH(—CH₂-(3,4,5,6-tetrahydro-2-pyrimidinyl))-1,2-phenylene | 2-CO₂H-4-OMe-phenyl | 567.2 |
| 33 | Et | 5-CONH(—CH₂-(1,2,4-triazolyl))-1,2-phenylene | 2-CO₂H-4-OMe-phenyl | 536.2 |
| 34 | Et | 5-CONH(—CH₂-(1,2,4-triazolyl))-1,2-phenylene | 2-CO₂H-4-Me-phenyl | 568.3 |
| 35 | Et | 1,2-phenylene | 2-CO₂Et-phenyl | 426.2 |
| 36 | Et | 5-CONHCH₂CONHEt-1,2-phenylene | 2-CO₂H-4-Me-phenyl | 540.0 |
| 37 | Et | 5-CONH(—CH₂-3-pyridyl)-1,2-phenylene | 2-CO₂H-4-Me-phenyl | 546.4 |
| 38 | Et | 5-CONHBn-1,2-phenylene | 2-CO₂H-4-Me-phenyl | 545.5 |
| 39 | Et | 5-CONH(—CH₂-4-pyridyl)-1,2-phenylene | 2-CO₂H-4-Me-phenyl | 546.5 |
| 40 | Et | 5-CONH(—CH₂-(5-Me-2-pyrazinyl))-1,2-phenylene | 2-CO₂H-4-Me-phenyl | 561.5 |
| 41 | Et | 5-CONHPr-1,2-phenylene | 2-CO₂H-4-Me-phenyl | 497.4 |
| 42 | Et | 5-CONH(—CH₂-cyclopropyl)-1,2-phenylene | 2-CO₂H-4-Me-phenyl | 509.4 |
| 43 | Et | 5-CONHCH₂CONHMe-1,2-phenylene | 2-CO₂H-4-OMe-phenyl | 526.4 |
| 44 | Et | 5-CONHCH₂CONH₂-1,2-phenylene | 2-CO₂H-4-OMe-phenyl | 512.4 |
| 45 | Et | 5-CONH-(CH₂-cyclohexyl)-1,2-phenylene | 2-CO₂H-4-Me-phenyl | 551.5 |
| 46 | Et | 5-CONH(—CH₂-(5-Me-2-pyrazinyl))-1,2-phenylene | 2-CO₂H-4-Cl-phenyl | 581.2 |
| 47 | Et | 1,2-phenylene | 1-Me-5-CO₂H-4-pyrazolyl | 402.2 |
| 48 | Et | 1,2-phenylene | 1-Me-3-CO₂H-4-pyrazolyl | 402.2 |
| 49 | Et | 1,2-phenylene | 2-CO₂H-1-pyrrolidinyl | 391.3 |
| 50 | Et | 5-CONH(—CH₂-2-pyrimidinyl)-1,2-phenylene | 2-CO₂H-4-Me-phenyl | 547.3 |
| 51 | Et | 5-CONH(—CH₂-2-[3,4,5,6-tetrahydropyrimidinyl)-1,2-phenylene | 2-CO₂H-4-Me-phenyl | 551.3 |
| 52 | Et | 5-carboxy-1,2-phenylene | 2-CO₂H-4-Me-phenyl | 456.2 |
| 53 | Et | 5-CONH(—CH₂-2-thiazolyl)-1,2-phenylene | 2-CO₂H-4-OMe-phenyl | 568.4 |
| 54 | Et | 5-CONH(—CH₂-4-thiazolyl)-1,2-phenylene | 2-CO₂H-4-OMe-phenyl | 568.2 |
| 55 | Et | 5-CONH(—CH₂-5-thiazolyl)-1,2-phenylene | 2-CO₂H-4-OMe-phenyl | 568.1 |
| 56 | Et | 5-CONH(—CH₂-4-imidazolyl)-1,2-phenylene | 2-CO₂H-4-OMe-phenyl | 551.4 |
| 57 | Et | 5-CONH(—CH₂-2-imidazolyl)-1,2-phenylene | 2-CO₂H-4-OMe-phenyl | 551.3 |
| 58 | SO₂Me | 1,2-phenylene | 2-CO₂H-4-OMe-phenyl | 478.4 |
| 59 | Et | 1,2-phenylene | 3-CO₂H-5-Cl-2-pyridyl | 433.1 |

TABLE 1-continued (Id) Structure: indole core with 6-carboxamidine (H₂N-C(=NH)-), N1-R⁴, and 3-CH₂-A-B substituent.

| Ex | R⁴ | A | B | MS (M + 1) |
|---|---|---|---|---|
| 60 | Et | 1,2-phenylene | 2-CO₂H-4,5-(methylenedioxy)phenyl | 442.2 |
| 61 | Et | 1,2-phenylene | 3-CO₂H-6-Me-2-pyridyl | 413.2 |
| 62 | Et | 1,2-phenylene | 2-CO₂H-3-Me-phenyl | 412.2 |
| 63 | Et | 5-CONH[—CH₂-(4-CH₃COphenyl)]-1,2-phenylene | 2-CO₂H-4-OMe-phenyl | 603.5 |
| 64 | Et | 5-CONH(—CH₂-(1,2,4-triazolyl))-1,2-phenylene | 2-CO₂H-4-Me-phenyl | 536.2 |
| 65 | Et | 1,2-phenylene | 2-CO₂H-5-Me-phenyl | 412.2 |

TABLE 2

(1e) Structure: indazole core with 6-carboxamidine, N1-R⁴, and 3-CH₂-A-B substituent.

| Ex | R⁴ | A | B | MS (M + 1) |
|---|---|---|---|---|
| 101 | Et | 1,2-phenylene | 2-CO₂H-4-OMe-phenyl | 429.2 |
| 102 | Et | 1,2-phenylene | 2-CO₂Et-4-OMe-phenyl | 457.2 |
| 103 | Et | 5-CONH(—CH₂-3-pyridyl)-1,2-phenylene | 2-CO₂H-4-OMe-phenyl | 563.2 |
| 104 | Et | 1,2-phenylene | 2-CO₂H-4-Me-phenyl | 413.2 |
| 105 | Et | 5-CONH(—CH₂-3-pyridyl)-1,2-phenylene | 2-CO₂H-4-Cl-phenyl | 567.2 |
| 106 | Et | 5-CONH(—CH₂-3-pyridyl)-1,2-phenylene | 2-CO₂H-4-Me-phenyl | 547.2 |
| 107 | Et | 5-CONH(—CH₂-(5-Me-2-pyrazinyl)-1,2-phenylene | 2-CO₂H-4-OMe-phenyl | 578.2 |
| 108 | Et | 5-CONH(—CH₂-(5-Me-2-pyrazinyl))-1,2-phenylene | 2-CO₂H-4-Me-phenyl | 562.4 |
| 109 | Et | 5-CONH(—CH₂-2-pyrimidinyl)-1,2-phenylene | 2-CO₂H-4-Me-phenyl | 548.1 |
| 110 | Et | 5-CONH(—CH₂-2-pyrimidinyl)-1,2-phenylene | 2-CO₂H-4-OMe-phenyl | 564.1 |

TABLE 3

(1e) Structure: N-Et indole with R¹ at 6-position, 3-CH₂-biphenyl bearing CONHR⁷, CO₂H, and R¹¹ substituents.

| Ex | R¹ | R⁷ | R¹¹ | MS (M + 1) |
|---|---|---|---|---|
| 201 | —C(N=OH)NH₂ | —CH₂-(2-pyridyl) | OMe | 578.3 |
| 202 | —C(N=OH)NH₂ | —CH₂-(5-Me-2-pyrazinyl) | Me | 577.3 |
| 203 | —C(N=OH)NH₂ | —CH₂-(1,2,4-triazolyl) | OMe | 568.3 |
| 204 | —CH₂NH₂ | —CH₂-(2-pyridyl) | OMe | 532.4 |

Utility

The compounds of this invention are inhibitors of factor XIa and are useful as anticoagulants for the treatment or prevention of thromboembolic disorders in mammals (i.e., factor XIa-associated disorders). In general, a thromboembolic disorder is a circulatory disease caused by blood clots (i.e., diseases involving fibrin formation, platelet activation, and/or platelet aggregation). The term "Thromboembolic disorders" as used herein includes arterial cardiovascular thromboembolic disorders, venous cardiovascular or cerebovascular thromboembolic disorders, and thromboembolic disorders in the chambers of the heart. The term "thromboembolic disorders" as used herein also includes specific disorders selected from, but not limited to, unstable angina or other acute coronary syndromes, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g., after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of serine proteases involved in the coagulation cascade and/or contact activation system, more specifically, inhibition of the coagulation factors: factor XIa, factor VIIa, factor Ixa, factor Xa, plasma kallikrein or thrombin.

The compounds of this invention also are inhibitors of plasma kallikrein and are useful as anti-inflammatory agents for the treatment or prevention of diseases associated with an activation of the contact activation system (i.e., plasma kallikrein associated disorders). In general, a contact activation system disorder is a disease caused by activation of blood on artificial surfaces, including prosthetic valves or other implants, indwelling catheters, stents, cardiopulmonary bypass, hemodialysis, microorganism (e.g., bacteria, virus), or other procedures in which blood is exposed to an artificial surface that promotes contact activation, blood clots (i.e., diseases involving fibrin formation, platelet activation, and/or platelet aggregation). It also includes systemic inflammatory response syndrome, sepsis, acute respiratory dystress syndrome, hereditary angioedema or other inherited or aquired deficencies of contact activation components or their inhibitors (plasma kallikrein, factor XIIa, high molecular weight kininogen, C1-esterase inhibitor). It may also include acute and chronic inflammations of joints, vessels, or other mammalian organs.

The effectiveness of compounds of the present invention as inhibitors of the coagulation factors XIa, VIIa, IXa, Xa, plasma kallikrein or thrombin, can be determined using a relevant purified serine protease, respectively, and an appropriate synthetic substrate. The rate of hydrolysis of the chromogenic or fluorogenic substrate by the relevant serine protease was measured both in the absence and presence of compounds of the present invention. Hydrolysis of the substrate resulted in the release of pNA (para nitroaniline), which was monitored spectrophotometrically by measuring the increase in absorbance at 405 nm, or the release of AMC (amino methylcoumarin, which was monitored spectrofluorometrically by measuring the increase in emission at 460 nm with excitation at 380 nm. A decrease in the rate of absorbance or fluorescence change in the presence of inhibitor is indicative of enzyme inhibition. Such methods are known to one skilled in the art. The results of this assay are expressed as the inhibitory constant, $K_i$.

Factor XIa determinations were made in 50 mM HEPES buffer at pH 7.4 containing 145 mM NaCl, 5 mM KCl, and 0.1% PEG 8000 (polyethylene glycol; JT Baker or Fisher Scientific). Determinations were made using purified human Factor XIa at a final concentration of 75-200 pM (Haematologic Technologies) and the synthetic substrate S-2366 (pyroGlu-Pro-Arg-pNA; Chromogenix) at a concentration of 0.0002-0.00025 M. In general, preferred compounds of the present invention, such as the particular compounds disclosed in the above examples, have been identified to exhibit $K_i$'s of equal to or less than 15 μM in the Factor XIa assay, thereby demonstrating the utility of these preferred compounds of the present invention as especially effective inhibitors of coagulation Factor XIa. More preferred compounds have $K_i$'s of equal to or less than 5 μM, preferably equal to or less than 1 μM, more preferably equal to or less than 0.5 μM.

Factor VIIa determinations were made in 0.005 M calcium chloride, 0.15 M sodium chloride, 0.05 M HEPES buffer containing 0.5% PEG 8000 at a pH of 7.4. Determinations were made using purified human Factor VIIa (Haematologic Technologies) or recombinant human Factor VIIa (Novo Nordisk) at a final assay concentration of 2-5 nM, recombinant soluble tissue factor at a concentration of 18-35 nM and the synthetic substrate H-D-Ile-Pro-Arg-pNA (S-2288; Chromogenix or BMPM-2; AnaSpec) at a concentration of 0.001 M. In general, compounds tested in the Factor VIIa assay are considered to be active if they exhibit a $K_i$ of equal to or less than 15 μM.

Factor IXa determinations were made in 0.005 M calcium chloride, 0.1 M sodium chloride, 0.05 M TRIS base and 0.5% PEG 8000 at a pH of 7.4. Determinations were made using purified human Factor IXa (Haematologic Technologies) at a final assay concentration of 20-100 nM and the synthetic substrate PCIXA2100-B (CenterChem) or Pefafluor IXa 3688 (H-D-Leu-Ph'Gly-Arg-AMC; CenterChem) at a concentration of 0.0004-0.0005 M. In general, compounds tested in the Factor IXa assay are considered to be active if they exhibit a $K_i$ of equal to or less than 15 μM.

Factor Xa determinations were made in 0.1 M sodium phosphate buffer at a pH of 7.4 containing 0.2 M sodium chloride and 0.5% PEG 8000. Determinations were made using purified human Factor Xa (Haematologic Technologies) at a final assay concentration of 150-1000 pM and the synthetic substrate S-2222 (Bz-Ile-Glu (gamma-OMe, 50%)-Gly-Arg-pNA; Chromogenix) at a concentration of 0.0002-0.0003 M. In general, compounds tested in the Factor Xa assay are considered to be active if they exhibit a $K_i$ of equal to or less than 15 μM.

Plasma kallikrein determinations were made in 0.1 M sodium phosphate buffer at a pH of 7.4 containing 0.2 M sodium chloride and 0.5% PEG 8000. Determinations were made using purified human kallikrein (Enzyme Research Laboratories) at a final assay concentration of 200 pM and the synthetic substrate S-2302 (H-(D)-Pro-Phe-Arg-pNA; Chromogenix) at a concentration of 0.00008-0.0004 M. The Km value used for calculation of Ki was 0.00005 to 0.00007 M. In general, Compounds tested in the plasma kallikrein assay are considered to be active if they exhibit a $K_i$ of equal to or less than 15 μM.

Thrombin determinations were made in 0.1 M sodium phosphate buffer at a pH of 7.4 containing 0.2 M sodium chloride and 0.5% PEG 8000. Determinations were made using purified human alpha thrombin (Haematologic Technologies or Enzyme Research Laboratories) at a final assay concentration of 200-250 pM and the synthetic substrate S-2366 (pyroGlu-Pro-Arg-pNA; Chromogenix) at a concentration of 0.0002 M. In general, compounds tested in the thrombin assay are considered to be active if they exhibit a $K_i$ of equal to or less than 15 μM.

In general, preferred compounds of the present invention have demonstrated $K_i$ values of equal to or less than 15 μM in at least one of the above assays, thereby confirming the utility of the compounds of the present invention as effective inhibitors of the coagulation cascade and/or contact activation system, and useful as anticoagulants for the prevention or treatment of thromboembolic disorders in mammals and/or as anti-inflammatory agents for the prevention or treatment of inflammatory disorders in mammals.

The Michaelis constant, $K_m$, for substrate hydrolysis by each protease was determined at 25° C. using the method of Lineweaver and Burk. Values of $K_i$ were determined by allowing the protease to react with the substrate in the presence of the inhibitor. Reactions were allowed to go for periods of 20-180 minutes (depending on the protease) and the velocities (rate of absorbance or fluorescence change versus time) were measured. The following relationships were used to calculate $K_i$ values:

$$(v_o - v_s)/v_s = I/(K_i(1 + S/K_m)) \text{ for a competitive inhibitor with one binding site; or}$$

$$v_s/v_o = A + ((B - A)/1 + ((IC_{50}/(I)^n))) \text{ and}$$

$$K_i = IC_{50}/(1 + S/K_m) \text{ for a competitive inhibitor}$$

where:
- $v_o$ is the velocity of the control in the absence of inhibitor;
- $v_s$ is the velocity in the presence of inhibitor;
- I is the concentration of inhibitor;
- A is the minimum activity remaining (usually locked at zero);
- B is the maximum activity remaining (usually locked at 1.0);
- n is the Hill coefficient, a measure of the number and cooperativity of potential inhibitor binding sites;
- $IC_{50}$ is the concentration of inhibitor that produces 50% inhibition under the assay conditions;
- $K_i$ is the dissociation constant of the enzyme:inhibitor complex;
- S is the concentration of substrate; and
- $K_m$ is the Michaelis constant for the substrate.

The effectiveness of compounds of the present invention as inhibitors of the coagulation factors XIa, VIIa, IXa, Xa, or thrombin, can be determined using relevant in vivo thrombosis models, including In Vivo Electrically-induced Carotid Artery Thrombosis Models and In Vivo Rabbit Arterio-venous Shunt Thrombosis Models.

In Vivo Electrically-induced Carotid Artery Thrombosis Model:

The antithrombotic effect of compounds of the present invention can be demonstrated in the electrically-induced carotid artery thrombosis (ECAT) model in rabbits. In this model, rabbits are anesthetized with a mixture of ketamine (50 mg/kg i.m.) and xylazine (10 mg/kg i.m.). A femoral vein and a femoral artery are isolated and catheterized. The carotid artery is also isolated such that its blood flow can be measured with a calibrated flow probe that is linked to a flowmeter. A stainless steel bipolar hook electrode is placed on the carotid artery and positioned caudally in relationship to the flow probe as a means of applying electrical stimulus. In order to protect the surrounding tissue, a piece of Parafilm is placed under the electrode.

Test compounds are considered to be effective as anticoagulants based on their ability to maintain blood flow in the carotid artery following the induction of thrombosis by an electrical stimulus. A test compound or vehicle is given as continuous intravenous infusion via the femoral vein, starting 1 hour before electrical stimulation and continuing to the end of the test. Thrombosis is induced by applying a direct electrical current of 4 mA for 3 min to the external arterial surface, using a constant current unit and a d.c. stimulator. The carotid blood flow is monitored and the time to occlusion (decrease of blood flow to zero following induction of thrombosis) in minutes is noted. The change in observed blood flow is calculated as a percentage of the blood flow prior to induction of thrombosis and provides a measure of the effect of a test compound when compared to the case where no compound is administered. This information is used to estimate the $ED_{50}$ value, the dose that increases blood flow to 50% of the control (blood flow prior to induction of thrombosis) and is accomplished by nonlinear least square regression.

In Vivo Rabbit Arterio-venous Shunt Thrombosis Model:

The antithrombotic effect of compounds of the present invention can be demonstrated in a rabbit arterio-venous (AV) shunt thrombosis model. In this model, rabbits weighing 2-3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The anti-inflammatory effect of these compounds can be demonstrated in an Evans Blue dye extravasation assay using C1-esterase inhibitor deficient mice. In this model, mice are dosed with a compound of the present invention, Evans Blue is injected via the tail vein, and extravasation of the blue dye is determined by spectrophotometric means from tissue extracts.

The ability of the compounds of the current invention to reduce or prevent the systemic inflammatory response syndrome, for example, as observed during on-pump cardiovascular procedures, can be tested in in vitro perfusion systems, or by on-pump surgical procedures in larger mammals, including dogs and baboons. Read-outs to assess the benefit of the compounds of the present invention include for example reduced platelet loss, reduced platelet/white blood cell complexes, reduced neutrophil elastase levels in plasma, reduced activation of complement factors, and reduced activation and/or consumption of contact activation proteins (plasma kallikrein, factor XII, factor XI, high molecular weight kininogen, C1-esterase inhibitors)

The utility of the compounds of the current invention to reduce or prevent the morbidity and/or mortality of sepsis can be assessed by injecting a mammalian host with bacteria or viruses or extracts there of and compounds of the present invention. Typical read-outs of the efficacy include changes in the LD50 and blood pressure preservation.

The compounds of the present invention may also be useful as inhibitors of additional serine proteases, notably human thrombin, human plasma kallikrein and human plasmin. Because of their inhibitory action, these compounds are indicated for use in the prevention or treatment of physiological reactions, including blood coagulation, fibrinolysis, blood pressure regulation and inflammation, and wound healing catalyzed by the aforesaid class of enzymes. Specifically, the compounds have utility as drugs for the treatment of diseases arising from elevated thrombin activity of the aforementioned serine proteases, such as myocardial infarction, and as reagents used as anticoagulants in the processing of blood to plasma for diagnostic and other commercial purposes.

The compounds of the present invention can be administered alone or in combination with one or more additional therapeutic agents. These include other anti-coagulant or coagulation inhibitory agents, anti-platelet or platelet inhibitory agents, anti-inflammatory agents, thrombin inhibitors, or thrombolytic or fibrinolytic agents.

The compounds are administered to a mammal in a therapeutically effective amount. By "therapeutically effective amount" it is meant an amount of a compound of the present invention that, when administered alone or in combination with an additional therapeutic agent to a mammal, is effective to treat (i.e. prevent, inhibit or ameliorate) the thromboembolic and/or inflammatory disease condition or treat the progression of the disease in a host.

The compounds of the invention are preferably administered alone to a mammal in a therapeutically effective amount. However, the compounds of the invention can also be administered in combination with an additional therapeutic agent, as define below, to a mammal in a therapeutically effective amount. When administered in a combination, the combination of compounds is preferably, but not necessarily, a synergistic combination. Synergy, as described for example by Chou and Talalay, *Adv. Enzyme Regul.* 1984, 22, 27-55, occurs when the effect (in this case, inhibition of the desired target) of the compounds when administered in combination is greater than the additive effect of the compounds when administered alone as a single agent. In general, a synergistic effect is most clearly demonstrated at suboptimal concentrations of the compounds. Synergy can be in terms of lower cytotoxicity, increased anticoagulant effect, or some other beneficial effect of the combination compared with the individual components.

By "administered in combination" or "combination therapy" it is meant that the compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect.

Compounds which can be administered in combination with the compounds of the present invention include, but are not limited to, anticoagulants, anti-thrombin agents, anti-platelet agents, fibrinolytics, hypolipidemic agents, antihypertensive agents, and anti-ischemic agents.

Other anticoagulant agents (or coagulation inhibitory agents) that may be used in combination with the compounds of this invention include warfarin, heparin (either unfractionated heparin or any commercially available low molecular weight heparin, for example LOVANOX™), aprotinin, synthetic pentasaccharide, direct acting thrombin inhibitors including hirudin and argatroban, as well as other factor VIIa, VIIIa, IXa, Xa, XIa, thrombin, TAFI, and fibrinogen inhibitors known in the art.

The term anti-platelet agents (or platelet inhibitory agents), as used herein, denotes agents that inhibit platelet function, for example, by inhibiting the aggregation, adhesion or granular secretion of platelets. Such agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, and piroxicam, including pharmaceutically acceptable salts or prodrugs thereof. Of the NSAIDS, aspirin (acetylsalicylic acid or ASA), and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, phosphodiesterase-III (PDE-III) inhibitors (e.g., dipyridamole, cilostazol), and PDE V inhibitors (such as sildenafil), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use. The compounds of the present invention may also be dosed in combination with aprotinin.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin), endothelial cell activation, inflammatory reactions, and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin and argatroban, including pharmaceutically acceptable salts and prodrugs thereof. Boroarginine derivatives and boropeptides include N-acetyl and peptide derivatives of boronic acid, such as C-terminal alpha-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytic (or fibrinolytic) agents (or thrombolytics or fibrinolytics), as used herein, denotes agents that lyse blood clots (thrombi). Such agents include tissue plasminogen activator (TPA, natural or recombinant) and modified forms thereof, anistreplase, urokinase, streptokinase, tenecteplase (TNK), lanoteplase (nPA), factor VIIa inhibitors, PAI-I inhibitors (i.e., inactivators of tissue plasminogen activator inhibitors), alpha-2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in European Patent Application No. 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K$^+$ channel openers such as $I_{Ach}$ inhibitors, and $I_{Kur}$ inhibitors (e.g., compounds such as those disclosed in WO01/40231).

The term antihypertensive agents, as used herein, include: alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; angiotensin-converting enzyme (ACE) inhibitors (e.g., captopril, lisinopril, fosinopril, enalapril, ceranopril, cilazopril, delapril, pentopril, quinapril, ramipril, lisinopril); angiotensin-II receptor antagonists (e.g., irbestatin, losartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual ACE/NEP inhibitors, e.g., omapatrilat, gemopatrilat, nitrates); and β-blockers (e.g., propanolol, nadolo, or carvedilol).

Examples of suitable cardiac glycosides for use in combination with the compounds of the present invention include digitalis and ouabain.

Examples of suitable mineralocorticoid receptor antagonists for use in combination with the compounds of the present invention include sprionolactone and eplirinone.

Examples of suitable cholesterol/lipid lowering agents and lipid profile therapies for use in combination with the compounds of the present invention include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protein tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., conjugated estrogens) and estradiol.

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each. A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of thrombin, Factor VIIa, IXa, Xa, XIa, and/or plasma kallikrein. Such compounds may be provided in a commercial kit, for example, for use in pharmaceutical research involving thrombin, Factor VIIa, IXa, Xa, XIa, and/or, plasma kallikrein. XIa. For example, a compound of the present invention could be used as a reference in an assay to compare its known activity to a compound with an unknown activity. This would ensure the experimentor that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving thrombin, Factor VIIa, IXa, Xa, XIa, and/or plasma kallikrein. For example, the presence of thrombin, Factor VIIa, IXa, Xa XIa, and/or plasma kallikrein in an unknown sample could be determined by addition of the relevant chromogenic substrate, for example S2366 for Factor XIa, to a series of solutions containing test sample and optionally one of the compounds of the present invention. If production of pNA is observed in the solutions containing test sample, but not in the presence of a compound of the present invention, then one would conclude Factor XIa was present.

Extremely potent and selective compounds of the present invention, those having $K_i$ values less than or equal to 0.001 μM against the target protease and greater than or equal to 0.1 μM against the other proteases, may also be used in diagnostic assays involving the quantitation of thrombin, Factor VIIa, Ixa, Xa, XIa, and/or plasma kallikrein in serum samples. For example, the amount of Factor XIa in serum samples could be determined by careful titration of protease activity in the presence of the relevant chromogenic substrate, S2366, with a potent and selective Factor XIa inhibitor of the present invention.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic and/or inflammatory disorder (as defined previously). In another embodiment, the package insert states that the pharmaceutical composition can be used in combination (as defined previously) with a second therapeutic agent to treat a thromboembolic and/or inflammatory disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5-95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, Mack Publishing Company, a standard reference text in this field.

Where the compounds of this invention are combined with other anticoagulant agents, for example, a daily dosage may be about 0.1 to 100 milligrams of the compound of the present invention and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of the present invention and about 50 to 150 milligrams of the anti-platelet agent, preferably about 0.1 to 1 milligrams of the compound of the present invention and about 1 to 3 milligrams of antiplatelet agents, per kilogram of patient body weight.

Where the compounds of the present invention are administered in combination with thrombolytic agent, typically a daily dosage may be about 0.1 to 1 milligrams of the compound of the present invention, per kilogram of patient body weight and, in the case of the thrombolytic agents, the usual dosage of the thrombolyic agent when administered alone may be reduced by about 70-80% when administered with a compound of the present invention.

Where two or more of the foregoing second therapeutic agents are administered with the compound of the present invention, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

What is claimed is:

1. A compound of Formula (Ic):

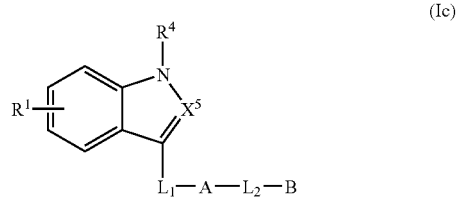

or a stereoisomer or a pharmaceutically acceptable salt or a solvate thereof, wherein:
$L_1$ is —$CH_2$;
$L_2$ is a bond;

A is phenylene substituted with 0-2 $R^{11}$, or pyridylene substituted with 0-2 $R^{11}$;

provided that the groups $L_1$ and $L_2$ are attached to said phenylene or heteroaryl in a ortho- or meta-orientation;

B is phenyl substituted with 0-2 $R^{11}$ and 0-1 $R^{12}$, a 5- to 6-membered heterocycle substituted with 0-2 $R^{11}$ and 0-1 $R^{12}$ and selected from: pyrrolidinyl, pyrrolyl, pyrrolinyl, pyrazolyl, oxazolyl, imidazolyl, imidazolinyl, pyrazolyl, pyrazolinyl, isoxazolyl, isothiazolyl, triazolyl, tetrazolyl, pyranyl, piperidyl, piperazinyl, pyridyl, pyrimidinyl, pyrazinyl, and triazinyl;

$X^5$ is CH or N;

$R^1$ is —C(=NH)NH$_2$, —C(=NOH)NH$_2$, —CONH$_2$, —CH$_2$NH$_2$, or —C(O)NR$^{7a}$R$^8$;

$R^4$ is H, —(CH$_2$)$_r$—CONR$^{7a}$R$^8$, $C_{1-4}$ alkyl, —(CH$_2$)$_r$—$C_{3-7}$ cycloalkyl, —(CH$_2$)$_r$-phenyl, or —(CH$_2$)$_r$-5- to 6-membered heteroaryl selected from: pyrrolyl, pyrazolyl, oxazolyl, thiazolyl, imidazolyl, isoxazolyl, isothiazolyl, triazolyl, tetrazolyl, pyridazinyl, pyridyl, pyrimidinyl, pyrazinyl, and triazinyl;

$R^7$ is, independently at each occurrence, H, $C_{1-6}$ alkyl, or benzyl;

$R^{7a}$ is, independently at each occurrence, H, $C_{1-4}$ alkyl substituted with 0-1 $R^{7a}$ or 0-1 $R^{7c}$, $C_{3-7}$ cycloalkyl substituted with 0-2 $R^f$, phenyl substituted with 0-3 $R^f$, or a 5-6 membered heterocycle comprising: carbon atoms and 1-4 heteroatoms selected from N, O, and S(O)$_p$, and substituted 0-3 $R^f$;

$R^{7b}$ is =O, OR$^g$, F, Cl, Br, I, CN, NO$_2$, —NR$^7$R$^8$, —C(O)R$^g$, —CO$_2$R$_g$, —NR$^8$C(O)R$^g$, —CONR$^8$R$^9$, —NR$^8$C(O)NR$^8$R$^9$, —SO$_2$NR$^8$R$^9$, —NR$^8$SO$_2$NR$^8$R$^9$, —NR$^8$SO$_2$-$C_{1-4}$ allyl, —NR$^8$SO$_2$CF$_3$, —NR$^8$SO$_2$-phenyl, —S(O)$_2$CF$_3$, —S(O)$_p$-$C_{1-4}$ alkyl, —S(O)$_p$-phenyl, or —(CF$_2$)$_r$CF$_3$;

$R^{7c}$ is $C_{3-10}$ carbocycle substituted with 0-3 $R^f$ or a 5-12 membered heterocycle comprising: carbon atoms and 1-4 heteroatoms selected from N, O, and S(O)$_p$, and substituted 0-3 $R^f$;

$R^8$ is, independently at each occurrence, H, $C_{1-6}$ alkyl, or benzyl;

$R^9$ is, independently at each occurrence, H, $C_{1-6}$ alkyl, or benzyl;

$R^{10}$ is, independently at each occurrence, H, $C_{1-6}$ alkyl substituted with 0-2 $R^{10a}$, $C_{2-6}$ alkenyl substituted with 0-2 $R^{10a}$, $C_{2-6}$ alkynyl substituted with 0-2 $R^{10a}$, (CH$_2$)$_r$$C_{3-10}$ carbocycle substituted with 0-3 $R^{10b}$, or —(CH$_2$)$_r$-5-10 membered heterocycle comprising: carbon atoms and 1-4 heteroatoms selected from N, O, and S(O)$_p$, and substituted with 0-3 $R^{10b}$;

$R^{10a}$ is, independently at each occurrence, H, $C_{1-4}$ alkyl, OR$^a$, F, =O, CF$_3$, CN, NO$_2$, —C(O)R$^a$, —CO$_2$R$^a$, —CONR$^{7a}$R$^8$, or —S(O)$_p$R$^c$;

$R^{10b}$ is, independently at each occurrence, H, =O, OR$^a$, F, Cl, Br, I, CN, NO$_2$, —NR$^7$R$^8$, —C(O)R$^a$, —CO$_2$R$^a$, —NR$^8$C(O)R$^a$, —CONR$^{7a}$R$^8$, —SO$_2$NR$^8$R$^9$, —NR$^8$SO$_2$NR$^8$R$^9$, —NR$^8$SO$_2$-$C_{1-4}$ alkyl, —NR$^8$SO$_2$CF$_3$, —NR$^8$SO$_2$-phenyl, —S(O)$_2$CF$_3$, —S(O)$_p$—$C_{1-4}$ alkyl, —S(O)$_p$-phenyl, —(CF$_2$)$_r$CF$_3$, $C_{1-4}$ alkyl substituted with 0-2 $R^e$, $C_{2-4}$ alkenyl substituted with 0-2 $R^e$, or $C_{2-4}$ alkynyl substituted with 0-2 $R^e$;

$R^{11}$ is, independently at each occurrence, H, F, Cl, CF$_3$, $C_{1-6}$ alkyl, —(CH$_2$)$_r$—OR$^a$, CN, —(CH$_2$)$_r$NR$^7$R$^8$, —(CH$_2$)$_r$—C(=NR$^8$)NR$^7$R$^9$, —C(O)R$^a$, —CO$_2$R$^a$, —(CH$_2$)$_r$NR$^8$C(O)R$^a$, —NR$^8$C(O)OR$^c$, —CONR$^{7a}$R$^8$, —NR$^8$C(O)NR$^8$R$^{10}$, —SO$_2$NR$^8$R$^{10}$, —NR$^8$SO$_2$NR$^8$R$^{10}$, or —NR$^8$SO$_2$-$C_{1-4}$ alkyl;

$R^{12}$ is —CONR$^{7a}$R$^8$, —(CH$_2$)$_r$CO$_2$R$^{12a}$, —CH$_2$OR$^{12a}$, —SO$_2$NHCO$_2$R$^{12a}$, —CONHSO$_2$R$^{12b}$, —NHSO$_2$R$^{12b}$, —SO$_2$NHCO$_2$R$^{12a}$, —CONHSO$_2$R$^{12b}$, —NHSO$_2$R$^{12b}$, or —(CH$_2$)$_r$-5-tetrazolyl;

$R^{12a}$ is, independently at each occurrence, H or $C_{1-6}$ alkyl;

$R^{12b}$ is, independently at each occurrence, $C_1$-$C_4$ alkyl substituted with 0-1 $R^{12}$c, $C_2$-$C_4$ alkenyl substituted with 0-1 $R^{12c}$, $C_2$-$C_4$ alkynyl substituted with 0-1 $R^{12c}$, —CH$_2$)$_r$$C_3C_7$ carbocycle substituted with 0-2 $R^{12c}$, or —(CH$_2$)$_r$-5-6 membered heterocycle comprising: carbon atoms and 1-4 heteroatoms selected from N, O, and S(O)$_p$, and substituted with 0-2 $R^{12c}$;

$R^{12c}$ is, independently at each occurrence, H, F, Cl, Br, I, CF$_3$, OCF$_3$, CN, NO$_2$, OR$^a$, —CO$_2$R$^a$, —NR$^7$R$^8$, —SO$_2$R$^c$, $C_1$-$C_6$ alkyl, $C_2$-$C_6$ alkenyl, $C_2$-$C_6$ alkynyl, —(CH$_2$)$_r$-$C_{3-10}$ carbocycle substituted with 0-3 $R^d$; or —(CH$_2$)$_r$-5-10 membered heterocycle comprising: carbon atoms and 1-4 heteroatoms selected from N, O, and S(O)$_p$, and substituted with 0-3 $R^d$;

$R^a$ is, independently at each occurrence, H, $C_{1-4}$ alkyl, —(CH$_2$)$_r$-$C_{3-7}$ cycloalkyl, —(CH$_2$)$_r$$C_{6-10}$ aryl, or —(CH$_2$)$_r$-5-10 membered heteroaryl, wherein said aryl or heteroaryl groups are optionally substituted with 0-2 $R^f$;

$R^c$ is, independently at each occurrence, $C_{1-4}$ alkyl, phenyl or benzyl;

$R^d$ is, independently at each occurrence, H, =O, OR$^a$, F, Cl, Br, I, CN, NO$_2$, —NR$^7$R$^8$, —C(O)R$^a$, —CO$_2$R$^a$, —NR$^8$C(O)R$^a$, —CONR$^{7a}$R$^8$, —SO$_2$NR$^8$R$^{10}$, —NR$^8$SO$_2$NR$^8$R$^{10}$, —NR$^{10}$SO$_2$—$C_{1-4}$ alkyl, —NR$^{10}$SO$_2$CF$_3$, —NR$^{10}$SO$_2$-phenyl, —S(O)$_2$CF$_3$, —S(O)-$C_{1-4}$ alkyl, —S(O)$_p$phenyl, —(CF$_2$)$_r$CF$_3$, $C_{1-6}$ alkyl substituted with 0-2 $R^a$, $C_{2-6}$ alkenyl substituted with 0-2 $R^e$, or $C_{2-6}$ alkynyl substituted with 0-2 $R_e$;

$R^e$ is, independently at each occurrence, =O, OR$^a$, F, Cl, Br, I, CN, NO$_2$, —NR$^8$R$^9$, —C(O)R$^a$, —CO$_2$R$^a$, —NR$^8$C(O)R$^a$, —CONR$^{7a}$R$^8$, —SO$_2$NR$^8$R$^9$, —NR$^8$SO$_2$NR$^8$R$^9$, —NR$^8$SO$_2$-$C_{1-4}$ alkyl, —NR$^8$SO$_2$CF$_3$, —NR$^8$SO$_2$-phenyl, —S(O)$_2$CF$_3$, —S(O)$_{p\text{-}c1-4}$ alkyl, —S(O)$_p$phenyl, or —(CF$_2$)$_r$CF$_3$;

$R^f$ is, independently at each occurrence, H, =O, —(CH$_2$)$_r$OR$^g$, F, Cl, Br, CF$_3$, CN, NO$_2$, —NR$^8$R$^9$, —C(O)R$^a$, —C(O)OR$^a$, —NR$^8$C(O)R$^a$, —C(O)NR$^8$R$^9$, —SO$_2$NR$^8$R$^9$, -NR$^8$SO$_2$-$C_{1-4}$ alkyl, —NR$^8$SO$_2$CF$_3$, —S(O)$_2$CF$_3$, —S(O)$_{p\text{ -}c1-4}$ alkyl, $C_{1-6}$ alkyl, $C_2$-$C_6$ alkenyl, or $C_2$-$C_6$ alkynyl;

$R^g$ is, independently at each occurrence, H or $C_{1-4}$ alkyl;

p, at each occurrence, is selected from 0, 1, and 2; and r, at each occurrence, is selected from 0, 1, 2, 3, and 4.

2. A compound according to claim 1, wherein:

B is phenyl substituted with 0-2 $R^{11}$ and 0-1 $R^{12}$, pyridyl substituted with 0-2 $R^{11}$ and 0-1 $R^{12}$, pyrrolidinyl substituted with 0-2 $R^{11}$ and 0-1 $R^{12}$, pyrazolyl substituted with 0-2 $R^{11}$ and 0-1 $R^{12}$, or piperidyl substituted with 0-2 $R^{11}$ and 0-1 $R^{12}$;

$R^1$ is —C(=NH)NH$_2$, —C(=NOH)NH$_2$, —CONH$_2$, or —CH$_2$NH$_2$;

$R^{11}$ is, independently at each occurrence, H, F, Cl, OH, OMe, CN, Me, Et, Pr, i-Pr, Bu, i-Bu, t-Bu, —NH$_2$, —CH$_2$OH, —CO$_2$H, —CO$_2$Me, —CO$_2$Lt, —CONH$_2$, —NHCOMe, —NHCOEt, —NHCOPr, —NHCO(i-Pr), —NHCO(i-Bu), —CONHMe, —CONHEt, —CONHPr, —CONH(i-Bu), —CONHCH$_2$CONH$_2$, —CONHCH$_2$CONHMe, —CONHCH$_2$CONHEt, —CONH(—CH$_2$-cyclopropyl), —CONH(—CH$_2$-cyclohexyl), —CONHBn, —CONH(—CH$_2$-2-oxazolyl), —CONH(—CH₂-1,2,4-triazolyl), —CONH(—CH₂-2-pyridyl), —CONH(-(CH₉₂-2-pyridyl), —CONH(—CH₂-3-pyridyl), —CONH(—CH₂-4-pyridyl), —CONH(—CH₂-2-pyrimidinyl), —CONH(—CH₂-3,4,5,6-tetrahydro-2-pyrimidinyl), —CONH(—CH₂-(5-Me-2-pyrazinyl)), —SO₂NH₂, or —CONHSO₂Me; and
R¹² is —OH, —OMe, —CH₂OH, —CO₂H, —CH₂(CO₂H), —CO₂Me, —CO₂Et, —SO₂NH₂, or —CONH₂.

3. A compound of Formula (Id):

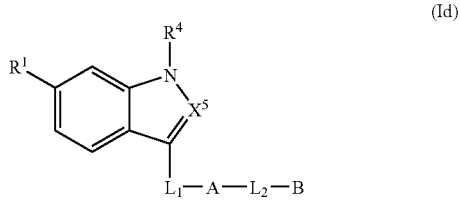

(Id)

or a stereoisomer or a pharmaceutically acceptable salt or solvate thereof, wherein:
L₁ is —CH₂;
L₂ is a bond;
A is 1,2-phenylene, 5-CO₂H-1,2-phenylene, 5-CONHMe-1,2-phenylene, 5-CONHEt-1,2-phenylene, 5-CONHPr-1,2-phenylene, 5-CONHBn-1,2-phenylene, 5-CONHCH₂CONH₂-1,2-phenylene, 5-CONHCH₂CONHMe-1,2-phenylene, 5-CONHCH₂CONHLt-1,2-phenylene, 5-CONH(—CH₂-cyclopropyl)-1,2-phenylene, 5-CONH-(—CH₂-cyclohexyl)-1,2-phenylene, 5-CONH-(—CH₂-(4-COMe-Ph))-1,2-phenylene, 5-CONH(—CH₂-2-oxazolyl)-1,2-phenylene, 5-CONH(—CH₂-1,2,4-triazolyl)-1,2-phenylene, 5-CONH(—CH₂-2-pyridyl)-1,2-phenylene, 5-CONH(—CH₂-3-pyridyl)-1,2-phenylene, 5-CONH(—CH₂-4-pyridyl)-1,2-phenylene, 5-CONH(—CH₂-2-pyrimidinyl)-1,2-phenylene, 5-CONH(—CH₂-3,4,5,6-tetrahydro-2-pyrimidinyl)-1,2-phenylene, 5-CONH(—CH₂-(5-Me-2-pyrazinyl))-1,2-phenylene, 5-CONH(—CH₂-2-thiazolyl)-1,2-phenylene, S —CONH(—CH₂-4-thiazolyl)-1,2-phenylene, 5-CONH(—CH₂-5-thiazolyl)-1,2-phenylene, 5-CONH(—CH₂-2-imidazolyl)-1,2-phenylene, 5-CONH(—CH₂-4-imidazolyl)-1,2-phenylene, 5-NHCOMe-1,2-phenylene, 5-NHCO(i-Bu)-1,2-phenylene, 1,3-phenylene, 5-NHCOMe-1,3-phenylene, 5-NHCOEt-1,3-phenylene, or 5-NHCOPr-1,3-phenylene, wherein the attachment to L₂ is at carbon 1 of said phenylene groups;
B is 2-CO₂H-phenyl, 2-CO₂Et-phenyl, 2-CONH₂-phenyl, 2-CONHSO₂Me-phenyl, 2-SO₂NH₂-phenyl, 2-CH₂OH-4-OMe-phenyl, 2-CO₂H-3-Me-phenyl, 2-CO₂H-4-Me-phenyl, 2-COY-S -Me-phenyl, 2-CO₂Et-4-Me-phenyl, 2-CO₂H-4-Cl-phenyl, 2-CO₂Et-4-Cl-phenyl, 2-CO₂H-4-OMe-phenyl, 2-CO₂Et-4-OMe-phenyl, 2-CO₂H-4-CONH₂-phenyl, 2-CO₂H-4,5-methylenedioxyphenyl, 3-CO₂H-6-Me-2-pyridyl, 3-CO₂H-5-Cl-2-pyridyl, 2-CO₂H-1-pyrrolidinyl, 2-CO₂Et-1-pyrrolidinyl, 1-Me-3-CO₂H-4-pyrazolyl, 1-Me-5-CO₂H-4-pyrazolyl, or 2-CO₂H-1-piperidyl;
X₅ is CH or N;
R¹ is —C(=NH)NH₂ or —C(=NOH)NH₂; and
R⁴ is H, Me, Et, Pr, i-Bu, Bn, —CONH₂, —(CH₂)₂CONH₂, —(CH₂)₃CONH₂, —SO₂Me, —CH₂-cyclopropyl, or —CH₂-3-pyridyl.

4. A compound according to claim 3, wherein:
A is 1,2-phenylene, 5-CO₂H-1,2-phenylene, 5-CONHMe-1,2-phenylene, 5-CONHEt-1,2-phenylene, 5-CONHPr-1,2-phenylene, 5-CONHBn-1,2-phenylene, 5-CONHCH₂CONH₂-1,2-phenylene, 5-CONHCH₂CONHMe-1,2-phenylene, 5-CONHCH₂CONHEt-1,2-phenylene, 5-CONH(—CH₂-cyclopropyl)-1,2-phenylene, 5-CONH-(—CH₂-cyclohexyl)-1,2-phenylene, 5-CONH-(—CH₂-(4-COMe-Ph))-1,2-phenylene, 5-CONH(—CH₂-2-oxazolyl)-1,2-phenylene, 5-CONH(—CH₂-1,2,4-triazolyl)-1,2-phenylene, 5-CONH(—CH₂-2-pyridyl)-1,2-phenylene, 5-CONH(—CH₂-3-pyridyl)-1,2-phenylene, 5-CONH(—CH₂-4-pyridyl)-1,2-phenylene, 5-CONH(—CH₂-2-pyrimidinyl)-1,2-phenylene, 5-CONH(—CH₂-3,4,5,6-tetrahydro-2-pyrimidinyl)-1,2-phenylene, 5-CONH(—CH₂-(5-Me-2-pyrazinyl))-1,2-phenylene, 5-CONH(—CH₂-2-thiazolyl)-1,2-phenylene, 5-CONH(—CH₂-4-thiazolyl)-1,2-phenylene, 5-CONH(—CH₂-5-thiazolyl)-1,2-phenylene, 5-CONH(—CH₂-2-imidazolyl)-1,2-phenylene, 5-CONH(—CH₂-4-imidazolyl)-1,2-phenylene, or 1,3-phenylene, wherein the attachment to L₂ is at carbon 1 of said phenylene groups;
B is 2-CO₂H-phenyl, 2-CO₂Et-phenyl, 2-CONH₂-phenyl, 2-CONHSO₂Me-phenyl, 2-SO₂NH₂-phenyl, 2-CH₂OH-4-OMe-phenyl, 2-CO₂H-3-Me-phenyl, 2-CO₂H-4-Me-phenyl, 2-CO₂H-5-Me-phenyl, 2-CO₂Et-4-Me-phenyl, 2-CO₂H-4-Cl-phenyl, 2-CO₂Et-4-Cl-phenyl, 2-CO₂H-4-OMe-phenyl, 2-CO₂Et-4-OMe-phenyl, 2-CO₂H-4-CONH₂-phenyl, 2-CO₂H-4,5-methylenedioxyphenyl, 3-CO₂H-6-Me-2-pyridyl, 3-CO₂H-5-Cl-2-pyridyl, 2-CO₂H-1-pyrrolidinyl, 2-CO₂Et-1-pyrrolidinyl, 1-Me-3-CO₂H-4-pyrazolyl, 1-Me-5-CO₂H-4-pyrazolyl, or 2-CO₂H-1-piperidyl;
X5 is CH; and R⁴ is H, Me, Et, Pr, i-Bu, Bn, —CONH₂, —(CH₂)₂CONH₂, —(CH₂)₃CONH₂, —CH₂-cyclopropyl, or —CH₂-3-pyridyl.

5. A compound according to claim 4, wherein:
B is 2-CO₂H-phenyl, 2-CO₂Et-phenyl, 2-CH₂OH-4-OMe-phenyl, 2-CO₂H-3-Me-phenyl, 2-CO₂H-4-Me-phenyl, 2-CO₂H-S -Me-phenyl, 2-CO₂H-4-Cl-phenyl, 2-CO₂H-4-OMe-phenyl, 2-CO₂H-4-CONH₂-phenyl, 2-CO₂H-3,4-methylenedioxyphenyl, 3-CO₂H-6-Me-2-pyridyl, 3-CO₂H-5-Cl-2-pyridyl, 2-CO₂H-1-pyrrolidinyl, 1-Me-3-CO₂H-4-pyrazolyl, or 1-Me-5-CO₂H-4-pyrazolyl.

6. A compound according to claim 3, wherein:
A is 1,2-phenylene, 5-CONH(—CH₂-3-pyridyl)-1,2-phenylene, 5-CONH(—CH₂-(5-Me-2-pyrazinyl))-1,2-phenylene, or 5-CONH(—CH₂-2-pyrimidinyl)-1,2-phenylene;
B is 2-CO₂H-4-Me-phenyl, 2-CO₂H-4-Cl-phenyl, 2-CO₂H-4-OMe-phenyl, or 2-CO₂Et-4-OMe-phenyl;
X⁵ is N; and
R⁴ is Et.

7. A compound according to claim 1, wherein the compound is selected from:
2'-(6-carbamimidoyl-1H-indol-3-ylmethyl)-4-methoxy-biphenyl-2-carboxylic acid;
2'-(1-benzyl-6-carbamimidoyl-1H-indol-3-ylmethyl)-4-methoxy-biphenyl-2-carboxylic acid;
2'-(6-carbamimidoyl-1-ethyl-1H-indol-3-ylmethyl)-4-methoxy-biphenyl-2-carboxylic acid;
2'-(6-carbamimidoyl-1-isobutyl-1H-indol-3-ylmethyl)-4-methoxy-biphenyl-2-carboxylic acid;

2'-(6-carbamimidoyl-1-cyclopropylmethyl-1H-indol-3-ylmethyl)-4-methoxy-biphenyl-2-carboxylic acid;
2'-(6-carbamimidoyl-1-pyridin-3-ylmethyl-1H-indol-3-ylmethyl)-4-methoxy-biphenyl-2-carboxylic acid;
3'-(1-benzyl-6-carbamimidoyl-1H-indol-3-ylmethyl)-4-carbamoyl-biphenyl-2-carboxylic acid;
3'-(6-carbamimidoyl-1-ethyl-1H-indol-3-ylmethyl)-4-carbamoyl-biphenyl-2-carboxylic acid;
3'-(6-carbamimidoyl-1-ethyl-1H-indol-3-ylmethyl)-4-methoxy-biphenyl-2-carboxylic acid;
2'-(6-carbamimidoyl-1-methyl-1H-indol-3-ylmethyl)-4-methoxy-5-methylcarbamoyl-biphenyl-2-carboxylic acid;
2'-(6-carbamimidoyl-1-ethyl-1H-indol-3-ylmethyl)-4-methoxy-5'-methylcarbamoyl-biphenyl-2-carboxylic acid;
2'-(6-carbamimidoyl-1-ethyl-1H-indol-3-ylmethyl)-4-methoxy-5'-[(pyridine-2-ylmethyl)-carbamoyl]-biphenyl-2-carboxylic acid;
2'-(6-carbamimidoyl-1-methyl-1H-indol-3-ylmethyl)-4-methoxy-biphenyl-2-carboxylic acid;
2'-(6-carbamimidoyl-1-propyl-1H-indol-3-ylmethyl)-4-methoxy-biphenyl-2-carboxylic acid;
2'-(6-carbamimidoyl-1-ethyl-1H-indol-3-ylmethyl)-4-methoxy-5'-[(pyridin-3-ylmethyl)-carbamoyl]-biphenyl-2-carboxylic acid;
2'-(6-carbamimidoyl-1-ethyl-1H-indol-3-ylmethyl)-4-methoxy-5'-[(pyridin-4-ylmethyl)-carbamoyl]-biphenyl-2-carboxylic acid;
2'-(6-carbamimidoyl-1-ethyl-1H-indol-3-ylmethyl)-4-methyl-5'-methylcarbamoyl-biphenyl-2-carboxylic acid;
2'-(6-carbamimidoyl-1-ethyl-1H-indol-3-ylmethyl)-4-methyl-5'-[(pyridine-2-ylmethyl)-carbamoyl]-biphenyl-2-carboxylic acid;
2'-(6-carbamimidoyl-1-ethyl-1H-indol-3-ylmethyl)-biphenyl-2-carboxylic acid;
2'-(6-carbamimidoyl-1-ethyl-1H-indol-3-ylmethyl)-5'-ethylcarbamoyl-4-methoxy-biphenyl-2-carboxylic acids;
2'-(6-carbamimidoyl-1-ethyl-1H-indol-3-ylmethyl)-4-methoxy-5'-propylcarbamoyl-biphenyl-2-carboxylic acids;
2'-[6-carbamimidoyl-1-(2-carbamoyl-ethyl)-1H-indol-3-ylmethyl]-4-methoxy-biphenyl-2-carboxylic acids;
2'-[6-carbamimidoyl-1-(2-carbamoyl-propyl)-1H-indol-3-ylmethyl]-4-methoxy-biphenyl-2-carboxylic acids;
6-(6-carbamimidoyl-1-ethyl-1H-indol-3-ylmethyl)-2'-hydroxymethyl-4'-methoxy-biphenyl-3-carboxylic acid (pyridin-2-ylmethyl)-amide;
2'-(6-carbamimidoyl-1-ethyl-1H-indol-3-ylmethyl)-4-chloro-biphenyl-2-carboxylic acid;
5'-benzylcarbamoyl-2'-(6-carbamimidoyl-1-ethyl-1H-indol-3-ylmethyl)-4-methoxy-biphenyl-2-carboxylic acid;
2'-(6-carbamimidoyl-1-ethyl-1H-indol-3-ylmethyl)-5'-(ethylcarbamoylmethyl-carbamoyl)-4-methoxy-biphenyl-2-carboxylic acid;
2'-(6-carbamimidoyl-1-ethyl-1H-indol-3-ylmethyl)-4-methoxy-5'-[(oxazol-2-ylmethyl)-carbamoyl]-biphenyl-2-carboxylic acid;
2'-(6-carbamimidoyl-1-ethyl-1H-indol-3-ylmethyl)-4-methoxy-5'-[(5-methyl-pyrazin-2-ylmethyl)-carbamoyl]-biphenyl-2-carboxylic acids;
2'-(6-carbamimidoyl-1-ethyl-1H-indol-3-ylmethyl)-4-methoxy-5'-[(pyrimidin-2-ylmethyl)-carbamoyl]-biphenyl-2-carboxylic acid;
2'-(6-carbamimidoyl-1-ethyl-1H-indol-3-ylmethyl)-4-methoxy-5'-[(1,4,5,6-tetrahydro-pyrimidin-2-ylmethyl)-carbamoyl]-biphenyl-2-carboxylic acid;
2'-(6-carbamimidoyl-1-ethyl-1H-indol-3-ylmethyl)-4-methoxy-5'-[(1H-[1,2,4]triazol-3-ylmethyl)-carbamoyl]-biphenyl-2-carboxylic acid;
2'-(6-carbamimidoyl-1-ethyl-1H-indol-3-ylmethyl)-4-methyl-5'-[(1H-[1,2,4]triazol-3-ylmethyl)-carbamoyl]-biphenyl-2-carboxylic acid;
2'-(6-carbamimidoyl-1-ethyl-1H-indol-3-ylmethyl)-biphenyl-2-carboxylic acid ethyl ester;
2'-(6-carbamimidoyl-1-ethyl-1H-indol-3-ylmethyl)-5'-(ethylcarbamoylmethyl-carbamoyl)-4-methyl-biphenyl-2-carboxylic acid;
2'-(6-carbamimidoyl-1-ethyl-1H-indol-3-ylmethyl)-4-methyl-5'-[(pyridin-3-ylmethyl)-carbamoyl]-biphenyl-2-carboxylic acid;
5'-benzylcarbamoyl-2'-(6-carbamimidoyl-1-ethyl-1H-indol-3-ylmethyl)-4-methyl-biphenyl-2-carboxylic acid;
2'-(6-Carbamimidoyl-1-ethyl-1H-indol-3-ylmethyl)-4-methyl-5'-[(pyridin-4-ylmethyl)-carbamoyl]-biphenyl-2-carboxylic acid;
2'-(6-carbamimidoyl-1-ethyl-1H-indol-3-ylmethyl)-4-methyl-5'-[(5-methylpyrazin-2-ylmethyl)-carbamoyl]-biphenyl-2-carboxylic acid;
2'-(6-carbamimidoyl-1-ethyl-1H-indol-3-ylmethyl)-4-methyl-5'-propylcarbamoyl-biphenyl-2-carboxylic acid;
2'-(6-carbamimidoyl-1-ethyl-1H-indol-3-ylmethyl)-5'-(cyclopropylmethyl-carbamoyl)-4-methyl-biphenyl-2-carboxylic acid;
2'-(6-carbamimidoyl-1-ethyl-1H-indol-3-ylmethyl)-5'-(methylcarbamoylmethyl-carbamoyl)-4-methyl-biphenyl-2-carboxylic acid;
2'-(6-carbamimidoyl-1-ethyl-1H-indol-3-ylmethyl)-5'-(carbamoylmethyl-carbamoyl)-4-methoxy-biphenyl-2-carboxylic acid;
2'-(6-carbamimidoyl-1-ethyl-1H-indol-3-ylmethyl)-5'-(cyclohexylmethyl-carbamoyl)-4-methyl-biphenyl-2-carboxylic acid;
2'-(6-carbamimidoyl-1-ethyl-1H-indol-3-ylmethyl)-4-chloro-5'-[(5-methyl-pyrazin-2-ylmethyl)-carbamoyl]-biphenyl-2-carboxylic acid;
4-[2-(6-carbamimidoyl-1-ethyl-1H-indol-3-ylmethyl)-phenyl]-2-methyl-2H-pyrazole-3-carboxylic acid;
4-[2-(6-carbamimidoyl-1-ethyl-1H-indol-3-ylmethyl)-phenyl]-1-methyl-1H-pyrazole-3-carboxylic acid;
1-[2-(6-carbamimidoyl-1-ethyl-1H-indol-3-ylmethyl)-phenyl]-pyrrolidine-2-carboxylic acid;
2'-(6-carbamimidoyl-1-ethyl-1H-indol-3-ylmethyl)-4-methyl-5'-[(pyrimidin-2-ylmethyl)-carbamoyl]-biphenyl-2-carboxylic acid;
2'-(6-carbamimidoyl-1-ethyl-1H-indol-3-ylmethyl)-4-methyl-5'-[(1,4,5,6-tetrahydro-pyrimidin-2-ylmethyl)-carbamoyl]-biphenyl-2-carboxylic acid;
6'-(6-carbamimidoyl-1-ethyl-1H-indol-3-ylmethyl)-4-methyl-biphenyl-2,3 dicarboxylic acid;
2'-(6-carbamimidoyl-1-ethyl-1H-indol-3-ylmethyl)-4-methoxy-5'-[(thiazol-2-ylmethyl)-carbamoyl]-biphenyl-2-carboxylic acid;
2'-(6-carbamimidoyl-1-ethyl-1H-indol-3-ylmethyl)-4-methoxy-5'-[(thiazol-4-ylmethyl)-carbamoyl]-biphenyl-2-carboxylic acid;
2'-(6-carbamimidoyl-1-ethyl-1H-indol-3-ylmethyl)-4-methoxy-5'-[(thiazol-5-ylmethyl)-carbamoyl]-biphenyl-2-carboxylic acid;

2'-(6-carbamimidoyl-1-ethyl-1H-indol-3-ylmethyl)-5'-[(1H-imidazol-4-ylmethyl)-carbamoyl]-4-methoxy-biphenyl-2-carboxylic acid;

2'-(6-carbamimidoyl-1-ethyl-1H-indol-3-ylmethyl)-5'-[(1H-imidazol-2-ylmethyl)-carbamoyl]-4-methoxy-biphenyl-2-carboxylic acid;

2'-(6-carbamimidoyl-1-methanesulfonyl-1H-indol-3-ylmethyl)-4-methoxy-biphenyl-2-carboxylic acid;

2-[2-(6-carbamimidoyl-1-ethyl-1H-indol-3-ylmethyl)-phenyl]-5-chioro-nicotinic acid;

6-[2-(6-carbamimidoyl-1-ethyl-1H-indol-3-ylmethyl)-phenyl]-benzo[1,3]dioxole-5-carboxylic acid;

2-[2-(6-carbamimidoyl-1-ethyl-1H-indol-3-ylmethyl)-phenyl]-6-methyl-nicotinic acid;

2'-(6-carbamimidoyl-1-ethyl-1H-indol-3-ylmethyl)-3-methyl-biphenyl-2-carboxylic acid;

5'-(4-acetyl-benzylcarbamoyl)-2'-(6-carbamimidoyl-1-ethyl-1H-indol-3-ylmethyl)-4-methoxy-biphenyl-2-carboxylic acid;

2'-(6-carbamimidoyl-1-ethyl-1H-indol-3-ylmethyl)-5-methyl-biphenyl-2-carboxylic acid;

2-{2-(6-carbamimidoyl-1-ethyl-1H-indol-3-ylmethyl)-5-[(pyridin-2-ylmethyl)-carbamoyl]-phenoxy}-5-methyl-benzoic acid;

2'-(6-carbamimidoyl-1-ethyl-1H-indazol-3-ylmethyl)-4-methoxy-biphenyl-2-carboxylic acid;

2'-(6-carbamimidoyl-1-ethyl-1H-indazol-3-ylmethyl)-4-methoxy-biphenyl-2-carboxylic acid;

2'-(6-carbamimidoyl-1-ethyl-1H-indazol-3-ylmethyl)-4-methoxy-5'-[(pyridin-3-ylmethyl)-carbamoyl]-biphenyl-2-carboxylic acid;

2'-(6-carbamimidoyl-1-ethyl-1H-indazol-3-ylmethyl)-4-methyl-biphenyl-2-carboxylic acid;

2'-(6-carbamimidoyl-1-ethyl-1H-indazol-3-ylmethyl)-4-chloro-5'-[(pyridin-3-ylmethyl)-carbamoyl]-biphenyl-2-carboxylic acid;

2'-(6-carbamimidoyl-1-ethyl-1H-indazol-3-ylmethyl)-4-methyl-5'-[(pyridin-3-ylmethyl)-carbamoyl]-biphenyl-2-carboxylic acid;

2'-(6-carbamimidoyl-1-ethyl-1H-indazol-3-ylmethyl)-4-methoxy-5'-[(5-methyl-pyrazin-2-ylmethyl)-carbamoyl]-biphenyl-2-carboxylic acid;

2'-(6-carbamimidoyl-1-ethyl-1H-indazol-3-ylmethyl)-4-methyl-5'-[(5-methyl-pyrazin-2-ylmethyl)-carbamoyl]-biphenyl-2-carboxylic acid;

2'-(6-carbamimidoyl-1-ethyl-1H-indazol-3-ylmethyl)-4-methyl-5'-[(pyrimidin-2-ylmethyl)-carbamoyl]-biphenyl-2-carboxylic acid;

2'-(6-carbamimidoyl-1-ethyl-1H-indazol-3-ylmethyl)-4-methoxy-5'-[(pyrimidin-2-ylmethyl)-carbamoyl]-biphenyl-2-carboxylic acid;

2'-[1-ethyl-6-(N-hydroxycarbamimidoyl)-1H-indol-3-ylmethyl]-4-methoxy-5 [(pyridin-2-ylmethyl)-carbamoyl]-biphenyl-2-carboxylic acid;

2'-[1-ethyl-6-(N-hydroxycarbamimidoyl)-1H-indol-3-ylmethyl]-4-methyl-5'-[(5-methylpyrazin-2-ylmethyl)-carbamoyl]-biphenyl-2-carboxylic acid;

2'-[1-ethyl-6-(N-hydroxycarbamimidoyl)-1H-indol-3-ylmethyl]-4-methoxy-5'-[(3-triazolylmethyl)-carbamoyl]-biphenyl-2-carboxylic acid; and 2'-[1-ethyl-6-aminomethyl-1H-indol-3-ylmethyl]-4-methoxy-5'-[(pyridin-2-ylmethyl)-carbamoyl]-biphenyl-2-carboxylic acid;

or a stereoisomer or a pharmaceutically acceptable salt or a solvate thereof.

8. A pharmaceutical composition, comprising: a pharmaceutically acceptable carrier and a therapeutically effective amount of a compound of claim 1.

9. A pharmaceutical composition, comprising: a pharmaceutically acceptable carrier and a therapeutically effective amount of a compound of claim 2.

10. A pharmaceutical composition, comprising: a pharmaceutically acceptable carrier and a therapeutically effective amount of a compound of claim 3.

11. A pharmaceutical composition, comprising: a pharmaceutically acceptable carrier and a therapeutically effective amount of a compound of claim 4.

12. A pharmaceutical composition, comprising: a pharmaceutically acceptable carrier and a therapeutically effective amount of a compound of claim 5.

13. A pharmaceutical composition, comprising: a pharmaceutically acceptable carrier and a therapeutically effective amount of a compound of claim 6.

14. A pharmaceutical composition, comprising: a pharmaceutically acceptable carrier and a therapeutically effective amount of a compound of claim 7.

* * * * *

UNITED STATES PATENT AND TRADEMARK OFFICE
CERTIFICATE OF CORRECTION

PATENT NO.        : 7,417,063 B2
APPLICATION NO. : 11/103139
DATED               : August 26, 2008
INVENTOR(S)      : Joanne M. Smallheer and James R. Corte It is certified that error appears in the above-identified patent and that said Letters Patent is hereby corrected as shown below:

<u>Title Page, Column 2 Item [56]</u>

Line 13 (Other Publications), "Precarboxypeptidase" should read -- Procarboxypeptidase --.

<u>COLUMN 77 Claim 1</u>

Line 24, "0-1 $R^{7a}$" should read -- 0-1 $R^{7b}$ --;

Line 30, "–$CO_2R_g$," should read -- –$CO_2R^g$, --;

Line 32, "$C_{1-4}$ allyl" should read -- $C_{1-4}$ alkyl --; and

Line 63, "–$CH_2)_rNR^7R^8$," should read -- –$(CH_2)_rNR^7R^8$, --.

<u>COLUMN 78 Claim 2</u>

Line 8, "0-1 $R^{12}c$" should read -- 0-1 $R^{12c}$ --;

Line 10, "–$CH_2)_rC_3C_7$" should read -- –$(CH_2)_r$-$C_3$-$C_7$ --;

Line 22, "–$CH_2)_rC_{6-10}$" should read -- –$(CH_2)_r$-$C_{6-10}$ --;

Line 35, "0-2 $R_e$" should read -- 0-2 $R^e$ --;

Line 43, "–$C(O)R^a$" should read -- –$C(O)R^g$ --;

Line 44, "–$C(O)OR^a$" should read -- –$C(O)OR^g$ --;

Line 44, "–$NR^8C(O)R^a$" should read -- –$NR^8C(O)R^g$ --; and

Line 61, "–$CO_2Lt$" should read -- –$CO_2Et$ --.

<u>COLUMN 79</u>

Line 2, Claim 2 "($CH_{92}$-2pyridyl)" should read -- $(CH_2)_2$-2-pyridyl) --;

Line 31, Claim 3 "CONHLt" should read -- CONHEt --;

UNITED STATES PATENT AND TRADEMARK OFFICE
CERTIFICATE OF CORRECTION

PATENT NO. : 7,417,063 B2
APPLICATION NO. : 11/103139
DATED : August 26, 2008
INVENTOR(S) : Joanne M. Smallheer and James R. Corte It is certified that error appears in the above-identified patent and that said Letters Patent is hereby corrected as shown below:

Line 43, Claim 3 "S-CONH" should read -- 5-CONH --;

Line 54, Claim 3 "2-COY-S" should read -- 2-CO$_2$H-5 --; and

Line 63, Claim 3 "X$_5$" should read -- X$^5$ --.

COLUMN 80

Line 37, Claim 4 "X5" should read -- X$^5$ --; and

Line 43, Claim 5 "2-CO$_2$H-S" should read -- 2-CO$_2$H-5 --.

COLUMN 81 Claim 7

Line 12, "-5-" should read -- -5'- --;

Line 40, "acids;" should read -- acid; --;

Line 43, "acids;" should read -- acid; --;

Line 45, "acids;" should read -- acid; --;

Line 47, "acids;" should read -- acid; --; and

Line 64, "acids;" should read -- acid; --.

COLUMN 82 Claim 7

Line 58, "2,3" should read -- 2,3'- --.

COLUMN 83 Claim 7

Line 10, "chioro" should read -- chloro --; and

Line 28, "acid;" should read -- acid ethyl ester; --.

UNITED STATES PATENT AND TRADEMARK OFFICE
CERTIFICATE OF CORRECTION

PATENT NO. : 7,417,063 B2
APPLICATION NO. : 11/103139
DATED : August 26, 2008
INVENTOR(S) : Joanne M. Smallheer and James R. Corte It is certified that error appears in the above-identified patent and that said Letters Patent is hereby corrected as shown below:

COLUMN 84 Claim 7

Line 8, "5" should read -- 5'- --.

Signed and Sealed this

Twelfth Day of May, 2009

JOHN DOLL
*Acting Director of the United States Patent and Trademark Office*